(12) United States Patent
Wang et al.

(10) Patent No.: US 12,383,165 B2
(45) Date of Patent: Aug. 12, 2025

(54) FLEXIBLE SYSTEMS, DEVICES AND METHODS FOR EPIDERMAL MONITORING OF ANALYTES AND BIOMARKERS IN FLUIDS ON SKIN

(71) Applicant: The Regents of the University of California, Oakland, CA (US)

(72) Inventors: Joseph Wang, La Jolla, CA (US); Juliane Sempionatto Moreto, La Jolla, CA (US); Jonas Felipe Kurniawan, La Jolla, CA (US); Aida Martin Galan, La Jolla, CA (US); Jayoung Kim, La Jolla, CA (US); Alan Campbell, La Jolla, CA (US); Jose Roberto Moreto, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1385 days.

(21) Appl. No.: 16/760,431

(22) PCT Filed: Nov. 2, 2018

(86) PCT No.: PCT/US2018/059075
§ 371 (c)(1),
(2) Date: Apr. 29, 2020

(87) PCT Pub. No.: WO2019/090161
PCT Pub. Date: May 9, 2019

(65) Prior Publication Data
US 2020/0337641 A1    Oct. 29, 2020

Related U.S. Application Data

(60) Provisional application No. 62/580,850, filed on Nov. 2, 2017.

(51) Int. Cl.
*A61B 5/145* (2006.01)
*A61B 5/00* (2006.01)
*A61B 5/05* (2021.01)

(52) U.S. Cl.
CPC .......... *A61B 5/145* (2013.01); *A61B 5/14517* (2013.01); *A61B 5/14532* (2013.01);
(Continued)

(58) Field of Classification Search
CPC . A61B 5/145; A61B 5/14517; A61B 5/14532; A61B 5/14546; A61B 5/1477;
(Continued)

(56) References Cited

U.S. PATENT DOCUMENTS 5,422,246 A   6/1995   Koopal et al.
6,120,460 A   9/2000   Abreu
(Continued)

FOREIGN PATENT DOCUMENTS

WO    2010/045247 A1    4/2010

OTHER PUBLICATIONS

Shivashankar, H., Kevin, A. M., Manohar, S. B. S., & Kulkarni, S. M. (2021). Investigation on dielectric properties of PDMS based nanocomposites. Physica B: Condensed Matter, 602, 412357 (Year: 2021).*

(Continued)

*Primary Examiner* — Jennifer Robertson
*Assistant Examiner* — Elina Sohyun Jang
(74) *Attorney, Agent, or Firm* — Perkins Coie LLP

(57) ABSTRACT

Disclosed are devices, systems and methods for epidermal monitoring of a fluid on skin. In some aspects, a device includes an electrochemical sensor comprising two or more electrodes disposed on a first flexible substrate; a microfluidic device comprising a second flexible substrate coupled to the first substrate and structured to include (i) a channel in
(Continued)

a first cavity of the second substrate, (ii) one or more holes that connect to the channel and provide one or more inlets, and (iii) a reservoir connected to the channel, in which the electrochemical sensor is aligned with the reservoir; and an adhesion layer coupled to the microfluidic device and attachable to skin, and the device being operable to detect a biomarker in a fluid in secreted by the skin into the microfluidic device.

32 Claims, 23 Drawing Sheets

(52) U.S. Cl.
CPC ........ *A61B 5/14546* (2013.01); *A61B 5/6833* (2013.01); *A61B 5/05* (2013.01); *A61B 2560/0462* (2013.01); *A61B 2562/028* (2013.01); *A61B 2562/164* (2013.01)

(58) Field of Classification Search
CPC . A61B 5/1486; A61B 5/4266; A61B 5/14514; A61B 5/14521; A61B 10/0064; A61B 5/6833; A61B 5/150969; A61B 5/05; A61B 2560/0462; A61B 2562/028; A61B 2562/164; A61B 5/0002; A61B 2560/0214; A61F 13/024
See application file for complete search history.

(56) References Cited

U.S. PATENT DOCUMENTS

| | | | |
|---|---|---|---|
| 6,438,414 | B1 | 8/2002 | Conn et al. |
| 6,465,091 | B1 | 10/2002 | Ou-Yang |
| 6,546,268 | B1 | 4/2003 | Ishikawa et al. |
| 6,587,705 | B1 | 7/2003 | Kim et al. |
| 12,023,154 | B2 | 7/2024 | Wang et al. |
| 2015/0126834 | A1 | 5/2015 | Wang et al. |
| 2016/0235346 | A1 | 8/2016 | Liu et al. |
| 2016/0338626 | A1 | 11/2016 | Wang et al. |
| 2017/0100035 | A1* | 4/2017 | Heikenfeld ........ A61B 5/14517 |
| 2017/0325724 | A1* | 11/2017 | Wang ................. A61B 5/14532 |
| 2018/0064377 | A1* | 3/2018 | Rogers .................. B01L 3/5027 |
| 2018/0317833 | A1* | 11/2018 | Heikenfeld ........ G01N 33/5438 |
| 2021/0145352 | A1* | 5/2021 | Rogers ............. A61B 5/150022 |

OTHER PUBLICATIONS

Anastasova, S. et al. "A wearable multisensing patch for continuous sweat monitoring" Biosensors and Bioelectronics, 2017, 93, pp. 139-145.
EPO, Extended European Search Report for European Patent Application No. 18874096.3. Mail Date: Jul. 7, 2021. 12 pages.
Martin, A. et al. "Epidermal Microfluidic Electrochemical Detection System: Enhanced Sweat Sampling and Metabolite Detection" ACS Sensors, 2017, 2, 1860-1868.
Nie, C. "Integrated evaporation driven microfluidic device for continuous sweat monitoring" Eindhoven University of Technology, 2016, 119 pages.
Sekretaryova, A. et al. "Bioelectrocatalytic systems for health applications" Biotechnology Advances, 2016, 34, pp. 177-197.
ISA, International Search Report and Written Opinion for International Application No. PCT/US2018/059075. Mail Date: Jan. 23, 2019. 8 pages.
Bandodkar, A. J., et al., Wearable Chemical Sensors: Present Challenges and Future Prospects. ACS Sensors 2016, 1 (5), 464-482.
Bandodkar, A. J., et al., Highly Stretchable Fully-Printed CNT-Based Electrochemical Sensors and Biofuel Cells: Combining Intrinsic and Design-Induced Stretchability. Nano Lett. 2016, 16 , 721-727.
Bandodkar, A. J., et al., All-Printed Magnetically Self-Healing Electrochemical Devices. Sci. Adv. 2016, 2 (11), e1601465, 11 pages.
Bandodkar, A. J., et al., Tattoo-Based Noninvasive Glucose Monitoring: A Proof-of-Concept Study. Anal. Chem. 2015, 87, 394-398.
Choi, D.-H.et al., Wearable Potentiometric Chloride Sweat Sensor: The Critical Role of the Salt Bridge. Anal. Chem. 2016, 88, 12241-12247.
Choi, J., et al., Thin, Soft, Skin-Mounted Microfluidic Networks with Capillary Bursting Valves for Chrono-Sampling of Sweat. Adv. Healthc. Mater. 2017, 6 (5), 1601355, 10 pages.
Curto, V. F., et al., Concept and Development of an Autonomous Wearable Micro-Fluidic Platform for Real Time pH Sweat Analysis. Sensors Actuators, B Chem. 2012, 175, 263-270.
Curto, V. F., et al., Real-Time Sweat pH Monitoring Based on a Wearable Chemical Barcode Micro-Fluidic Platform Incorporating Ionic Liquids. Sensors Actuators, B Chem. 2012, 171-172, 1327-1334.
Dey, R., et al., Electrowetting of sessile drops on soft dielectric elastomer films Microfluidics and Nanofluidics 21 (3), 48, 2017, 12 pages.
Emaminejad, S., et al., Autonomous Sweat Extraction and Analysis Applied to Cystic Fibrosis and Glucose Monitoring Using a Fully Integrated Wearable Platform. Proc. Natl. Acad. Sci. 2017, 114 (18), 4625-4630.
Gagnon, D., et al., The evaporative requirement for heat balance determines whole-body sweat rate during exercise under conditions permitting full evaporation J Physiol. 2013, 591, (11) 2925-2935.
Gao, W., et al., Fully Integrated Wearable Sensor Arrays for Multiplexed in Situ Perspiration Analysis. Nature 2016, 529 (7587), 509-514.
Garcia, M., et al., Copper Nanowires Immobilized on the Boards of Microfluidic Chips for the Rapid and Simultaneous Diagnosis of Galactosemia Diseases in Newborn Urine Samples. Anal. Chem. 2013, 85, 9116-9125.
Glennon, T., et al., "Sweatch": A Wearable Platform for Harvesting and Analysing Sweat Sodium Content. Electroanalysis 2016, 28 (6), 1283-1289.
Harvey, C. J., et al., Formulation and Stability of a Novel Artificial Human Sweat under Conditions of Storage and Use. Toxicol. Vitr. 2010, 24 (6), 1790-1796.
Heikenfeld, J., et al., Non-Invasive Analyte Access and Sensing through Eccrine Sweat: Challenges and Outlook circa. Electroanalysis. 2016, 28, 1242-1249.
Jia, W., et al., Electrochemical Tattoo Biosensors for Real-Time Noninvasive Lactate Monitoring in Human Perspiration. Anal. Chem. 2013, 85 (14), 6553-6560.
Jia, W., et al., Epidermal Biofuel Cells: Energy Harvesting from Human Perspiration, Angew. Chem.—5—Int. Ed. 2013, 52, (28) 7233-7236.
Kanjananimmanont, S., et al., Passive Diffusion of Transdermal Glucose Noninvasive Glucose Sensing Using a Fluorescent Glucose Binding Protein. J Diabetes Sci Technol. 2014; 8(2), 291-298.
Kim, D.-H., et al., Epidermal Electronics. Science Aug. 12, 2011, vol. 333 (6044), 838-843.
Kim, J., et al., Noninvasive Alcohol Monitoring Using a Wearable Tattoo-Based Iontophoretic-Biosensing System. ACS Sensors 2016, 1, 1011-1019.
Kim, J., et al., Wearable Non-Invasive Epidermal Glucose Sensors: A Review. Talanta 2017. DOI: 10.1016/j.talanta.2017.08.077, 163-170.
Koh, A., et al., A Soft, Wearable Microfluidic Device for the Capture, Storage, and Colorimetric Sensing of Sweat. Sci. Transl. Med. 2016, 8 (366), 366ra165, 14 pages.
Lamberti, F., et al., Flow biosensing and sampling in indirect electrochemical detection, Biomicrofluidics. 2012 6 (2) 024114, 14 pages.
Lee, H., et al., A Graphene-Based Electrochemical Device with Thermoresponsive Microneedles for Diabetes Monitoring and Therapy. Nat. Nanotechnol. 2016, 11, 566-572.
Lee, H., et al., Wearable/disposable Sweat-Based Glucose Monitoring Device with Multistage Transdermal Drug Delivery Module. Sci. Adv. 2017, 3, e1601314, 9 pages.

(56) References Cited

OTHER PUBLICATIONS

Li, X., et al., Microfluidic Devices with Disposable Enzyme Electrode for Electrochemical Monitoring of Glucose Concentrations. Electrophoresis 2011, 32 (22), 3201-3206.

Machado-Moreira, C. A., et al., Local Differences in Sweat Secretion from the Head during Rest and Exercise in the Heat. Eur J Appl Physiol. 2008 104 (2), 257-264.

Martinez, A. W., et al., Simple Telemedicine for Developing Regions: Camera Phones and Paper-Based Microfluidic Devices for Real-Time, off-Site Diagnosis. Anal. Chem. 2008, 80 (10) 3699-3707.

Mena-Bravo, A., et al., A sample with limited present applications and promising future in metabolomics. J. Pharmaceutical Biomed. Analysis. 2014, 90, 147, 9 pages.

Morris, D., et al., Diamond, D. Bio-Sensing Textile Based Patch with Integrated Optical Detection System for Sweat Monitoring. Sensors Actuators, B Chem. 2009, 139, 231-236.

Moyer, J., et al., Moyer, J.; Wilson, D.; Finkelshtein, I.; Wong, B.; Potts, R. Correlation Between Sweat Glucose and Blood Glucose in Subjects with Diabetes. Diabetes Technol. Ther. 2012, 14 (5), 398-402.

Oncescu, V., et al., Smartphone Based Health Accessory for Colorimetric Detection of Biomarkers in Sweat and Saliva. Lab Chip 2013, 13, 3232, 7 pages.

Pumera, M., al., Nanomaterials as Electrochemical Detectors in Microfluidics and CE: Fundamentals, Designs, and Applications. Electrophoresis. 2009, 30 (19), 3315-3323.

Roh, C., et al., The deformation of polydimethylsiloxane (PDMS) microfluidic channels filled with embedded circular obstacles under certain circumstances. Molecules 2016, 21 (6), 798, 12 pages.

Shen, L., et al., Point-of-Care Colorimetric Detection with a Smartphone. Lab Chip 2012, 12, 4240, 4 pages.

Sempionatto, J. R., et al., Eyeglasses based wireless electrolyte and metabolite sensor platform. Lab Chip, May 16, 2017, 17(10), 1834-1842, 16 pages.

Sonner, Z., et al., The Microfluidics of the Eccrine Sweat Gland, Including Biomarker Partitioning, Transport, and Biosensing Implications. Biomicrofluidics 2015, 9 (3) 031301, 20 pages.

Taylor, N.A.S., et al., Regional Variations in Transepidermal Water Loss, Eccrine Sweat Gland Density, Sweat Secretion Rates and Electrolyte Composition in Resting and Exercising Humans. Extrem. Physiol. Med. 2013, 2 (1), 4, 30 pages.

Wang, J., Electrochemical Detection for Capillary Electrophoresis Microchips: A Review. Electroanalysis 2005, 17, 1133-1140.

Wang, J., Simultaneous Microchip Enzymatic Measurements of Blood Lactate and Glucose. Anal. Chim. Acta 2007, 585, 11-16.

Wang, J. Study of Electrode Reactions and Interfacial Properties. Anal. Chem. 2006, No. 3, 29-66.

Windmiller, J. R., et al., Wearable Electrochemical Sensors and Biosensors: A Review. Electroanalysis 2013, 25 (1), 29-46.

Xu, S., et al., Soft Microfluidic Assemblies of Sensors, Circuits, and Radios for the Skin. Science 2014, 344 (6179), 70-74.

Xue, Y., et al., Collapse of Microfluidic Channels/reservoirs in Thin, Soft Epidermal Devices. Extrem. Mech. Lett. 2017, 11, 18-23.

European Communication pursuant to Article 94(3) EPC; dated May 23, 2024, EP Application No. 18 874 096.3, 5 pages.

\* cited by examiner

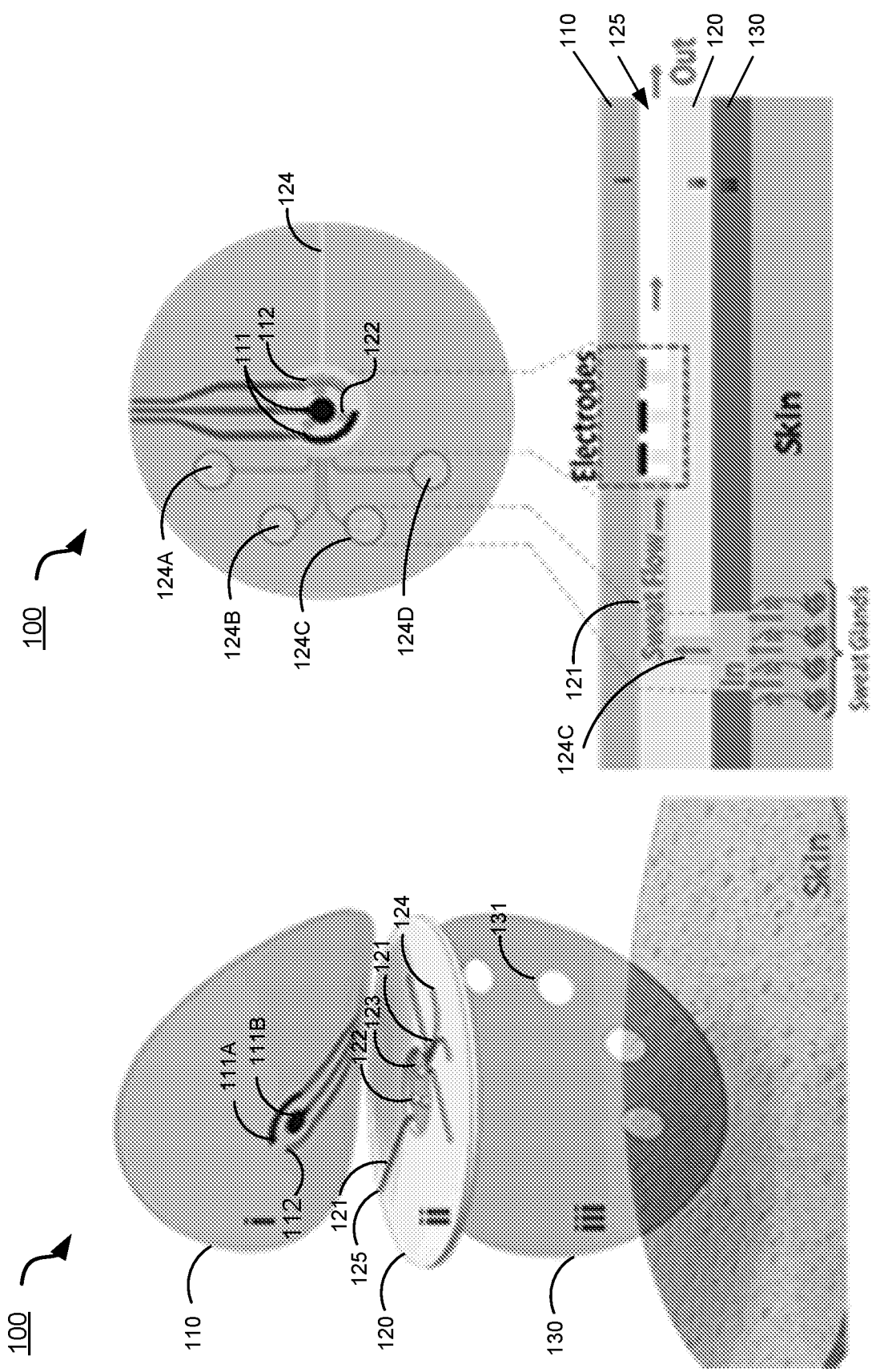

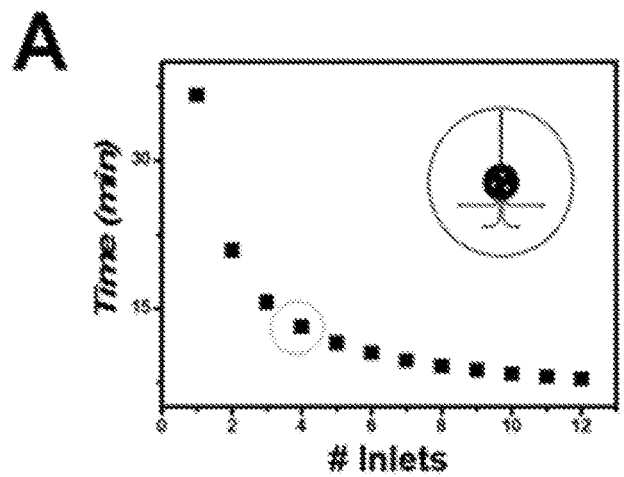 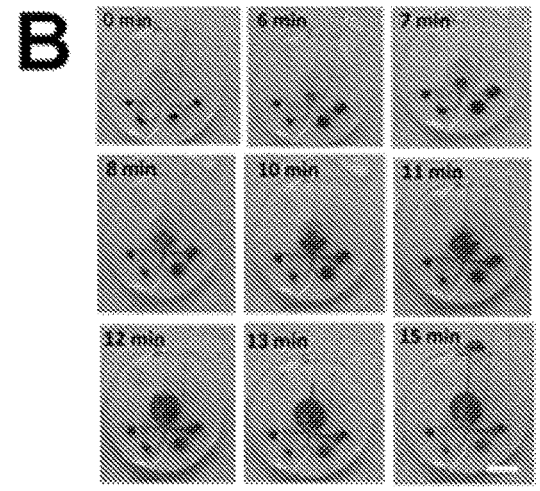
FIG. 2A  FIG. 2B
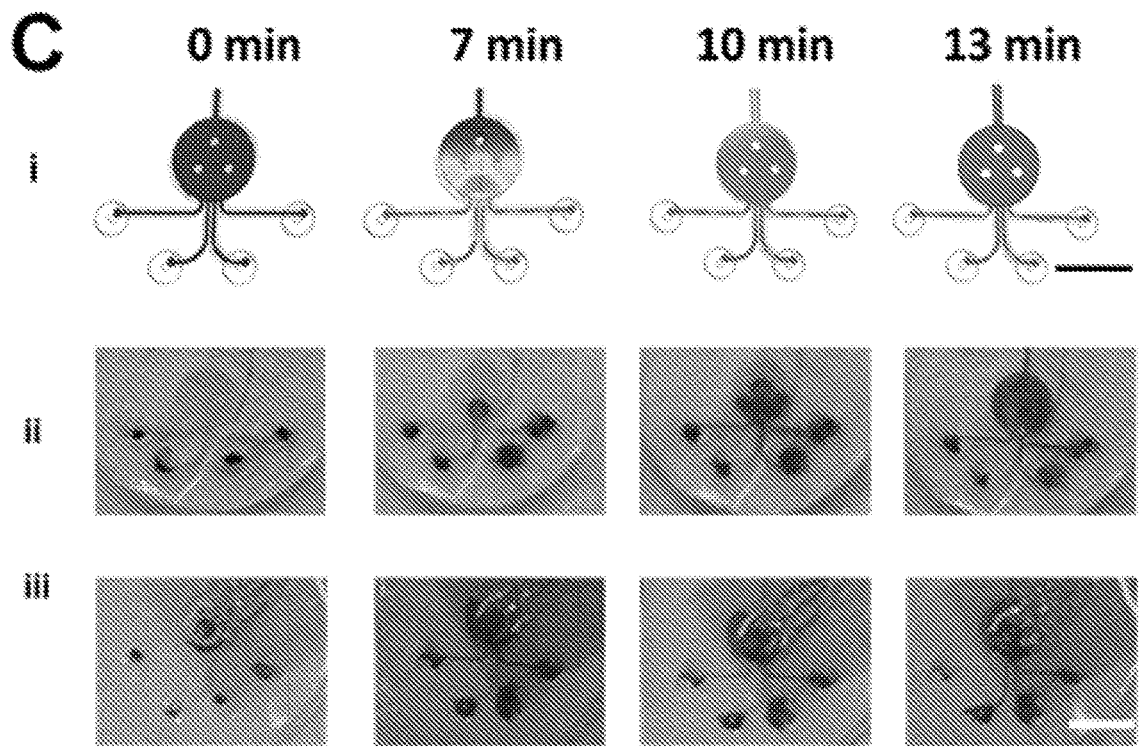
FIG. 2C

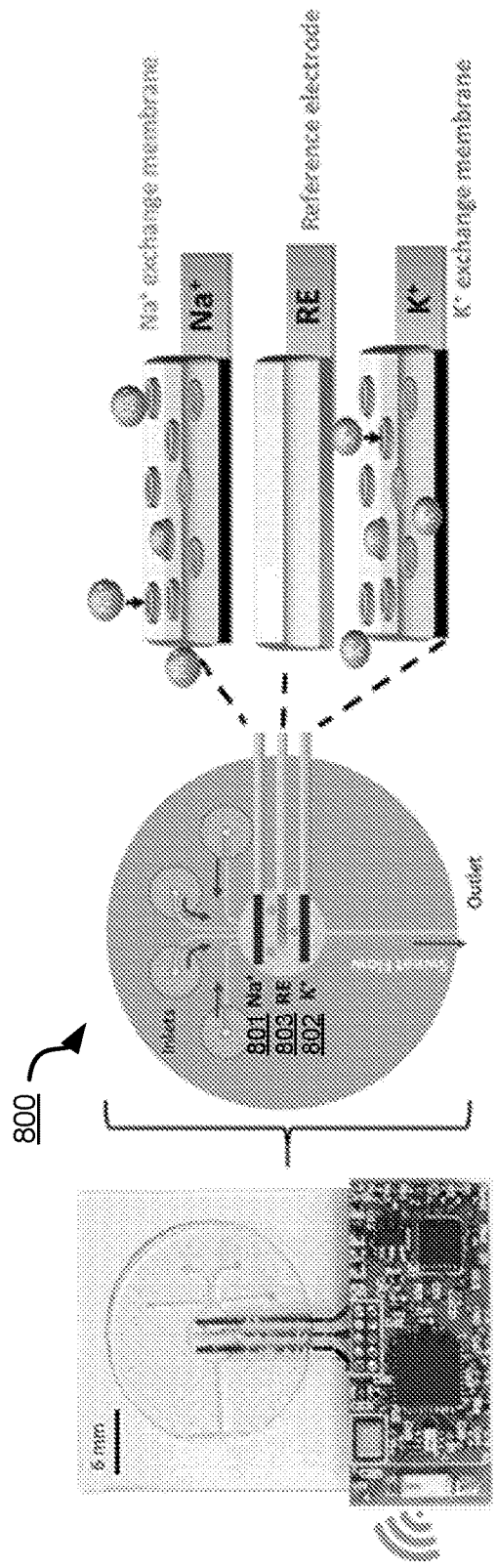
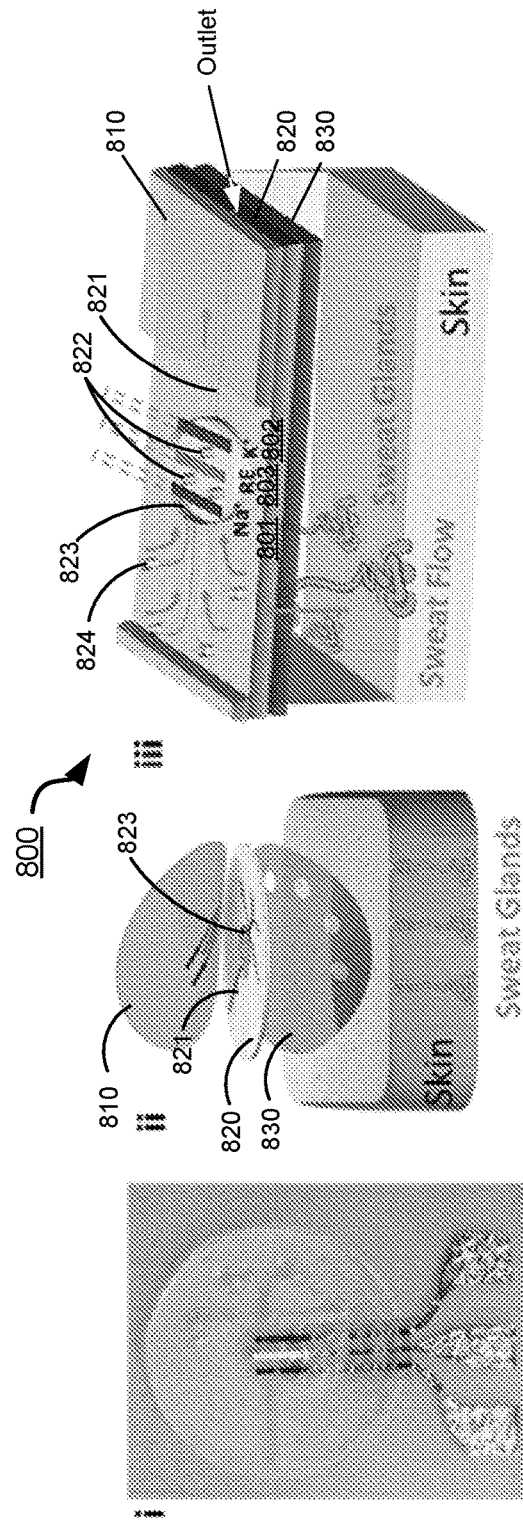
FIG. 8A
FIG. 8B

FLEXIBLE SYSTEMS, DEVICES AND METHODS FOR EPIDERMAL MONITORING OF ANALYTES AND BIOMARKERS IN FLUIDS ON SKIN

CROSS-REFERENCE TO RELATED APPLICATIONS

This patent document claims priorities to and benefits of International Application No. PCT/US18/59075, titled "FLEXIBLE SYSTEMS, DEVICES AND METHODS FOR EPIDERMAL MONITORING OF ANALYTES AND BIOMARKERS IN FLUIDS ON SKIN" and filed on Nov. 2, 2018, which claims priorities to and benefits of U.S. Provisional Patent Application No. 62/580,850, titled "FLEXIBLE SYSTEMS, DEVICES AND METHODS FOR EPIDERMAL MONITORING OF ANALYTES IN FLUIDS ON THE SKIN" and filed on Nov. 2, 2017. The entire content of the aforementioned patent applications is incorporated by reference as part of the disclosure of this patent document.

STATEMENT OF GOVERNMENT SUPPORT

This invention was made with government support under HDTRA1-16-1-0013 awarded by Defense Threat Reduction Agency. The government has certain rights in the invention.

TECHNICAL FIELD

This patent document relates to systems, devices, and processes that use biosensing technologies for analyte monitoring.

BACKGROUND

Sensors based on electrochemical processes can be used to detect a chemical substance or a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Disclosed are systems, devices and methods for epidermal monitoring of sweat using a flexible microfluidic electrochemical platform. Also disclosed are methods and articles of manufacture for producing the flexible microfluidic detection platform, e.g., which can be fabricated through hybridization of lithographic and screen-printed technologies for efficient and fast sweat sampling and continuous real-time electrochemical monitoring of analytes, such as glucose, lactate, and electrolytes.

In some aspects, a wearable electrochemical sensor device includes a first flexible substrate including an electrically insulating material; two or more electrodes disposed on the first flexible substrate; a second flexible substrate coupled to the first flexible substrate on a first side of the second flexible substrate, the second substrate including an electrically insulating material and wherein the second substrate is structured to include (i) a channel that recedes from the surface of the first side of the second flexible substrate, (ii) a first set of one or more holes on a second side of the second flexible substrate that connect to a first region of the channel to provide one or more inlets, (iii) a cavity intersecting the channel beyond the first region to provide a reservoir, (iv) a second set of one or more holes that connect to a second region of the channel opposite the first region to provide one or more outlets, wherein the two or more electrodes on the first flexible substrate are aligned with the reservoir of the second flexible substrate; and an adhesion layer coupled to the second substrate and attachable to skin, the adhesion layer structured to include one or more openings arranged on the adhesion layer to align with the one or more inlets, wherein, when the device is electrically coupled to an electronics unit and adhered to the skin of a user, the device is operable to detect a biomarker in a fluid secreted from the skin of the user into the device.

In some aspects, a device includes an electrochemical sensor comprising two or more electrodes disposed on a first side of a first substrate, the first substrate including a flexible and electrically insulating material; a microfluidic device comprising a second substrate including a flexible and electrically insulating material and coupled to the first side of the first substrate at a top side of the second substrate, the second substrate structured to include (i) a channel in a first cavity on the top side, (ii) one or more holes on a bottom side of the second substrate that connect to the channel and provide one or more inlets, and (iii) a reservoir in a second cavity connected to the channel, wherein the electrochemical sensor on the first substrate is aligned with the reservoir of the second substrate; and an adhesion layer coupled to the second substrate and attachable to skin, the adhesion layer structured to include one or more openings arranged on the adhesion layer to align with the one or more inlets and the outlet of the second substrate, wherein the second substrate is positioned between the first substrate and the adhesion layer, wherein, when the device is electrically coupled to an electronics unit and adhered to the skin of a user, the device is operable to detect a biomarker in a fluid in secreted by the skin into the microfluidic device.

In some aspects, a method for detecting a biomarker in a fluid on skin of a user includes capturing, by a wearable electrochemical sensor device adhered to the skin of the user, a fluid secreted from the skin of the user in one or more inlets of the wearable electrochemical sensor device; transferring, through a channel of the wearable electrochemical device, the captured fluid to a reservoir of the wearable electrochemical sensor device; measuring one or more biomarkers present in the fluid secreted from the skin of the user, the measuring including electrochemically detecting the one or more biomarkers using two or more electrodes positioned in the reservoir of the wearable electrochemical sensor device; and directing the fluid secreted from the skin of the user out of the reservoir to expel from the device, whereby fresh fluid secreted from the skin of the user is transferred in the reservoir of the wearable electrochemical sensor device for continuous electrochemical detection.

In some aspects, a device includes an electrochemical sensor comprising two or more electrodes disposed on a first side of a first substrate, a microfluidic device comprising a second substrate, the second substrate structured to include (i) a channel, (ii) a first set of one or more holes that connect to a first end of the channel and provide one or more inlets, (iii) a reservoir intersecting the channel, wherein the electrochemical sensor on the first substrate is aligned with the reservoir of the second substrate, and (iv) a second set of one or more holes connected to a second end of the channel and provide one or more outlets, wherein the two or more electrodes on the side of the first substrate are aligned with the reservoir the second substrate; and an adhesion layer coupled to the second substrate and attachable to skin, the adhesion layer structured to include one or more openings arranged on the adhesion layer to align with the one or more inlets, wherein when the device is electrically coupled to an electronics unit and adhered to the skin of a user, the device is operable to detect a biomarker in a fluid secreted from the skin of the user into the microfluidic device.

In some embodiments, like those described herein, a flexible microfluidic electrochemical platform in accordance with the present technology includes a skin-mounted device that merges lab-on-a-chip and electrochemical detection technologies, integrated with a miniaturized flexible electronic board for real-time wireless data transmission to a smart device. In some implementations, the platform can include a biofuel cell device integrated in the for power generation. In some implementations, the platform includes a flexible substrate, e.g., polydimethylsiloxane (PDMS), and can be easily mounted on the epidermis to achieve conformal contact without hindrance to the wearer. For example, such device displays resiliency against continuous mechanical deformation expected from such epidermal wear. The device can include a fully integrated electrochemical system that can include two, three or four electrodes. For example, the versatile configuration allows the electrochemical detection of target analytes via amperometric measurements with extension to other time-dependent electrochemical measurements (e.g., potentiometric measurement, square-wave voltammetry, etc.) for biosensing of clinically relevant (bio) chemical markers in sweat (e.g., lactate, glucose, etc.). Also, for example, two electrode configuration as a biofuel cell can provide for consistent electrical energy generation using the chemical energy found in these (bio) chemical compounds.

The subject matter described in this patent document can be implemented in specific ways that provide one or more of the following features.

BRIEF DESCRIPTION OF THE DRAWINGS

FIGS. 1A-1C show illustrative diagrams of an example embodiment of a flexible microfluidic device of the flexible epidermal microfluidic platform in accordance with the present technology.

FIGS. 2A-2C show data plots and images depicting the example theoretical simulation and experimental verification results of required time to fill microfluidic reservoir.

FIGS. 8A and 8B show illustrative diagrams and images depicting an example embodiment of a microfluidic potentiometric platform in accordance with the present technology.

DETAILED DESCRIPTION

Figure 1C:
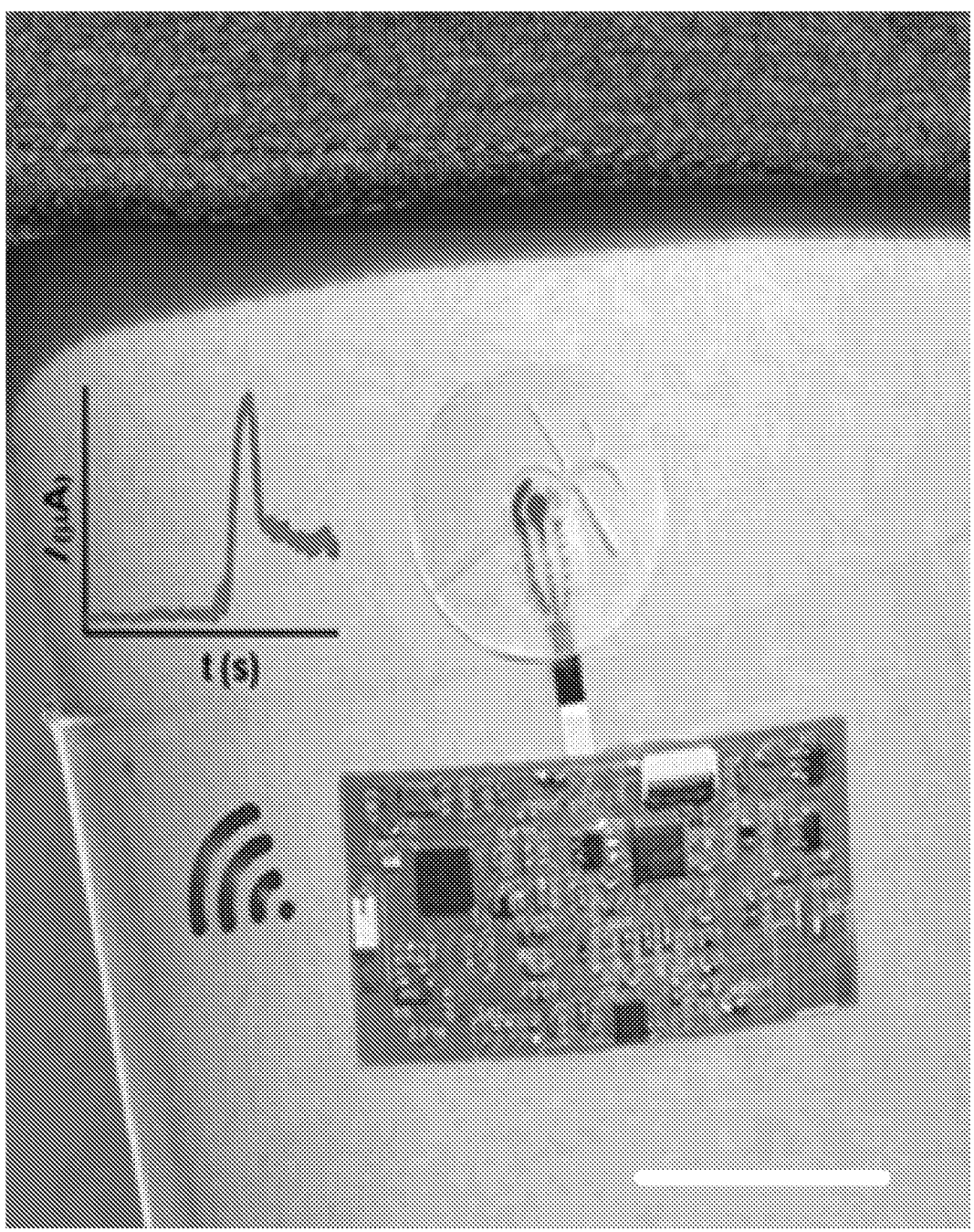

Wearable sensors have received tremendous attention recently owing to their great promise for a wide range of applications in the healthcare, fitness, security and environmental fields. While early efforts have focused on monitoring the physical status or electrophysiology of the wearer, non-invasive wearable chemical sensors are currently under intense research and development. Continuous monitoring of clinically and performance relevant (bio) markers has, thus, been achieved using different biofluids such as saliva, sweat or tears. Among these new wearable chemical sensors, epidermal sweat-analyzing platforms have promoted a revolution of skin-conformal materials with distinct flexibility, stretchability, and even self-healing properties.

Sweat represents an attractive biofluid for non-invasive monitoring of the wearer's physiological state owing to its relative case of collection and its abundance of biochemical information. These advantages have motivated tremendous efforts toward the development of various epidermal sweat chemical sensing devices for monitoring metabolites and electrolytes. For example, analyte detection can be accomplished via electrochemical or colorimetric methods and by employing different form factors (e.g., wrist-bands, temporary tattoos, patches, bandages, or textile platforms). Yet, several key challenges have not been addressed for successful realization of reliable, non-invasive, and accurate real-time monitoring in sweat. Some of these challenges include (1) irregular or low sweat generation rates during exercise; (2) susceptibility of contamination with skin (bio) markers; (3) mixing and carry-over between freshly generated sweat and old sweat; (4) irreproducible sample transport over the detector surface; and (5) lack of control of sample evaporation and volume. Addressing these challenges requires significant advances in sweat collection and transport.

Recently, the miniaturization of sweat sensors in soft microfluidic devices to allow consistent measurements at low sweat rates, avoid sweat dilution and minimize external contamination have been proposed for optical analyses of microliter sweat volumes. However, these devices require long times for filling the collection reservoir and present poor quantitative and dynamic response for the biomarkers. While epidermally wearable biofuel cells have been reported, there has yet to be demonstrated a viable epidermally wearable platform capable of constant, rapid fluid transport to biofluid, like sweat, to the electrochemical device.

Disclosed are systems, devices and methods for a wearable flexible microfluidic electrochemical platform able to monitor analytes and biomarkers and/or harvest energy from biofluids, such as sweat. Also disclosed are methods of manufacture for producing the flexible microfluidic electrochemical detection and/or fuel cell platform, e.g., which can be fabricated through hybridization of lithographic and screen-printed technologies for efficient and fast sweat sampling and continuous real-time electrochemical monitoring of analytes, such as glucose, lactate, electrolytes and other analytes and biomarkers.

In some example embodiments, the disclosed flexible microfluidic electrochemical platform can provide integration of enzyme-based electrochemical sensors and biofuel cells in soft microfluidic devices for a selective, real-time and accurate quantitative response for the biomarkers under study.

The disclosed systems, devices and methods provide an integrated wearable epidermal electrochemical sensing and soft microfluidic platform capable of real-time continuous monitoring of analytes in fluids on a user's skin, such as sweat metabolites including glucose or lactate. Example embodiments of the electrochemical devices are extremely attractive for meeting the requirements of on-body wearable systems and of chip-based analytical microsystems (e.g., 'Lab-on-a-Chip'), e.g., based on their miniaturization and low-power requirements, low costs, high performance and fast data acquisition. The disclosed soft skin-mounted microchip fluidic detection systems combine the advantages of electrochemical epidermal sensing and of electrochemical microchip detectors and integrate lithographic and screen-printing fabrication approaches to leverage their respective advantages. For example, various embodiments of the system can be implemented to monitor analytes from intrinsic sweat secretion and flow, which obviates the needs for complicated electrokinetic (external fields) or hydrodynamic (external pumps) systems characteristic of microchip electrochemical systems.

Example embodiments and implementations are described which demonstrate a soft, skin-mounted device that can be used as a lab-on-a-chip for electrochemical detection, e.g., integrated with a miniaturized flexible electronic board for real-time wireless data transmission to a mobile device. Example simulation modelling of the device design and sweat flow conditions allowed optimization of the sampling process and the microchannel layout for achieving attractive fluid dynamics and rapid filling of the detection reservoir (e.g., within 8 minutes (min) from starting exercise). An example of the wearable micro-device enabled efficient natural sweat pumping to the electrochemical detection chamber containing the enzyme-modified electrode transducers. Fabrication techniques described for the example device can allow cost-effectives say to produce the device, and the example device can be easily mounted on the epidermis without hindrance to the wearer, e.g., displaying resiliency against continuous mechanical deformation expected from such epidermal wear. Amperometric biosensing of lactate and glucose from the rapidly generated sweat, using the corresponding immobilized oxidase enzymes, were wirelessly monitored during cycling activity of different healthy subjects. This demonstrated ability to monitor sweat glucose levels may introduce new possibilities for effective diabetes management, while similar lactate monitoring paves the way for new wearable fitness applications. The disclosed epidermal microfluidic electrochemical detection strategy may represent an attractive alternative to recently reported colorimetric sweat-monitoring methods, and hence holds considerable promise for practical fitness or health monitoring applications.

In some embodiments, a device for epidermal electrochemical sensing includes a first flexible substrate including an electrically insulating material, which the first flexible substrate is flexible, stretchable, compressible, and/or bendable; two or more electrodes disposed on the first flexible substrate; a second flexible substrate coupled to the first flexible substrate, the second substrate including an electrically insulating material, which the second flexible substrate is flexible, stretchable, compressible, and/or bendable, wherein the second substrates is structured to include (i) a channel, (ii) a first set of one or more holes that connect to a first end of the channel and provide one or more inlets, (iii) a reservoir intersecting the channel and (iv) a second set of one or more holes that connect to a second end of the channel and provide one or more outlets, wherein the two or more electrodes on the first flexible substrate are aligned with the reservoir of the second flexible substrate; and an adhesion layer coupled to the second substrate and attachable to skin, the adhesion layer structured to include one or more openings arranged on the adhesion layer to align with the one or more inlets, wherein, when the device is electrically coupled to an electronics unit and adhered to the skin of a user, the device is operable to detect a biomarker in a fluid secreted from the skin of the user into the device.

FIGS. 1A and 1B show illustrative diagrams of an example embodiment of the device for epidermal electrochemical sensing in accordance with the present technology, labeled device 100. FIG. 1A shows an exploded perspective view of the device 100 and FIG. 1B shows a two-dimensional top view and cross-sectional view when applied to skin of the device 100. The device 100 includes a flexible layer 110 (e.g., first flexible substrate) that is formed of an electrically insulating material that is mechanically flexible, stretchable and bendable (referred to simply as "flexible"). The device 100 includes two or more electrodes 111 (shown as electrodes 111A and 111B in FIG. 1A), which are disposed on a first side of the flexible layer 110. In some embodiments, the device 100 is configured to include the two or more electrodes 111 and a reference electrode 112 disposed on the first side of the flexible layer 110, in which this three (or more) electrode contingent can be used, for example, in certain electrochemical sensing modalities requiring a working electrode, counter electrode and reference electrode. In some embodiments, one or more of the electrodes includes a catalyst or a reactant on the surface corresponding to an analyte in the fluid, such that, together with another electrode disposed on the first flexible layer 110 in a location separated from the catalyst- or reactant-modified electrode, the electrodes are operable to measure an electrical signal corresponding to a redox reaction including the chemical substance and the analyte at the electrochemical sensor.

The device 100 is structured to have the first side of the flexible layer 110 coupled to a first side of a second flexible layer 120 (e.g., second flexible substrate), which is formed of an electrically insulating material that is also mechanically flexible, stretchable and bendable. In some examples, the flexible layer 110 and the second flexible layer 120 are of the same material; whereas in other examples, the flexible layer 110 and the second flexible layer 120 are of different flexible and electrically insulative materials.

The second flexible layer 120 includes a channel 121 that spans across at least a portion of the second flexible layer 120. The channel 121 intersects with a reservoir 123 of the second flexible layer 120, which recedes from the surface of the first side to a certain depth within the flexible layer 120. For example, the depth of the reservoir 123 can be a configured as a percentage of the total thickness of the second flexible layer 120, e.g. such as in a range of 25% to 99%, or 100% (all the way through the 100%). Similarly, for example, the depth of the channel 121 can be configured as a percentage of the total thickness, and may be of the same depth as or lesser depth than that of the reservoir 123. In some embodiments, the intersection is not at the end of the channel 121. For example, in some embodiments, the reservoir 123 is positioned at a nonterminal point along the channel 121 as shown in FIG. 1A; whereas in some embodiments, the reservoir 123 is positioned at the end of the channel 121 as shown in FIG. 1B.

The device 100 is configured to align the flexible layer 110 and the second flexible layer 120 such that the two or more electrodes 111 and the reference electrode 112 of the flexible layer 110 are aligned with the reservoir 123 of the flexible layer 120. In some embodiments, the reservoir 123 includes one or more pillar structures 122 at the bottom of the reservoir 123 to support the flexible layer 110 above the reservoir 123, e.g., preserving the volume of the reservoir. In some embodiments, the one or more pillar structures 122 can be positioned to support the electrodes (e.g., two or more electrodes 111 and the reference electrode 112) or their interconnects on the first side of the flexible layer 110. However, in some embodiments, the reservoir 123 does not include a pillar structure 122. In some embodiments, the reservoir 123 does not pass through the entire depth of the flexible layer 120 as shown in FIG. 1B, and may include the pillar structures; whereas in some embodiments, the reservoir 123 passes through the entire depth of the flexible layer 120.

The second flexible layer 120 is configured to include one or more inlets 124 connected to a first end of the channel 121. In example embodiments of the device 100 including two or more inlets, the inlets 124 can be connected to the channel 121 by tributary channels that span off of the channel 121 to the inlets 124. The diagram shown in FIGS. 1A and 1B depicts an example of the device 100 including four inlets 124, e.g., labeled as inlets 124A, 124B, 124C and 124D in FIG. 1B. While the example shown in FIGS. 1A and 1B has four inlets, the device 100 can also be configured to have 1 to 10 inlets, 1 to 20 inlets, 1 to 30 inlets, 1 to 40 inlets, or 1 to 50 inlets, or other configurations of inlets. The second flexible layer 120 is configured to include one or more outlets 125 connected to a second end of the channel 121. While the example of device 100 in FIGS. 1A-1B has one outlet, the device 100 can also be configured to have 1 to 10 outlets, 1 to 5 outlets, 1 to 10 outlets, 1 to 15 outlets, or 1 to 20 outlets, or other configurations of outlets.

In various implementations, the second flexible layer 120 operates as a microfluidic device for the device 100 by controlling inflow and outflow of biofluids, such as sweat, to an active region of the device where the electrodes are provided for analyte detection and/or other functionality of the device, discussed below.

The device 100 is structured to include an adhesion layer 130 coupled to the opposing side of the second flexible layer 120 (e.g., on the side in which the first flexible layer 110 is not coupled). The adhesion layer is configured to include one or more holes 131 that align with the one or more inlets 124 of the flexible layer 120 as shown in FIG. 1A. In some embodiments, the adhesion layer is configured to include one or more channels or holes that interface with a side edge of the adhesion layer to allow expulsion of fluid from the device 100.

In implementations, the device 100 enables a continuous replenishment of the fluid secreted from the skin of the user to the reservoir 123 of the device 100. For example, based on the structure of the microfluidic device, the device 100 can provide a flow rate consistent with the natural flow rate in which the fluid is secreted from the user and can minimize back pressure by providing an unobstructed pathway by which the secreted fluid can flow through the device 100. The device 100 provides continuous replenishment of the fluid secreted from the skin through the judicious alignment of each the flexible layer 110, flexible layer 120, and adhesion layer 130. For example, when the device 100 is adhered to the skin of a user via the adhesion layer 130 as shown in FIG. 1B, fluid is secreted from the skin of the user and into the one or more holes 131. The fluid then enters into the one or more inlets 124 of the second flexible layer 120 aligned with the one or more holes 131 of the adhesion layer 130. Next, the fluid travels through the channel 121 and into the reservoir 123 and passes over the two or more electrodes 111 of the flexible layer 110, which are aligned with the reservoir 123 of the flexible layer 120. Once the fluid pass over the two or more electrodes 111 (which can include electrode 112), the device 100 is able to detect and/or measure biomarkers in the fluid secreted by the user. The fluid travels out of the reservoir 123 through the opposing end of the channel 121 and exits the device through the one or more outlets 125. In some embodiments, the opposing end of the channel 121 and/or the one or more outlets are parallel to the skin of the user, enabling previously measured fluid to flow out of the reservoir 123, thereby enabling freshly secreted fluid to enter. Accordingly, the geometry of the device 100 enables a precise alignment of the flexible layer 110, flexible layer 120, and adhesion layer 130, providing an unobstructed pathway for a continuous replenishment of the fluid secreted from the skin of the user. In implementations, the device 100 does not require the use of a flow cell, microfluidic pump, or other external pressure driving unit; yet in some implementations, the device 100 can interface with a flow cell, pump or the like augment fluid flow control within the microfluidic module of the device 100.

In some embodiments, like the example shown in FIGS. 1A and 1B, the flexible layer 110, flexible layer 120 and the adhesion layer 130 are configured as three circular, flexible layers. In some embodiments, the diameter of the circle is in a range of 1 cm to 10 cm. In some embodiments, the flexible layer 110, flexible layer 120, and the adhesion layer 130 do not have the same geometry. For example, in some embodiments, the flexible layer 110, flexible layer 120, and adhesion layer all have a different geometry but still maintain the necessary configuration to couple the features of each layer. In some embodiments, the flexible layer 110, flexible layer 120, and the adhesion layer 130 are formed to have a circular, rectangular, oval, oblong, triangular geometry or any combination thereof. In some embodiments, the device 100 can be formed as a decorative design such as a tattoo. For example, in some embodiments the flexible layer 110, flexible layer 120, and the adhesion layer 130 have the same or differing shapes (aligning in the active region) such that the device 100 forms a design of interest, such as a butterfly, heart, star, or sports figure. In some embodiments, the flexible layer 110, flexible layer 120, and adhesion layer 130 can include different colors as part of the decorative design. Non-limiting examples of colors of the flexible layer 110, flexible layer 120, and adhesion layer 130 include orange, purple, blue, yellow, green, pink, red, violet or any combination thereof. In some embodiments, the device 100 is the same color as the skin of the user such that the device 100 is not observable (i.e., camouflaged). In some embodiments, the flexible layer 110, flexible layer 120, and the adhesion layer 130 are flexible and electrically insulating material. Non-limiting examples of flexible and electrically insulating materials of the first layer 110, second layer 120 and/or adhesion layer 130 include polydimethylsiloxane (PDMS), thiolenes, elastomers, liquid metals, and tegarderms.

As discussed above, the geometry of the device 100 enables a constant, rapid filling of the reservoir 123 of the device with fluid secreted from the skin of the user, in which sweat, for example, can enter into the more or more inlets 124 and fill the reservoir 123 in a short amount of time without a need to increase the volume of the reservoir 123. In some implementations, the reservoir 123 of the device 100 can fill with the fluid secreted from the skin of the user in less than 5 minutes, less than 3 minutes, or less than 1 minute from the time in which the user started to sweat. In contrast, traditional sweat monitoring devices have filling times ranging between 18 min and 3.2 h. As such, the device 100 provides a 2-fold improvement over conventional sweat monitoring microfluidic devices.

Various embodiments of the deice 100 can include one or more of the following features. In some embodiments, the flexible layer 110 of device 100 includes at least two, at least three, at least four, or at least five electrodes 111, which can be used as one or more electrochemical sensor electrode contingents. In some embodiments, the electrodes 111 are ion-selective electrodes. Non-limiting examples of ion-selective electrodes include sodium, potassium, chloride, bicarbonate, calcium, phosphate, magnesium, copper, zinc, iron, manganese, molybdenum, copper, and chromium ion-selective electrodes.

In implementations, the device 100 is resilient to mechanical deformations (i.e., the transformation of a material from one configuration to a different configuration). Non-limiting examples of mechanical deformations include bending, stretching, compressing, and/or twisting. The resilience of the device 100 is attributable to the flexible materials that comprise the flexible layer 110, flexible layer 120, and the adhesion layer 130. A resilience to mechanical deformation increases the compatibility of the device 100 to the epidermis of a user, where the device is able to conform with the changing morphology of the epidermis when the user is in motion. This offers advantages over traditional wearable devices that are predominately comprised of integrated circuits on solid substrates, which are mechanically incompatible with the soft and changing morphology of the epidermis of the user. As such, the resilience of the device 100 enables a more reliable measurement and repeatable use of the device for detecting biomarkers secreted for the skin of the user as compared to traditional wearable devices.

In some implementations, the device 100 is operable to detect one or more biomarkers. Non-limiting examples of biomarkers include electrolytes, glucose, lactate, pro-inflammatory cytokines, anti-inflammatory cytokines, catecholamines, neuropeptides, and/or proteins. In some implementations, the device 100 is operable to detect two or more electrolytes secreted from the sweat of the user. Non-limiting examples of electrolytes include sodium, potassium, chloride, bicarbonate, calcium, phosphate, magnesium, copper, zinc, iron, manganese, molybdenum, copper, and chromium.

In some implementations, the device 100 enables detection of physiological, biological, or chemical signals from the skin. For example, in some implementations, the device 100 is operable for monitoring the environment of a user by detecting physiological fluids residing on the surface of the epidermis (e.g., sweat). For example, the device 100 can be used to measure chemical substances in fluid secreted from the skin of the user where the fluids can provide information regarding the physical conditions of the environment and the health of the user. In some implementations, by analyzing the chemical substances found in the fluid secreted from the skin of the user, the device 100 can provide an assessment of the overall exposure of the user to chemical or biological agents and/or hazardous agents.

In some implementations, the device 100 enables a direct measurement of electrolytes such as sodium and potassium to provide an assessment of the hydration of the user. Dehydration (i.e., an excessive loss of water from body tissues) is accompanied by an imbalance in electrolytes and in clinical settings, is frequently diagnosed by obtaining and then, analyzing a blood sample from a patient. The process of obtaining a blood sample from a patient is invasive and can also alter and/or influence the electrolyte levels of the blood sample. Accordingly, the method of diagnosing dehydration by analyzing a blood sample often causes discomfort for the patient, introduces inaccuracies in the biomarker levels, and is often irreproducible. In contrast, device 100 enables a non-invasive and direct measurement of electrolyte levels of a user by requiring only a measurement of sweat naturally secreted from the user immediately following secretion. As such, the device 100 provides a more accurate and reproducible measurement of electrolytes with minimal to no disruption to the user as compared to methods frequently used in clinical settings for diagnosing dehydration.

In some embodiments, the two or more electrodes 111 of the flexible layer 110 form an electrochemical sensor, and the device 100 includes an electronics unit is electrically coupled to the electrochemical sensor (e.g., the two or more electrodes 111) via electrical interconnects as shown in FIG. 1C. In some embodiments, the electronics unit is configured to supply electrical energy to the electrochemical sensor. In some embodiments, the device 100 further comprises a biofuel cell, wherein the device 100 includes the electronics unit electrically coupled to the electrochemical sensor via electrical interconnects and the biofuel cell. In some embodiments, the biofuel cell is configured to supply electrical energy to the electrochemical sensor. In some embodiments, the biofuel cell is a microfluidic biofuel cell including separate anodic and cathodic fluid reservoirs containing enzyme-functionalized porous packing fabricated between two layers. In some embodiments, the electrochemical sensor is operable to obtain one or more of amperometric measurement, potentiometric measurement, or square-wave voltammetric measurement. In some embodiments, the device 100 further comprises a transducer element to transform a signal resulting from detection of the biomarker into a different signal addressable by optical or electronic means. In another embodiment, the electronic unit of the device includes a signal conditioning circuit to amplify signals detected by the electrochemical sensor, a data processing unit including a processor and memory to process data based on the measured signals, and a wireless communications unit to wirelessly transmit the processed signals to an external device. In some embodiments, the wireless communications unit includes a Bluetooth® Low Energy chipset, also referred to herein as "BLE."

In some embodiments, aspects of the present technology are directed to methods of monitoring and/or detecting biomarkers in a fluid secreted from skin, e.g., using example embodiments of the device 100. In some embodiments, a method for monitoring analytes or biomarkers in a biofluid includes (a) collecting the fluid secreted from the skin of the user in a reservoir of an electrochemical device; (b) measuring the biomarkers in the fluid secreted from the skin of the user; and (c) directing the fluid secreted from the skin of the user out of the reservoir, whereby fresh fluid secreted from the skin of the user is collected in the reservoir of the electrochemical device, and wherein the electrochemical device is adhered to the skin of the user.

Referring back to FIGS. 1A-IC, the example flexible microfluidic electrochemical sensor device includes two soft, conforming polydimethylsiloxane (PDMS) layers, along with a double-sided adhesive layer. The first PDMS layer (layer 110) integrates the electrode system, and the second layer (layer 120 contains the microfluidic channels (including inlets and outlet) and the detection reservoir. The flexible microfluidic electrochemical sensor device can thus be easily adhered to the epidermis, and provides conformal contact to the skin sweat pores to route sweat rapidly toward the sensing reservoir while enduring repetitive mechanical deformations experienced by the wearer. FIG. 1C shows a photograph of the example microfluidic device integrated with wireless conformal electronics on skin with lithography-based gold current collectors and screen-printed Ag/AgCl (RE) and Prussian blue (WE and CE). Inset of the diagram of FIG. 1C shows a plot depicting the electrochemical temporal response to sweat metabolites, and the scale bar in the diagrams is 5 mm.

Successful use of electrochemical flow detectors requires high rate of mass transport along with well-defined hydrodynamic conditions. In example implementations described herein, the example epidermal microfluidic-based electrochemical detection system was theoretically modelled and experimentally demonstrated toward achieving short sweat sampling time, fast sweat flow rates, and effective transport over the detector surface. Through this design process, for example, a dramatically enhanced sweat sampling rate was demonstrated, e.g., as compared to existing electrochemical microchips, coupled to specific and rapid electrochemical detection of sweat biomarkers. This enhanced rate of sweat sampling effectively addresses several existing challenges of accurate epidermal electrochemical sensing by continuously providing a sufficient amount of sweat to the detector surface for robust sensing while rapidly eliminating initial contaminating glucose concentrations present on the skin surface or within sweat pores. In the example implementations, the example electrochemical microchip flow detector relies on oxidase-based biosensors and Prussian Blue-modified amperometric transducers, fabricated with lithographic and screen printed technologies. Furthermore, the example device used in the example experimental implementations has been integrated with a skin-conformal 5.0×2.4 $cm^2$ flexible electronic board for wireless real-time data transmission, as depicted in the illustrative diagram of FIG. 1C. The attractive fluid dynamics and analytical performance was demonstrated using on-body sweat metabolite monitoring during cycling activity of several healthy human subjects. The example results showed that facile temporal detection of sweat glucose and lactate concentrations, which may provide new opportunities for diabetes management and fitness monitoring, laying the foundation for multimodal wearable sweat sensor system.

Example fabrication techniques and implementations are described including example results demonstrating at least some of the capability of the disclosed flexible epidermal microfluidic devices for various sensing and actuation applications.

Example Fabrication Method of Microfluidic Electrochemical Sensors (a) Fabrication of Flexible Microfluidic Channels In example implementations, a 50 nm layer of chromium (Cr) was first deposited using an electron beam evaporator (Temescal BJD 1800) to act as an etch mask. Photolithography was then used to pattern the microfluidic channels. The unmasked portions of the silicon (Si) wafer were etched by Deep Reactive Ion Etching (Plasmalab Oxford P100), yielding 300 μm tall patterns. Depth measurements of the Si master were performed using a Dektak 150 surface profiler (Vecco, NY). A 70 nm layer of poly(methyl-methacrylate) (PMMA 950 A2, MicroChem, USA) was next spin-casted onto the Si master, followed by soft baking at 180° C. to reduce Si adhesion to the master. A Si layer of 500 μm (Dow Corning, Sylgard 184) was then spin-casted onto the Si master to yield the final microfluidic pattern, as shown in layer ii of FIG. 1A.

(b) Fabrication of Electrochemical Biosensors

In example implementations, a 70 nm layer of PMMA was spin-casted onto a 4" Si wafer to serve as a sacrificial layer. Subsequently, polyimide (PI-2545, HD Microsystems, USA) was spin-casted to yield a 1.6 μm film on top of the PMMA, followed by soft baking at 110° C. and 150° C. on a contact hotplate to remove volatile solvents, and then cured at 250° C. in a vacuum oven. Photolithography was used to pattern sensors and interconnect layers of titanium (Ti) (10 nm)/Copper (Cu) (550 nm)/Ti (20 nm)/Gold (Au) (200 nm) deposited by an electron beam evaporator (Temescal BJD 1800).

Figure 1D:
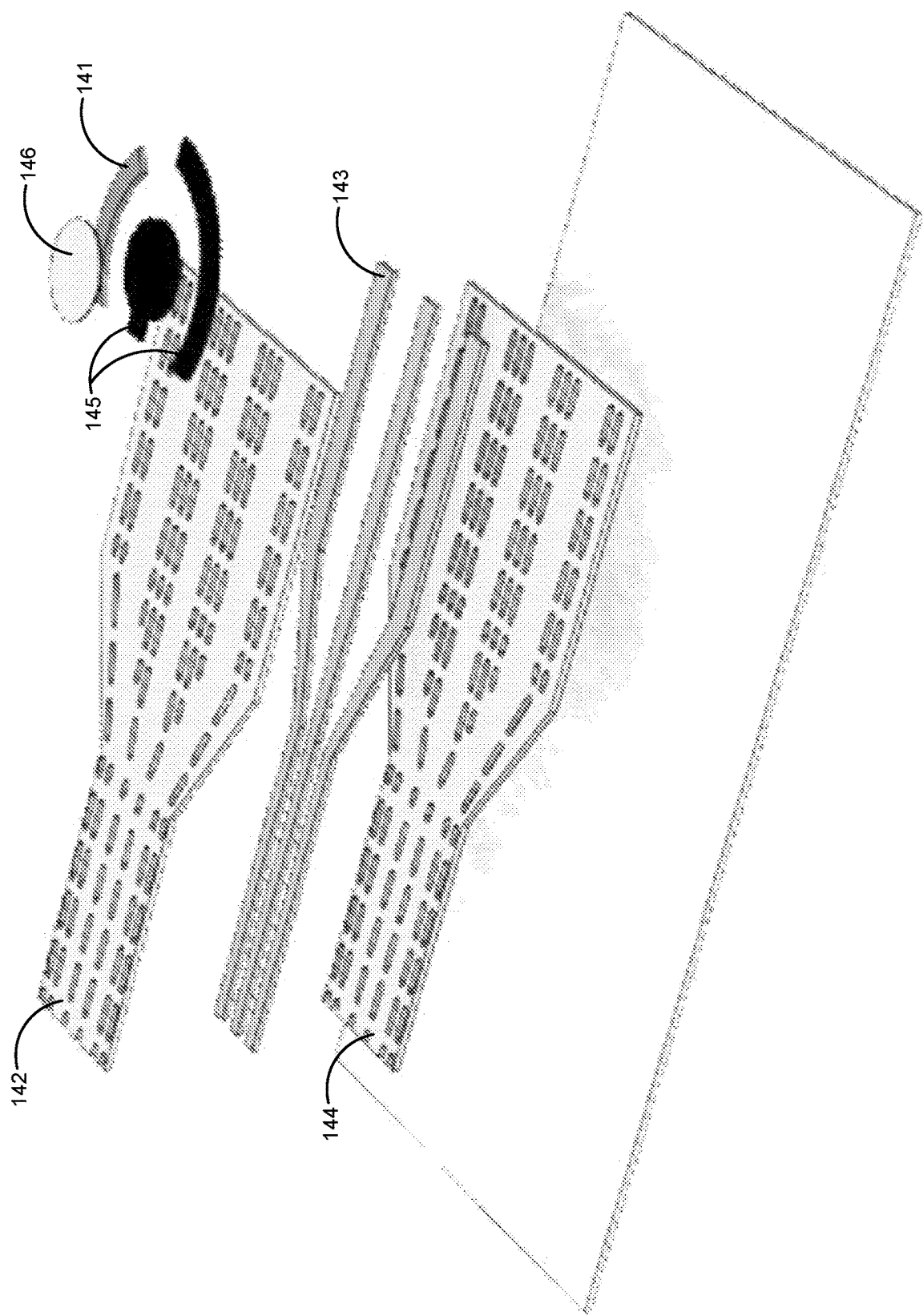
FIG. 1D shows an illustrative schematic depicting an example sweat biomarker sensor fabrication technique.

A second layer of polyimide of the same thickness as the bottom layer was placed on the sensor/interconnect layer on a neutral mechanical plane, as depicted in FIG. 1D. This top polyimide layer also served as electrical insulation and strain isolation. Reactive Ion Etching (Plasmalab Oxford P80) was used to etch the polyimide and define the mesh layout of the array, exposing only the bonding pads and the sensors. The PMMA layer was undercut with boiling acetone to enable the removal of the mesh from the Si wafer using a water-soluble poly vinyl alcohol (PVA) tape (3M Company, Maplewood, MN). The exposed back surface of the mesh was then mounted on glass slides for deposition of Ti (6 nm)/silicone dioxide ($SiO_2$) (60 nm) by sputter coating (Denton Vacuum LLC, Discovery 635).

FIG. 1D shows an illustrative schematic depicting an example embodiment of a sweat biomarker sensor fabrication technique. The schematic depicts electrode fabrication based on transference of lithographically fabricated current collectors, based on polyimide layers (PI layers 142, 144) which isolate the gold current collectors (Au layer 143). Afterwards, screen-printing is performed over current collectors with silver (Ag)/silver chloride (AgCl) (Ag/AgCl layer 141) and Prussian Blue (PB layer 145). Finally, a catalyst or reactant layer 146 (e.g., enzyme layer) is dropcasted over working electrode surface.

A PDMS layer of 500 μm (Dow Corning, Sylgard 184) was spin-casted onto a glass slide with its surface treated by PMMA to reduce adhesion of the silicone. The devices were then transferred onto the PDMS through formation of covalent bonds by condensation reactions between ozone (UVO) treated Si and $SiO_2$ on the back side of the devices. The tape was then dissolved with deionized (DI) water. The devices were then ready for screen printing, as depicted in the example process (1) of FIG. 1E.

Figure 1E:
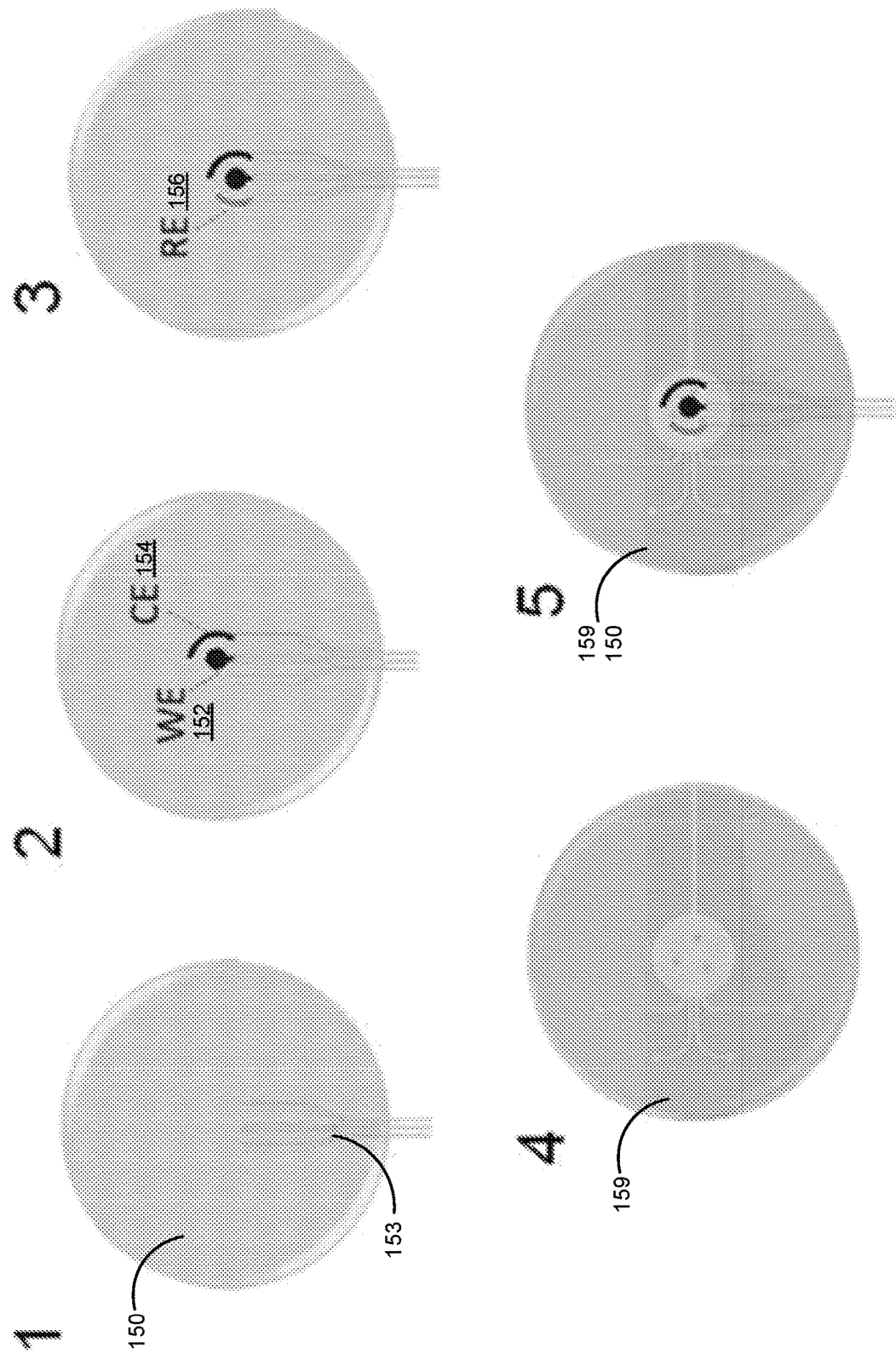
FIG. 1E shows an illustrative diagram depicting an example fabrication process of the example microfluidic-electrochemical sensor.

FIG. 1E shows an illustrative diagram depicting an example fabrication process of the example microfluidic-electrochemical sensor. The example fabrication processes include the following. (1) Current collectors 153, lithographically prepared, are transferred on a thin PDMS layer 150. (2) Working electrode (WE) 152 and counter electrode (CE) 154 are screen-printed with Prussian blue. (3) Reference electrode (RE) 156 using Ag/AgCl is screen-printing. After drop-casting deposition of the enzyme (not shown), (4) PDMS microfluidic layer 159 is fabricated and (5) bonded on top of the PDMS electrode layer 150.

Sweat biomarker levels were measured in real-time using electrochemical biosensors located inside of the microfluidic device reservoir, as shown in FIG. 1B. In the example implementations, the working, counter and reference electrodes were fabricated through screen-printing. For example, the patterns were designed in AutoCAD (Autodesk, San Rafael, CA) and outsourced for fabrication on stainless steel through-hole 12×12 in² framed stencils (Metal Etch Services, San Marcos, CA). Reference electrodes for the example sensor configurations were printed using Ag/AgCl ink (E2141 Ercon Inc., Warcham, MA) and cured at 80° C. for 10 min. For sweat lactate sensors, carbon Prussian Blue conductive ink (C2070424P2, Gwent Group, UK) was used to print the working and counter electrodes over the gold current collectors, as shown in processes (2) and (3) of FIG. 1E. The printed layer was cured at 80° C. for 10 min. Then, the electrodes were modified with the lactate recognition layer, as shown in FIG. 1D. Specifically, one μL of LOx (40 mg/mL), containing the BSA stabilizer (10 mg/mL), was mixed with 1 μL of chitosan solution (0.5 wt % in 0.1 M acetic acid) and the resulting 2 μL mixture was drop cast onto the working electrode surface. $LO_x$-modified electrodes were dried overnight at 4° C. prior to use. For sweat glucose sensors, $GO_x$ was mixed with carbon Prussian Blue ink (10,000 unit $GO_x$/mg) and then used to print the working electrodes. The printed layer was cured at 50° C. for 10 min.

A thin, flexible anisotropic conductive film (ACF) cable (Elform, USA) was bonded to the contact pads of the devices that were then bonded to Si with heat and pressure as a connection to external circuits. The other end of the cable was bonded to a custom printed circuit board, as illustrated in FIG. 1C. The top PDMS layer containing the lactate or glucose sensor was bonded with the microfluidic PDMS layer by applying UVO (7.5 min) over both surfaces.

Theoretical Simulation of Sweat Flow in Microfluidic Device

The example implementations included a theoretical simulation of sweat flow using the example microfluidic device. For example, two simulations were performed using ANSYS FLUENT© 18.1 academic. These simulations were performed to verify the flow behavior under operating conditions of the microfluidic sweat sampling device. Detailed descriptions are described below.

Two example simulations using ANSYS FLUENT 18.1 academic were carried out to verify the flow behavior under operating conditions of the microfluidic sweat sampling device. Both simulations were performed with identical flow conditions differing only by the sweat sensor placement within the reservoir for the second simulation.

The fluid flow properties were assumed to be the same as water since the composition of sweat is 99% water, and the range of sweat flow rate was 1-20 nL/min. For the length scales, two distinct lengths were used, e.g., one on the order of 300 μm (channels) and the other on the order of 5 mm (reservoir). Assuming four circular inlets 2 mm in diameter, and a sweat rate of 20 nL/min per gland, the dimensionless groups were obtained.

Example data collected indicated that a Reynolds number (Re) much less than one resulted in all device regions. Therefore, the flow was laminar throughout the device and viscous effects were important. Also, the Weber number (We) was much less than one, which indicated that surface tension forces were dominant with respect to inertial forces. The calculated Capillary numbers (Ca) showed that the surface forces were also dominant with respect to viscous forces. The flow physics were dominated by viscous and capillary effects for all device sections except for the inlets and reservoir where the Buoyancy number (Bo) was greater than one and, thus, buoyancy effects could potentially be important. Therefore, the pressure drop should be due to viscous and capillary effects and can be computed as:

Pressure Drop in a Microchannel $$\Delta p = Q \frac{12 \, \mu L}{h_0^3 w} \left[ 1 - 0.630 \frac{h_0}{w} \right]^{-1} \quad \text{(Equation 1)}$$

Capillary Pressure $$\Delta p = Q \frac{2(h+w)}{hw} \sigma \cos\theta \quad \text{(Equation 2)}$$

Equation 1 and Equation 2 show that the pressure drop increases upon decreasing the microchannel cross section, but increasing the channel cross-sectional area also increases its volume and the time to fill the system. In order to define the channel dimensions necessary to find an adequate trade-off between pressure drop and system volume, a channel width larger than 100 μm to avoid high pressure drops. Also, to reduce evaporation, a width not greater than 200 μm was used.

The example simulations were performed considering laminar flow as the Reynolds number was calculated to be lower than 1. The geometry was specified according to section the finalized microfluidic design. The flow rate was specified from the inlet velocity set as 1.06 µm/s to match experimental (0.8 µL/min) and the outlet condition adopted was zero gauge pressure.

The first example simulation was performed in half domain to take advantage of the design symmetry, but the second simulation needed to be performed using the complete geometry as the insertion of the electrode modified the flow field in a non-symmetric fashion.

Figure 1F:
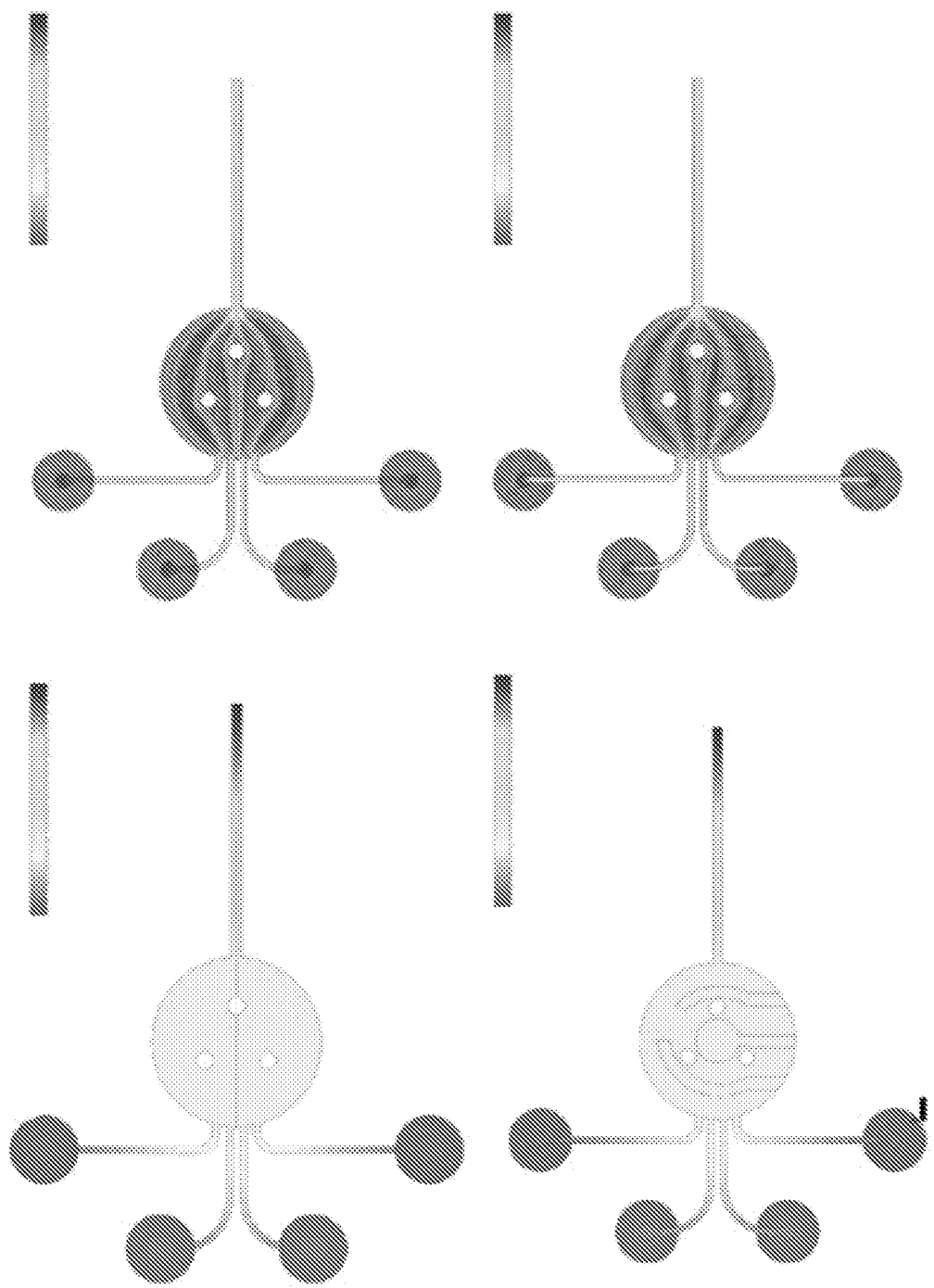
FIG. 1F shows a simulated fluid flow profiles within an example microfluidic system.

FIG. 1F shows a simulated fluid flow profiles within an example microfluidic system, showing a velocity contour at the microchannel network mid plane and streamlines originating from inlet; and a pressure contour at the microchannel network mid plane. Systems (i) without and (ii) with electrode. FIG. 1F shows that the velocity fields were also not affected by the electrode presence within the reservoir. The velocity contour at the channel mid plane as well as the streamlines were very similar for both cases indicating that the flow field was not disturbed by the electrode. The streamlines also showed there was no mixing as was expected of a very low Reynolds number (Re<1). This characteristic defined the locations of the reservoir inlets and outlets, (i.e. they must be placed on opposite sides). The streamline distribution also revealed that the fluid from the outer inlets flowed close to the walls and had a small intersection with the sensor surface, however, the flow from the innermost inlets intersected a large area of the electrode surface. These observed behaviors may be useful for further optimization of microfluidics devices with additional studies and simulations of transient states as well as multi-physics analysis are necessary for the design and optimization of more complex microfluidic systems.

As shown later in FIG. 2D, the diagrams show that the static pressure was not affected by the presence of the electrode within the reservoir. It is important to note that the pressure loss due to viscous effects (laminar regime) was very low (0.499 pascals (Pa)) compared with the maximum physiological eccrine gland pressure (72 kilopascals (kPa)). Also, from FIG. 1F, one can see that the pressure inside the reservoir was constant at approximately 0.375 Pa, which caused small deformations even for a low stiffness system as is required for a device compatible with skin mechanical properties.

Example In-Vitro Electrochemical Characterization: Flow Injection Analysis in Microfluidic System Example implementations including electrochemical characterization of LOX- and GOX-modified Prussian Blue electrodes were performed under flow injection analysis (FIA) in the microfluidic system. For example, a 403U/VM2 pump (Watson-Marlow Bredel Pumps, MA, USA) allowed the pumping of artificial sweat composed of various electrolytes (sodium chloride (NaCl), sodium sulfate ($Na_2SO_4$), sodium $NaHCO_3$, potassium chloride (KCl), magnesium chloride hexahydrate ($MgCl_2 \cdot 6H_2O$), monosodium phosphate ($NaH_2PO_4$), calcium carbonate ($CaCO_3$), and ammonium hydroxide ($NH_4OH$)) to the microfluidic device at 200 µL/min. Varying concentrations of lactate (4 to 20 mM with 4 mM increments) and glucose (2 to 10 mM with 2 mM increments) were injected with a 6 port Rheodyne 7000 valve (IDEX Health & Science LLC, CA, USA) containing a 20 µL sample loop. Due to the limitations in mimicking the low flow rate of on-body sweat conditions, slow flow injection experiments were carried out at 20 µL/min with varying concentrations of lactate and glucose from 0.2 to 1 mM with 0.2 mM increments. During this flow injection analysis, only one inlet was used for continuous pumping, with the microfluidic device filled initially with artificial sweat, responding instantaneously to the passage of the injected sample-metabolite zone.

Example On-Body Operation with Human Subjects

Epidermal evaluation on human subjects was conducted in strict compliance following a protocol approved by the institutional review board (IRB) at the University of California, San Diego. Two healthy volunteers were recruited for on-body evaluation of the developed sensors. The on-body study was conducted as a set of two trials: device evaluation and sensor evaluation. For the first set of on-body studies, a bare electrode transducer (without the immobilized enzyme) was used to evaluate the selectivity of the sensor and discrimination against non-target sweat constituents. The example microfluidic system was attached to the skin using a 3M Double Coated Medical Tape (#1522) (Maplewood, MN, USA) with 2 mm opening aligned with the 0.5 mm inlets of the device. Next, 0.5 µL of blue food dye was placed on each sweat collection area and the device was then transferred to the lower back of the volunteers having been previously cleaned with rubbing alcohol. For easy complexion on the skin of the flexible electronics, a (30:1 base-curing agent) flexible 45×6 cm2 PDMS bandage was prepared for location on the arm and 3M transparent film Tegadem (#16004) (Maplewood, MN, USA) was used for mounting on the back of the subject. After location of the device, the volunteer was asked to perform physical exercise on a stationary bike (Sunny Health & Fitness SF-B1002C Chain Drive Indoor Cycling Bike, Los Angeles, CA) for 20 min. Exercise biking conditions were kept at high intensity and constant speed and temperature (24° C.) to get comparable results. The times to fill the inlets, reservoir and outlet were recorded in order to assess the sweat flow during exercise and to evaluate the structural properties of the device. In the second trial, a glucose or lactate sensor incorporated onto the inside of the PDMS top layer was connected to a personalized printed circuit board (PCB) with amperometric and Bluetooth® capabilities through FID cables, e.g., as shown in FIG. 1C. The sweat biomarker signal was recorded in real-time during 2000 seconds(s) of exercise (considering 0 s when the subject starts exercising) using a laptop and a homemade system control developed in Matlab. The times to fill the inlets, reservoir and outlet were also recorded to evaluate the influence of the electrode presence within the chamber. A fast current response was observed as soon as the metabolite-containing sweat reaches the detector. All example on-body experiments were carried out with device outlet facing upward as contributions from gravity forces during sensing reservoir filling were found to be negligible.

Example Results of Example Implementations

The example soft material-based wearable microfluidic electrochemical sensor device used in the example implementations included lithographically and screen-printed electrochemical sensors integrated in a microfluidic device for real-time sweat sampling and monitoring of target biomarkers.

The example device includes three circular, flexible layers (e.g., 2 cm diameter) offering skin conformity due to the inherent flexibility of PDMS, similar to the shape shown for the example device 100 in FIG. 1A. The example device included a top 500 µm PDMS-layer with the integrated electrodes (e.g., first flexible layer 110); a 500 µm-thick PDMS-base layer with four inlets and corresponding 300 µm height microfluidic channels directed to a 5 mm circular reservoir ending in an outlet opening (e.g., second flexible layer 120). The example device was applied to the skin using a medical-grade double-sided adhesive layer (e.g., adhesive layer 130), which leads to strong attachment of the device with the underlying skin. The non-porous adhesive layer included four 2 mm diameter openings matching with the four 700 µm sweat collection inlets of the microfluidic PDMS layer.

The prevalence of sweat glands across the body makes our skin a natural sweat pumping machine during exercise or heating periods. Thus, the adhesion of a microfluidic device to the skin serves to capture freshly generated sweat to fill the microchannel network and detection reservoir containing the sensing electrodes. Such sweat uptake is driven by natural sweat gland pressures created by an osmolality difference between plasma and sweat, as well as capillary forces. Certainly, some of the sweat pores in contact with the adhesive were occluded, influencing the final sweat rate. However, the sweat pores located within the 2 mm diameter openings of the adhesive layer naturally pump generated sweat through the PDMS-based microfluidic device due to the short distance between the inlet of the microfluidic device and the sweat pore, considering the 100 µm thickness of the adhesive used as the adhesive layer 130 in the example implementations. The fresh sweat is then, continuously wetting the microfluidic channels to rapidly reach and fill the detection reservoir. The 5 mm diameter detection reservoir included a top PDMS layer with incorporated sensing electrodes and a bottom PDMS layer with three equidistant 200 µm diameter pillars. One example function of these pillars was to maintain the structural stability of the sensing reservoir, avoiding collapse of the electrode layer. The absence of pillars could result in decreased volume of the reservoir, changing the reproducibility of both the reservoir volume and the working area available for the detection reactions, as shown in FIG. 1G.

Figure 1G:
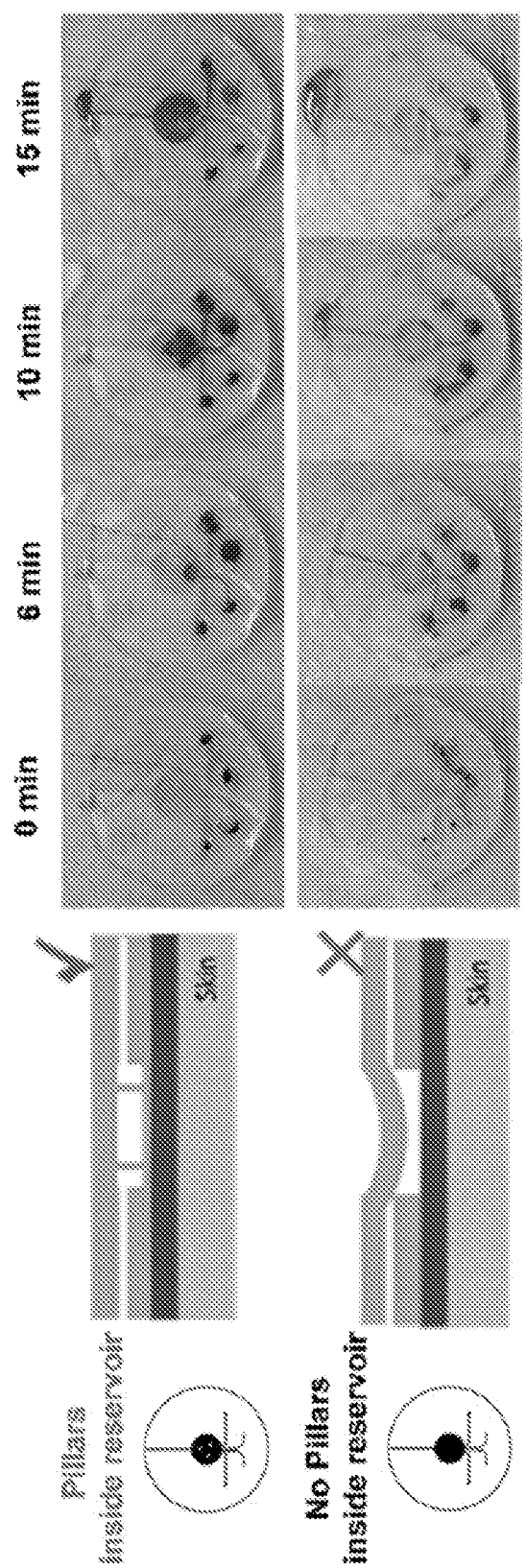
FIG. 1G shows images and an illustration depicting the impact of the example micropillars on device operation in an example microfluidic device.

FIG. 1G shows images and an illustration depicting the impact of the example micropillars on device operation in an example microfluidic device. In the example of FIG. 1G, the impact on reservoir volume and fluid flow profile for an example device with inclusion of micropillars within the reservoir (top row of illustrations and images) is shown, and the impact on the reservoir volume and fluid flow profile for an example device without micropillars within reservoir (bottom row of illustrations and images) is shown.

In the example implementations, due to the necessity of maintaining mechanical compatibility with the skin, a flexible PDMS (30:1 base/curing-agent ratio) was used. However, in these examples, due the disadvantages of reservoir collapsing as a result of the large reservoir diameter compared to the thin dimensions of the top PDMS layer, two procedures to increase structural stability. These methods included the incorporation of micropillars within the reservoir to increase the stiffness locally and the use of a 50 µm rigid PDMS (10:1 base/curing-agent ratio) to increase the Young's modulus of the microfluidic features, thereby increasing the stiffness into the channels. Finally, the sweat was driven to an outlet (200 µm wide by 300 µm height), which allowed continuous replenishment of the sweat fluid and minimized back pressure.

The example three-electrode sensing system used in the example implementations was based on lithographically-fabricated and Au-based current collectors with screen-printed Prussian Blue working and counter electrodes, along with Ag/AgCl as a reference electrode (FIG. 1D, and FIG. 1E). The working electrode transducer was modified with the corresponding oxidase enzyme layer to impart the desired selectively toward the target analyte (FIG. 1C). The generation of hydrogen peroxide by the glucose or lactate enzymatic reactions was monitored amperometrically. A flexible printed circuit board (PCB) Bluetooth® controller, integrated with the electrochemical detector, enabled real-time wireless transmission of the data to a laptop (FIG. 1C).

The time required for filling the detector reservoir filling must be minimized to realize real-time monitoring and to measure temporal changes in sweat biomarker levels. Consequently, the dimensions of the microfluidic network were determined through theoretical calculations.

FIGS. 2A-2C show data plots and images depicting the example theoretical simulation and experimental verification results of required time to fill microfluidic reservoir. FIG. 2A shows example simulated plot of time required to fill microfluidic reservoir with varying number of inlets (e.g., inset: scheme of microfluidic configuration used). FIG. 2B shows photographs of the time required to fill designed microfluidic reservoir using optimized four-inlet design with sweat generated through exercise. FIG. 2C shows time lapses (e.g., obtained from video recordings) after 0, 7, 10 and 13 min of exercise using the optimized four-inlet design, including the following: row (i) shows theoretical simulation in the microfluidic system, and experimental data; row (ii) shows images of an example device without electrodes; and row (iii) shows images of an example device with electrodes in the detection reservoir. Blue food coloring was placed at each inlet prior to on-body application. Scale bar, 5 mm.

The most underlying layer of the soft microfluidic sensing system was a medical adhesive, attached directly to the epidermis with 2 mm diameter openings designed for sweat harvesting (layer iii, FIG. 1A). The openings isolated roughly four sweat glands when applied and confined to the lower back (containing 132 glands/cm$^2$) to collect sweat fluid and preventing lateral flow of sweat from other locations. The final design of the microfluidic device was optimized through mathematical modelling of the fluid flow within each portion of the device, assuming fluid properties of water and a sweat rate of 20 nL/min per gland.

Careful consideration was given to the layout of the microchannel network, and in particular, to the detection reservoir size and to the number of inlets necessary for achieving its rapid filling. The design of the reservoir was constrained by the dimensions of the enclosed sensing electrodes, as depicted in FIG. 1B. Thus, a 5 mm diameter detection reservoir allowed convenient placement of the sensor along with minimal dead volume. Once the dimensions of the inlet, outlet, channels and sensing reservoir were defined, the number of inlets was optimized. Increasing the number of inlets increases the area used to collect sweat and the total system volume. The time to fill the device was theoretically calculated using different numbers of inlets, shown in FIG. 2A. While a single inlet would require more than 30 min to fill the entire device, this time decreased significantly upon increasing the number of inlets to a maximum of six. At greater than six inlets, a plateau of ~8 min filling time was reached, indicating that the increased area of enclosed sweat pores did not compensate the larger volume of the microchannel network. In the example final microfluidic device, four inlets were selected to use (FIG. 2A, inset) as a greater number of inlets promoted mechanical instability of the adhesive layer due to the close proximity of openings, which could cause sweat leakage. The four-inlet configuration allowed rapid sweat sampling without greatly increasing system volume, and hence led to a short reservoir filling time.

FIG. 2B displays time-lapse analysis of the sweat flow profile within the microfluidic device applied to the lower back of a healthy volunteer during exercise activity (in the absence of sensing electrodes). For example, since the temperature and exercise conditions can change the sweat rate and, consequently the filling time of the detection reservoir, identical conditions were maintained between trials. The example data shown in FIGS. 2A-2C was obtained under intense and constant cycling conditions at constant room temperature (e.g., 24° C.). The dried blue dye, drop-cast into each inlet (e.g., time lapse at 0 min) began to dissolve at the start of sweat flow (e.g., time lapse at 6 min). The presence of micropillars within the sensing reservoir decreased the void volume and caused the sweat to fill the reservoir in a specific defined pattern. The flow grew radially through the center of the reservoir (e.g., time lapse at 7, 8 and 10 min), as was theoretically predicted in the streamline pattern and model of sweat filling air channels, shown in FIG. 2C, panel i, and FIG. 1F). After 12 min, the sensing chamber was completely filled, and as predicted in the theoretical calculations for the 4 inlet system (FIG. 2A), the sweat reached the outlet within less than 15 min. Considering the total empty (void) volume of the example device (e.g., 8.72 µL) and the time to complete reservoir filling (e.g., 13.4 min), the actual sweat flow rate was experimentally estimated to be 0.66 µL/min; e.g., assuming 4 sweat pores in each inlet, the minimum flow rate per gland was estimated to be 0.04 µL/min. Simulation of two phase sweat/air filling of the device (FIG. 2C, panel i, and FIG. 1F) showed accordance with experimental time-lapses in absence of electrodes within the reservoir (FIG. 2C, panel ii). The observed filling time was a significant improvement relative to previous reports on epidermal sweat sampling platforms. Specifically, the example system in accordance with the present technology demonstrated more than 2-fold improvement over conventional sweat monitoring microfluidic devices, which showed filling times ranging between 18 min and 3.2 h.

After judiciously designing of the PDMS microfluidic device for the sweat sampling and analysis, the overall effect of the electrochemical sensor (present in the detection reservoir) on the sweat flow was analyzed. The printed electrode acted as a physical barrier to fluid flow, changing the flux profile. Without the sensor, the flow was only disturbed by the presence of the micropillars (FIG. 2C, panels i and ii). With the inclusion of the sensing electrodes within the detection reservoir, the flow deviated around the walls of the reservoir to the center of the chamber (FIG. 2C, panel iii and FIG. 2D). Identical behavior was observed when a potential was applied to the sensor (FIG. 2D). The presence of the electrode decreased also the time to fill the reservoir. The total empty volume of the device decreased by 5.5% (from 8.72 to 8.24 µL), when considering the electrode dimensions. Furthermore, it is worth noting that in the presence of electrodes, the replacement of the sweat started at 13 min (see dilution of the blue dye, FIG. 2C), while without the electrodes the entire device was still filling. In agreement with the experimental data, the simulated flow profile demonstrated that the flexible microchip design allowed a constant fluid replacement.

Figure 2D:
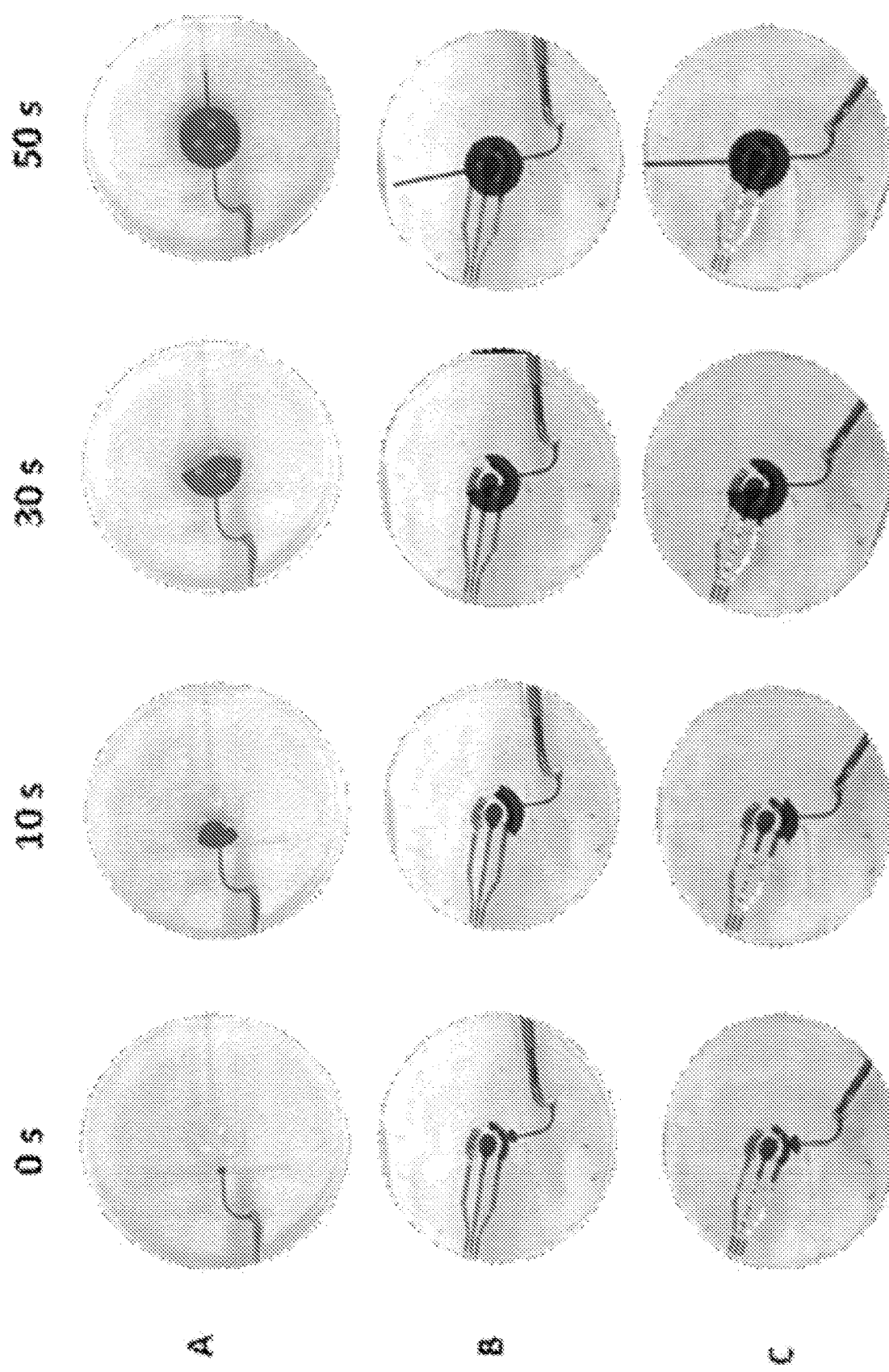
FIG. 2D shows an example evaluation of reservoir filling of the example device.

FIG. 2D shows an example evaluation of reservoir filling of the example device. FIG. 2D shows a filling profile of the microfluidic electrochemical sensor system under flow conditions (20 µL/min), in absence of electrode (panel A), in presence of electrode (panel B), and in presence of electrode with an applied potential of −0.1 V vs Ag/AgCl (panel C). Blue dye was used for following the water/air interface.

In order for this example microfluidic electrochemical sensing system to efficiently operate as a wearable epidermal device, the conformity to physiologic substrates is essential. For this reason, the influence of mechanical strain permutations upon the integrity of the example device was examined. For example, the example lithographically-fabricated PDMS-based device exhibited resilient mechanical characteristics under repeated cycles of bending and stretching using physiologically relevant conditions.

Figure 3A:
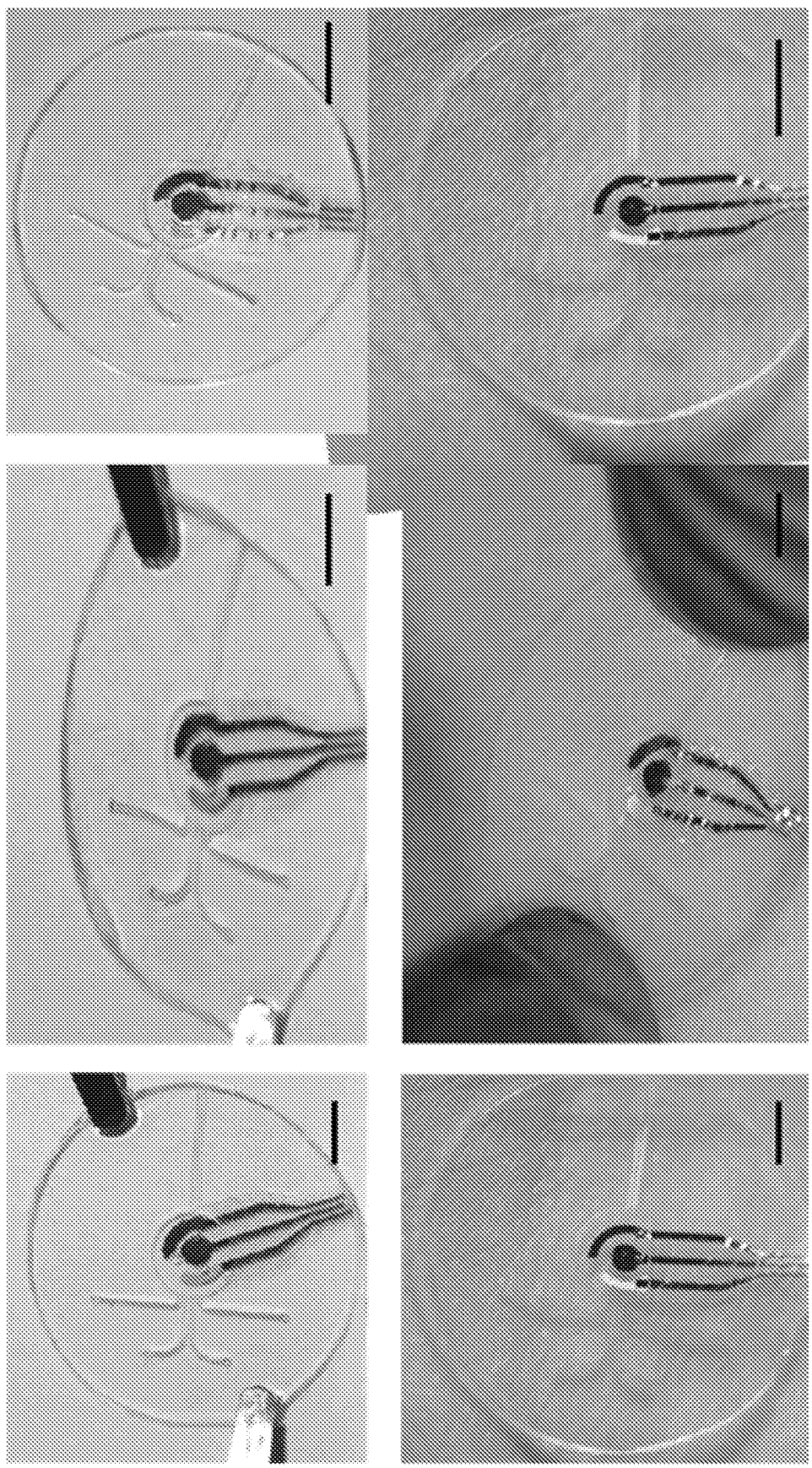
FIG. 3A shows images depicting the physical integrity analysis of an example microfluidic platform in accordance with the present technology.

FIG. 3A shows images depicting the physical integrity analysis of an example microfluidic platform in accordance with the present technology. The physical integrity analysis images of the example microfluidic system with incorporated electrodes (i) before, (ii) during and (iii) after 20 repeated cycles of 20% stretching in-vitro (A) and on the body (B). Scale bar, 5 mm.

Figure 3B:
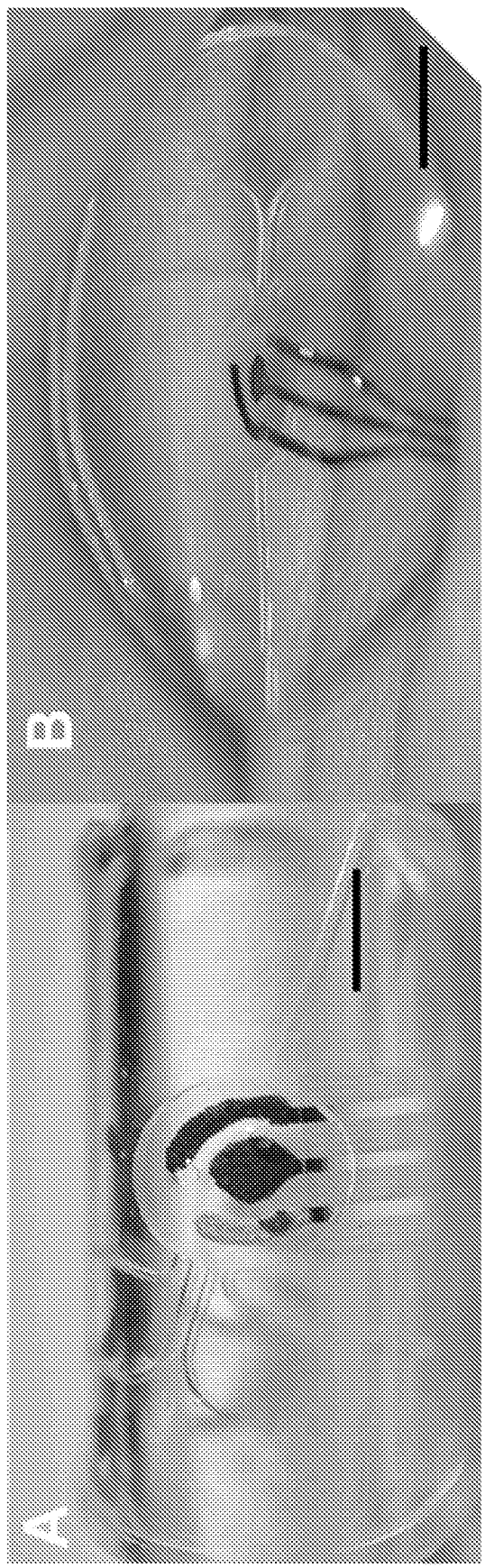
FIG. 3B shows images providing a depiction of the example microfluidic device conformity.

Indeed, the physical appearance and electrode connectivity of the microfluidic platform showed no apparent change after repeated 20 cycles of 20% stretching in-vitro (FIG. 3A, panel A) or on-body (FIG. 3A, panel B). The physical integrity and resiliency of the device were further confirmed through repeated cycles of 180 degree bending, with similarly no change observed, as shown in FIG. 3B. These attractive mechanical characteristics promoted facile application as an on-body continuous sweat analyte monitoring device, without concern of functional loss during operation.

FIG. 3B shows images providing a depiction of the example microfluidic device conformity. Photographs of the bending of the microfluidic device are shown for the example device (A) in-vitro and (B) on the skin.

Example results of in-vitro characterization of the example microchip electrochemical biosensors are described.

Figure 4A:
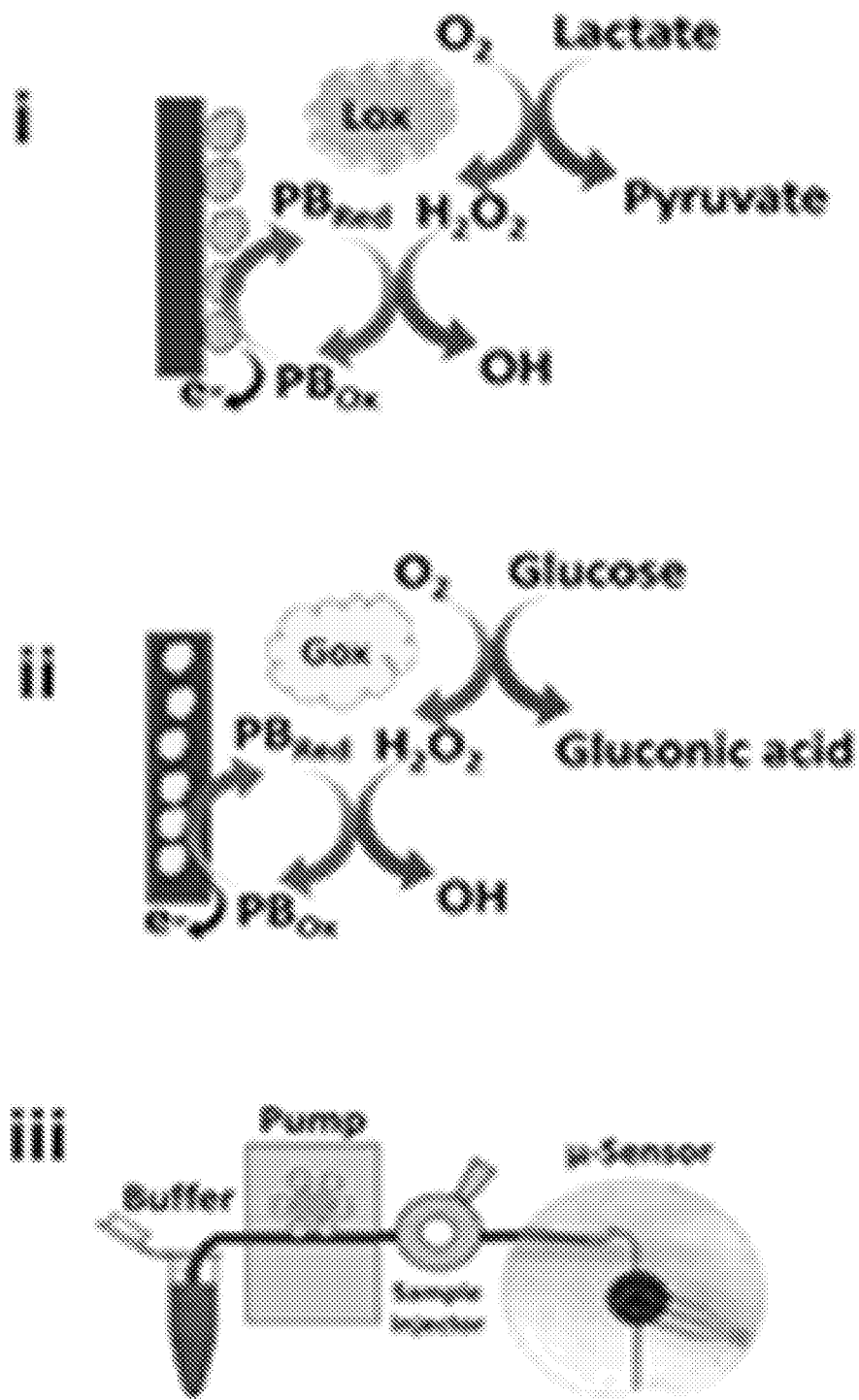
FIGS. 4A-4C show illustrative diagrams and data plots depicting flow injection analysis in an example soft microfluidic device in accordance with the present technology.
Figure 4C:
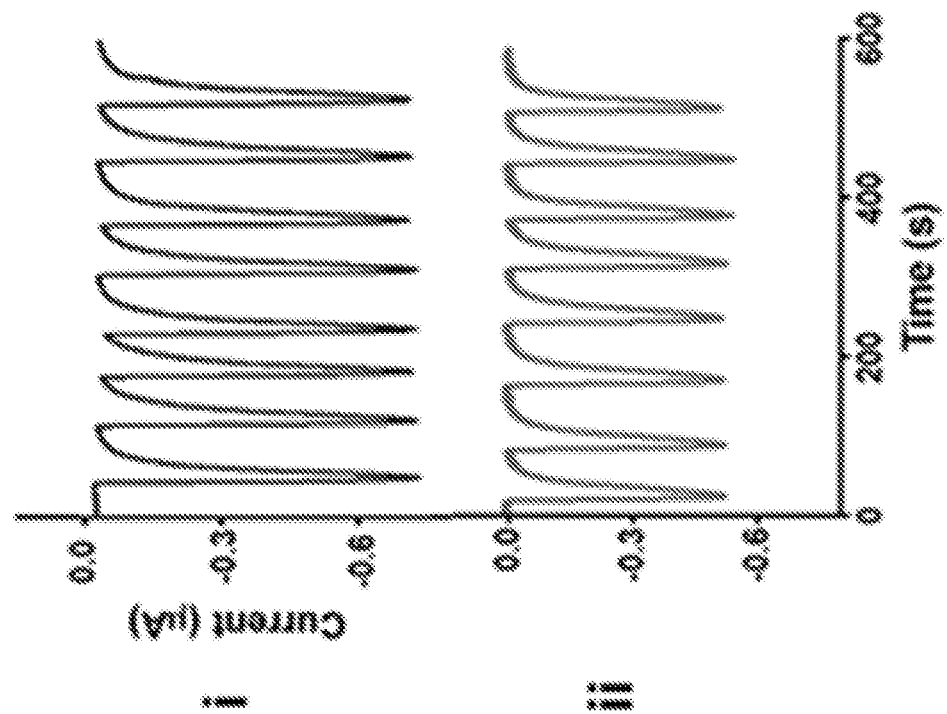
Figure 4B:
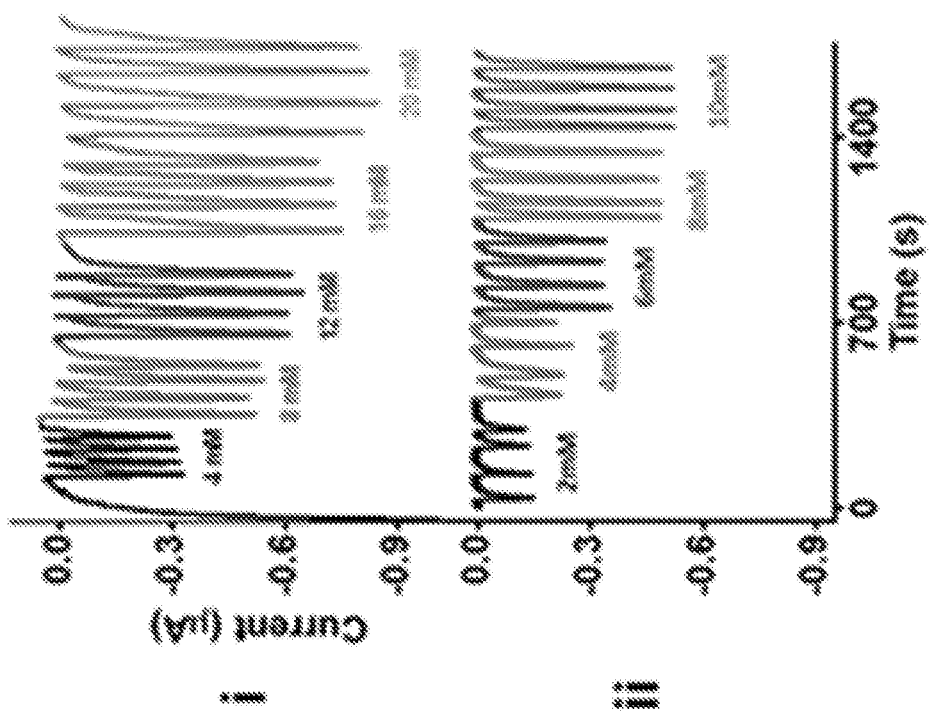

FIGS. 4A-4C show illustrative diagrams and data plots depicting flow injection analysis in an example soft microfluidic device in accordance with the present technology. FIG. 4A shows a schematic representation of enzyme-based electrochemical biosensing mechanisms for (i) lactate and (ii) glucose. FIG. 4A, panel iii shows a schematic of the flow injection analysis system. FIG. 4B shows a data plot depicting the amperometric response for (i) 4, 8, 12, 16 and 20 mM lactate and (ii) 2, 4, 6, 8 and 10 mM glucose at the Prussian Blue-enzyme-modified electrode. FIG. 4C shows a data plot depicting the reproducibility of the response for (i) 12 mM lactate and (ii) 10 mM glucose solutions. In the example implementations, the applied potential was-0.10V (vs. Ag/AgCl), and the artificial sweat was pumped at 200 L/min.

The analytical performance of LOX- and GOX-modified Prussian Blue electrodes was evaluated first using FIA with amperometric detection in connection to the flexible electronic interface (FIG. 4A, iii). For example, such detection was achieved through enzymatic oxidation of the target analytes coupled with electrochemical monitoring of the hydrogen peroxide product at Prussian Blue-modified screen-printed electrode transducers (FIG. 4A). Artificial sweat was pumped at 200 µL/min to the microfluidic system. In the initial evaluation of the LOX-modified electrode, four consecutive 20 µL injections of lactate solutions of increasing concentrations (from 4 to 20 mM) in artificial sweat were monitored under potentiostatic conditions at −0.1 V vs. Ag/AgCl (FIG. 4B, panel i). These microfluidic biosensor displays well-defined peak currents that increase linearly with the lactate concentration, with the corresponding calibration plot displaying good sensitivity (29.6 µM/µA) and linearity ($R^2$ 0.98). Repeated injections of 12 mM lactate (n=8) showed a low RSD of 1.2%, indicating reproducible flow profile and stable LOX-based electrode (FIG. 4C, panel i). Similar flow-injection microchip studies were performed for glucose biosensing (FIG. 4B, panel ii). Evaluation of the response of the GOX-based detector to varying glucose concentrations (from 2 to 10 mM) in artificial sweat under potentiostatic conditions (at −0.1 V) shows a highly linear concentration dependence ($R^2$ 0.99). The precision for glucose detection was estimated from repeated injections of 10 mM glucose (n=8) which yielded a RSD of 1.6% (FIG. 4C, panel ii). Both the glucose and lactate microchip detectors display fast response time and rapid return to the baseline, with no carry over between successive samples. The latter confirms the absence of mixing and reflects the facile sample removal from the detector compartment. Slow pumping conditions (20 μL/min), mimicking the low flow rate of the on-body sweat analysis, were also examined at a low glucose concentration expected in sweat, indicating a favorable limit of detection of 50 μM, shown in FIG. 4D. Overall, the well-defined current response of both the example lactate and glucose biosensors indicated a good performance of the example microchip detectors and of the integrated supporting miniaturized electronics over physiologically relevant concentration ranges. Flow injection operation is expected to offer pre-calibration of the wearable microfluidic biosensor prior to the on-body operation, as desired for quantitative analysis. This may require adjusting and compensating the sensor response to variations in temperature, e.g., flow rate and pH.

Figure 4D:
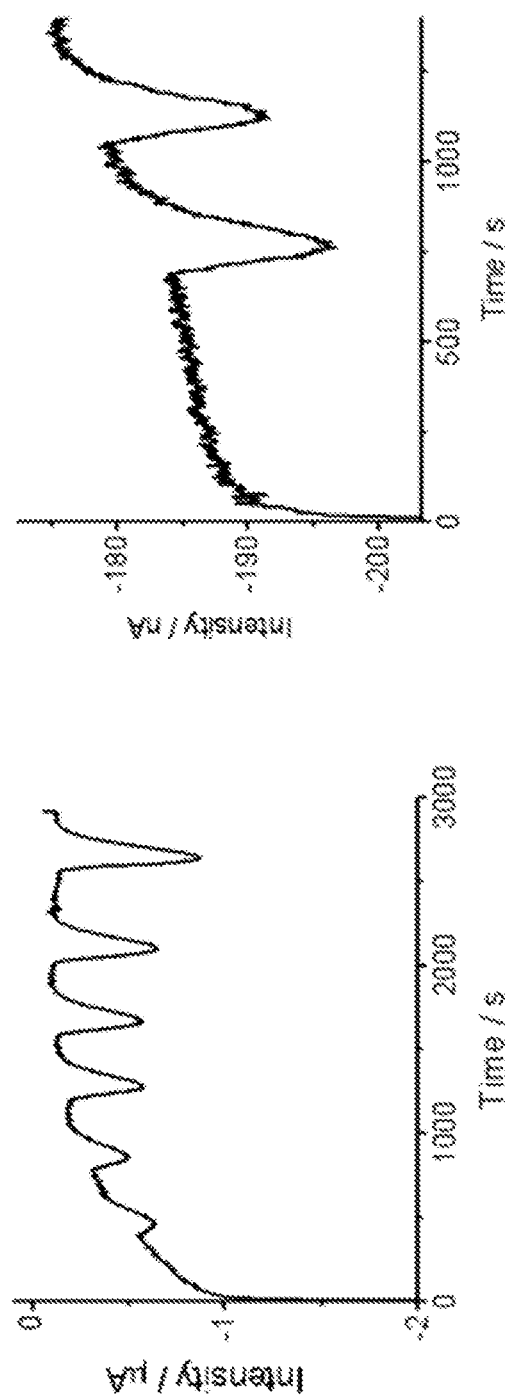
FIG. 4D shows data plots showing example low flow rate detection of sweat metabolites.

FIG. 4D shows data plots showing example low flow rate detection of sweat metabolites. Flow injection analysis under slow injection conditions (20 μL/min) included: (A) Glucose detection profile (i) calibration curve and (ii) minimum detected concentration (50 μM).

Example results of sweat monitoring with human subjects with the example integrated wireless electronics are described.

Figures 5A, 5B, 5C, 5D:
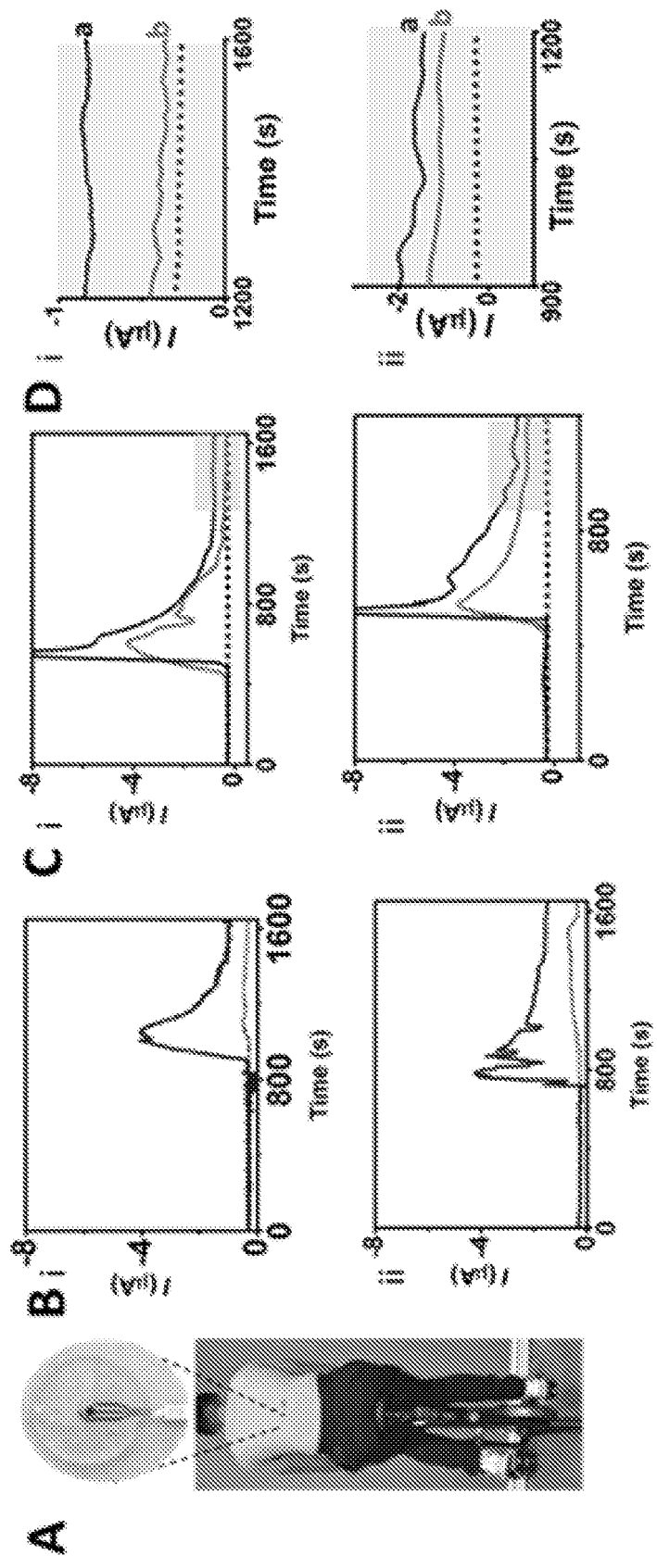
FIGS. 5A-5D shows example data from an example real-time on-body amperometric response for sweat metabolites using an example flexible epidermal microfluidic device in accordance with the present technology.

FIGS. 5A-5D shows example data from an example real-time on-body amperometric response for sweat metabolites using an example flexible epidermal microfluidic device in accordance with the present technology. FIG. 5A shows an image depiction of on-body device configuration applied to the lower back of the subject during trials. FIG. 5B shows a data plot of continuous lactate monitoring with LOX-modified electrode (blue full line) and control (LOX-free) electrode (dotted line) for (i) subject 1 and (ii) subject 2. FIG. 5C shows a data plot of continuous glucose sensing analysis with GOX-modified electrode before meal (red full line) and after meal (black full line), as well as control without GOX-modification (dotted line) for (i) subject 1 and (ii) subject 2. FIG. 5D shows data plots, zoomed, of steady-state current response from FIG. 5C the GOX-modified detector before meal (b, red full line) and after meal (a, black full line), as well as control without the GOX-modification (c, dotted line) for (i) subject 1and (ii) subject 2 during 900-1200 s. The example amperometric experiments were carried out by applying −0.1 V (vs. Ag/AgCl) during physical exercise on a stationary bicycle and data wirelessly transmitted to a computer.

On-body real-time monitoring of sweat lactate and glucose levels was performed to test the example soft microfluidic device in practical scenarios using two healthy human subjects in compliance with the UCSD-approved IRB protocol. Temporal changes in sweat lactate and glucose levels were measured over time, during ~20 min of indoor fitness cycling (FIG. 5A). The continuous monitoring of the amperometric sweat lactate response from the two subjects with the LOX-modified flow detector, showed a sharp increase of the current signal as the sweat sample enters and fills the detector reservoir (FIG. 5B, panel i and FIG. 5B, panel ii). In all cases for the example on body monitoring implementations, negligible faradaic currents were observed at the initial period of exercise, varying from 750 to 850 s, reflecting the delayed sweat filling process and the different sweat rates of the subjects. A rapid increase in the current response is observed as soon as the reservoir is filled, and the lactate-containing sweat reaches the detector. Sharp current spikes (e.g., ~4 μA for both subjects) were observed for both subjects upon complete filling of the reservoir, with the signals reflecting temporal sweat lactate levels to provide the real-time fitness profile of the subjects (FIG. 5B, panel i and FIG. 5B, panel ii). The largely different current signals (e.g., as compared to the FIA operation of FIG. 4) reflect the combination of various factors that affect the amperometric response, including largely different flow rates, temperature and pH. As expected for physical exertion, the lactate signal increased significantly during such intensive exercise activity and decreased at extended periods, leading to dynamic lactate profile toward individual fitness monitoring. For example, different lactate profiles reflect differences in the fitness level, particular muscular fatigue among such individuals. The selectivity of the lactate biosensor toward sweat lactate detection was validated by concurrent measurements using an "enzyme-free" control biosensor. Negligible current signals were observed during the entire exercise period without the LOx-modification (FIG. 5B, panel i and FIG. 5B, panel ii, dotted lines), e.g., confirming that the response of the LOx-modified biosensor was solely from the presence of sweat lactate and not from other sweat constituents. For example, such remarkable selectivity reflects the coupling of the specific enzymatic reaction with the selective amperometric transduction at the Prussian Blue transducer.

Similarly, sweat glucose levels were continuously monitored during exercise using GOX-modified electrodes in two healthy subjects (FIG. 5C, panel i and FIG. 5C, panel ii). Two sets of sweat glucose monitoring experiments were carried out for each subject: before meal (red line) and after a meal (black line) using the enzyme-modified electrodes to probe the capability of our microfluidic system of distinguishing temporal changes in sweat glucose levels. Similar to lactate trials, a sharp increase in the detected amperometric current is observed (e.g., ~−8 μA) upon reservoir filling (e.g., at 800 and 500 s, for subjects A and B, respectively), due to closing of the electrochemical circuit by sweat. The greater magnitude of the initial increase in current response, relative to that observed with lactate sensors (e.g., despite the lower sweat glucose levels relative to lactate), is attributed to surface or residual glucose levels. As such contaminating glucose concentrations are present not only on the skin surface, but also within the skin sweat ducts and sweat pores prior to continuous fresh sweat generation, the ability of the microfluidic device for rapid removal and replacement of contaminated sweat is crucial to the development of accurate glucose monitoring in sweat. This result highlighted also the necessity for extensive skin cleaning procedures prior to sweat glucose sensing. Hence, device application sites were thoroughly cleaned with rubbing alcohol prior to attachment in each trial. In previously reported sweat collection systems, data obtained over an initial time period (e.g., ~10 min) were omitted from reports due to related surface contamination findings. In the example study, here we relied on the amperometric glucose response after contaminated sweat was removed (passed through the detector) upon continued cycling (FIG. 5D, panel i and FIG. 5D, panel ii). Analytically useful glucose data could thus be obtained using the microfluidic device 15-20 min after initial filling of the detection chamber, reflecting the arrival of fresh sweat and hence the actual physiological glucose levels (FIG. 5D). These delayed data (FIG. 5C, highlighted zoomed area) show clear differences in the response before and after a meal (FIG. 5D, panel b vs panel a, respectively). This demonstration of rapid sweat sampling and replacement with fresh sample represents an improvement compared to slow device filling rates of previous systems. These results indicated distinct changes in the current response when glucose concentration varied in the subjects and before and after a meal. The trend of the microfluidic electrochemical glucose sweat was in agreement with these blood glucose values (not shown). Evaluation of the on-body selectivity of the microfluidic device was performed by using a GOx-free transducer. The data confirmed that the observed current was solely the result of the glucose enzymatic glucose detection and not due to other sweat constituents (FIG. 5D, panel i and FIG. 5D, panel ii, dotted line). Note also the absence of the large initial glucose (contamination-related) response in enzyme-free trials. Overall, the example results shown in FIGS. 5A-5D illustrate the potential of the epidermal microfluidic biosensors to provide temporal evaluation of sweat biomarker concentrations during continuous and non-invasive fitness and health monitoring. For the example used in the experiment, the on-body sensing should be coupled with a pre- and/or post-calibration of the detector to facilitate the quantitation process in connection to a FIA operation.

The example implementations have demonstrated a new skin-mounted microanalytical flow system, integrating a soft sweat sampling microfluidic system with microfabricated electrochemical flow detectors for continuous real-time monitoring of sweat metabolites. Theoretical modelling was shown for optimization of the microchannel layout towards fast sweat flow rate and short device filling time. The example device was shown to endure repetitive mechanical deformations experienced by the epidermis. Combined with small and flexible printed electronic (e.g., potentiostatic) circuitry for controlling the entire operation and wireless real-time collection of data, the example soft device provides selective monitoring of sweat glucose and lactate during cycling exercise. On-body evaluations with volunteer subjects illustrated the attractive on-body electrochemical flow detection capabilities in a variety of sweating conditions. Such new capabilities address the sweat mixing and carry-over challenges of common skin-worn chemical sensors. The lightness of the entire device and the continuous sweat flow and replenishment during exercise could facilitate both short and long-term fitness studies. The new skin-conforming microfluidic chemical sensing system can be readily expanded to the real-time non-invasive monitoring of other sweat biomarkers, e.g., paving the way for a new generation of soft electrochemical wearable microfluidic systems, combining natural sampling and continuous monitoring, for healthcare and fitness applications.

In some example applications, for example, the lightness of the entire device and the continuous replacement of sweat during exercise could facilitate both short and long-term fitness and medical studies which provide meaningful clinical data. Configuration as a biofuel cell further provides useful medical or fitness applications for the powering of small wearable devices. Additionally, this device enables possible real-time monitoring of additional target molecules for clinical diagnostics and fitness applications in sweat, electrolytes such as sodium, chlorides, potassium and calcium; metabolites such as lactate, creatinine, glucose and uric acid or other small biomarker molecules. Non-invasive detection technologies via sweat offer a promising avenue for diabetic patients, one can constantly monitor his/her blood sugar level during exercise by means of this technology. The device can be integrated with a wireless communication device, such as Bluetooth® or NFC (near field communication) technology, to enable easy access and tracking to data given by the sensors. Data can be obtained by a smartphone app. Uploading to cloud will also alert a primary care physician, if an individual is not within the recommended blood glucose level. His or her primary care physician can discuss eating and exercise habits to the patient on their next encounter. One can also compare through the cloud, his or her level of fitness with other users and see where he or she stands. This can additionally provide a benchmark to set goals for future fitness level. The app can also suggest an individual to reduce his or her consumption of products that are high in sugar based on a feedback mechanism from a given fitness level data.

Figure 6:
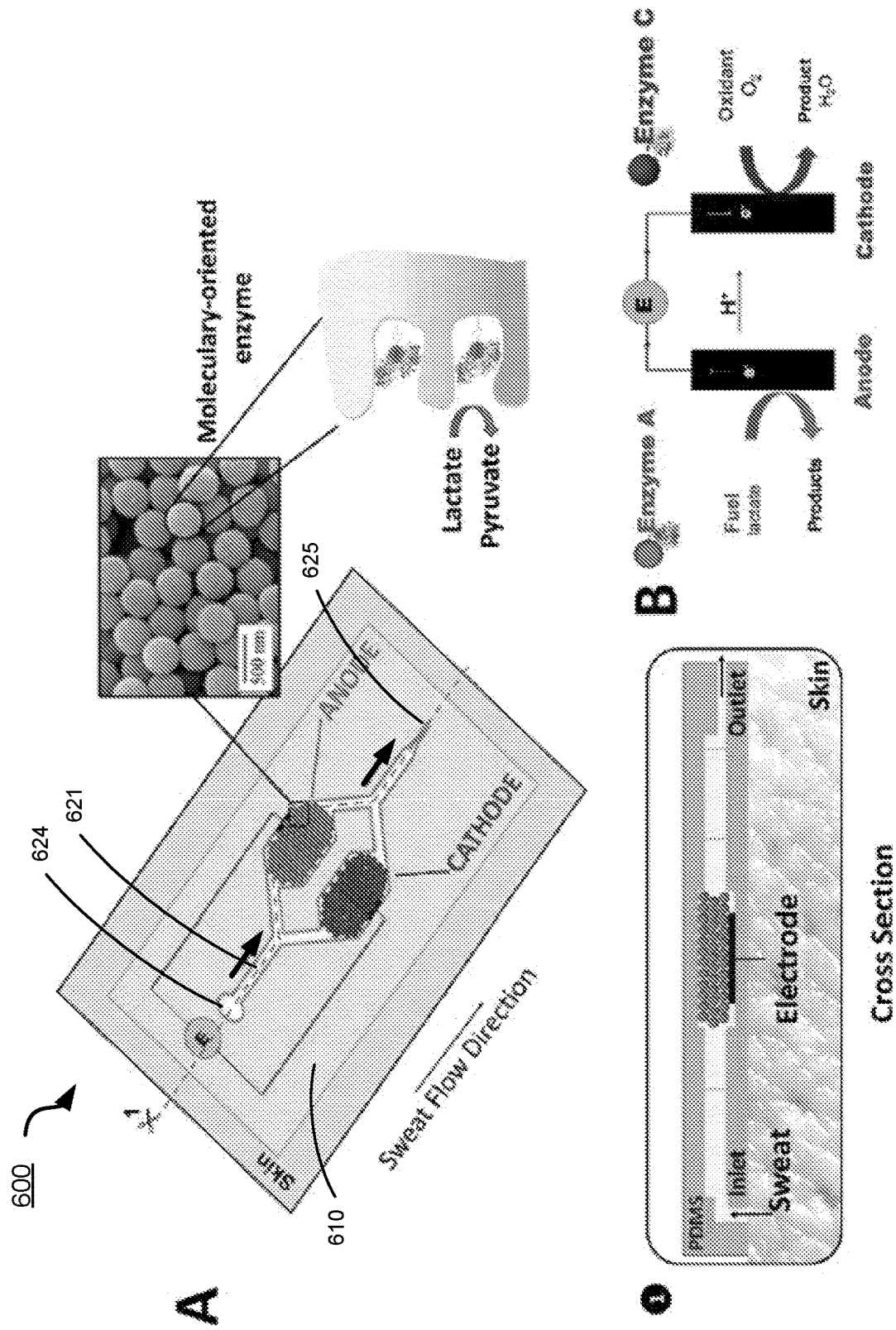
FIG. 6 shows example diagrams showing an example microfluidic electrochemical biofuel cell platform.

FIG. 6 shows example diagrams showing an example microfluidic electrochemical biofuel cell platform in accordance with the present technology. FIG. 6, panel (A) shows a schematic representation of the example microfluidic biofuel cell including separate anodic and cathodic fluid reservoirs containing enzyme-functionalized porous packing fabricated between two PDMS layers. The inset in FIG. 6 panel (A) shows an image and illustration of a cross-sectional view along the broken line "1" of the example microfluidic biofuel cell. FIG. 6, panel (B) shows a schematic representation of the example biofuel cell's operation. For example, electron generation at the enzyme A-functionalized anode through enzymatic oxidation of target fuel (lactate/glucose) followed by electron transfer through an external circuit and finally reduction of oxygen at enzyme C-functionalized cathode.

In some embodiments in accordance with the disclosed technology, a wearable microfluidic biofuel cell device 600 includes a flexible substrate 610 including an electrically insulating material, which is flexible, bendable, stretchable and/or twistable material like (e.g., including examples described with respect to the first layer 110 and/or second layer 120 above). The microfluidic biofuel cell device 600 is structured to include a channel 621 that within the flexible substrate 610, and a first set of one or more holes 624 on a side of the flexible substrate 610 and at a first region of the channel 621, which the first set of one or more holes 624 interfaces with a user's skin and that connects to a first region of the channel to provide one or more inlets to the microfluidic biofuel cell device 600. The channel 621 splits into two branches: a first branch and a second branch. The microfluidic biofuel cell device 600 is structured to include a first cavity intersecting the first branch of the channel 621 beyond the first region to provide anodic reservoir, and a second cavity intersecting the second branch of the channel 621 beyond the first region to provide cathodic reservoir. The microfluidic biofuel cell device 600 includes a second set of one or more holes 625 that connect to a second region of the channel opposite the first region to provide one or more outlets to expel the fluid out of the device 600. The microfluidic biofuel cell device 600 includes one or more anode electrodes in the anodic reservoir, and the microfluidic device 600 includes one or more cathode electrodes in the cathodic reservoir. In some embodiments, the anodic reservoir can contain a first catalyst (e.g., enzyme), on or within the one or more anode electrodes, capable of oxidizing a chemical constituent of the fluid secreted from the skin of the user, which generates electrons, and/or the cathodic reservoir can contain a second catalyst (e.g., enzyme) capable of reducing an oxidant by accepting the electrons generated in the anodic reservoir. In some embodiments, the microfluidic biofuel cell device 600 includes an adhesion layer coupled to the second substrate and attachable to skin, the adhesion layer structured to include one or more openings arranged on the adhesion layer to align with the one or more inlets, whereas in some implementations, the flexible substrate 610 includes or is an adhesive material to bind the device to a user's skin. In implementations, the microfluidic biofuel cell device 600 includes an electrical circuit that connects the anodic and cathodic reservoirs, in which electrons generated in the anodic reservoir travels through the external circuit and into the cathodic reservoir, thereby generating electrical energy.

In some embodiments, the microfluid biofuel cell 600 is electrically coupled to the two or more electrodes and/or electronics unit to supply electrical energy to the device 100. For example, the electronics unit of the device 100 is electrically coupled to the two or more electrodes via electrical interconnects and the microfluidic biofuel cell, and the microfluidic biofuel cell configured to supply electrical energy to the two or more electrodes for electrochemical detection of the biomarker in the fluid. In such implementations, a microfluidic biofuel cell, in some embodiments, includes the anodic reservoir containing a first catalyst capable of oxidizing a component of the fluid secreted from the skin of the user and generating an electron, wherein the first catalyst is an enzyme; a cathodic reservoir containing a second catalyst capable of reducing an oxidant by accepting the electron generated in the anodic reservoir, wherein the second catalyst is an enzyme; and an external circuit that connects the anodic and cathodic reservoirs, wherein the electron generated in the anodic reservoir travels through the external circuit and into the cathodic reservoir, wherein when the first and second catalysts are in contact with the fluid secreted from the skin of the user a chemical reaction occurs resulting in a signal representative of a level of the biomarker in the fluid secreted by the skin of the user. In such implementations, the microfluidic biofuel cell device can be integrated on the same flexible substrate(s) of the device 100, or could be on a separate flexible substrate and electrically connected to the electrochemical sensor contingent of the device 100 via a conductive wire.

Figure 7:
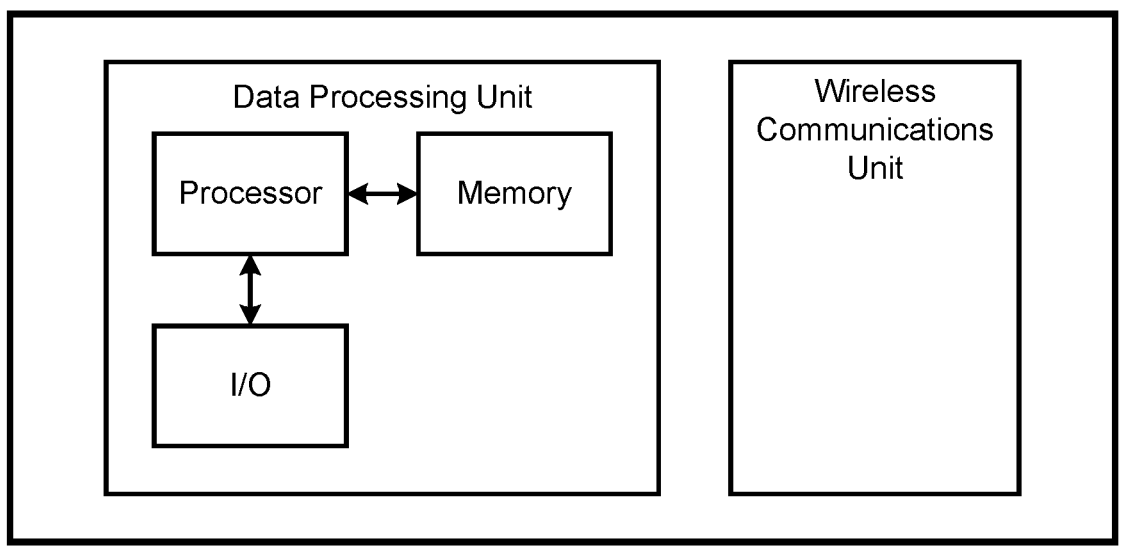
FIG. 7 shows a block diagram of an example embodiment of an electronics unit to interface with example embodiments of the flexible epidermal microfluidic sensor and/or actuator platform in accordance with the present technology.

FIG. 7 shows a block diagram of an example embodiment of an electronics unit to interface with example embodiments of the flexible epidermal microfluidic sensor and/or actuator platform in accordance with the present technology. The electronics unit includes a data processing unit and a wireless communication unit. The data processing unit includes a processor to process data, a memory in communication with the processor to store data, and an input/output unit (I/O) to interface the processor and/or memory to other modules, units or devices of the electronics unit, or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, transmitting or providing information/data to another device, and operating monitoring and/or energy harvesting functionalities by the flexible electrochemical sensor and/or biofuel cell of the epidermal microfluidic device, respectively. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory. The I/O of the data processing unit can interface the data processing unit with the wireless communications unit to utilize various types of wired or wireless interfaces compatible with typical data communication standards, for example, which can be used in communications of the data processing unit with other devices, via a wireless transmitter/receiver (Tx/Rx) unit, e.g., including, but not limited to, Bluetooth®, Bluetooth® Low Energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory, or exhibited on an output unit or an external device. For example, in some embodiments, the platform can include a display unit configured to be in data communication with the data processing unit, e.g., via the I/O, to provide a visual display, an audio display, and/or other sensory display.

Example Fabrication Method of a Microfluidic Electrochemical Device with Potentiometric Detectors In some embodiments, the disclosed systems, devices and methods include a skin-mounted microanalytical flow platform that integrates a soft sweat sampling microfluidic system with microfabricated potentiometric detectors for continuous monitoring of sweat electrolytes. This example soft epidermal microfluidic potentiometric system, shown in FIGS. 8A-8B, can provide efficient sweat sampling and transport over the potentiometric electrodes for detecting analytes and biomarkers in sweat, e.g., such as the sodium and potassium flow ISE detectors. For example, multiple fluidic channels can be used as inlets to provide sufficient amount of sweat to the potentiometric flow detector, e.g., since eccrine sweat glands enable multitude sampling sites. The microfluidic network of the example epidermal microfluidic potentiometric system, which includes four microchannels inlets, ensures that the generated sweat is routed efficiently toward a single channel that contains the potentiometric solid-contact ISE, and exits the detector compartment through an outlet channel, to be replenished by fresh sweat. This results in a dramatically enhanced sweat sampling and flow, for example, as compared to common skin-worn potentiometric sensors, while addressing carry-over and mixing effects.

FIGS. 8A and 8B show illustrative diagrams of a specific example embodiment of the integrated microfluidic electrochemical device 100 (labeled 800 in FIGS. 8A and 8B), in which the electrochemical sensor component is a potentiometric sensor for the detection of specific analytes (sodium and potassium in the specific example). FIG. 8A, left shows an image of the example potentiometric sensor fabricated with ion-selective electrodes and integrated with wireless conformal electronics. FIG. 8A, right is a schematic representation of the example potentiometric sensor component of the device 800 comprising a sodium ion-selective electrode 801 and a potassium ion-selective electrode 802 and a reference electrode. 803 on a flexible substrate 810 (e.g.

which can include the features described for the first layer 110). FIG. 8B, left panel i, shows an image of the potentiometric sensor component of the device 800 fabricated with the ion-selective electrodes without the wireless conformal electronics. FIG. 8B, middle panel ii, shows an illustrative schematic representation of the example layered device configuration on skin, which includes the flexible substrate 810 (e.g., top PDMS layer) with incorporated ion-selective electrodes, a second flexible substrate 820 (e.g., middle PDMS layer) configured with four inlets 824 and one outlet 825, a reservoir 823, and channels 821 from the reservoir to the inlets and outlet, and an adhesive layer 830 attachable to the skin and having holes that align with the inlet holes 824. FIG. 8B, right panel iii, shows an illustrative schematic representation of operation by the example device for sweat collection and analyte detection when attached on skin. FIG. 8B, panel iii depicts the sweat flowing from the sweat glands, through the four inlets, and into the four corresponding channels to the reservoir. Once the sweat reaches the reservoir, the sweat passes over the sodium and potassium ions-selective electrodes where sodium and potassium levels are measured and lastly, the measured sweat exits the device through the outlet enabling replenishment of the reservoir with fresh sweat.

Example fabrication processes and embodiments of the epidermal microfluidic potentiometric platform are described below, which include data from example implementations demonstrating the epidermal sensing capabilities of the devices for continuous real-time simultaneous monitoring of potassium and sodium during cycling activity of different healthy subjects.

(a) Fabrication of Soft Electrodes

In example implementations, a 70 nm layer of PMMA was spin-casted onto a 4" Si wafer to serve as a sacrificial layer. Subsequently, polyimide (PI-2545, HD Microsystems, USA) was spin-casted to yield a 1.6 μm film on top of the PMMA, followed by soft baking at 110 and 150° C. for 3 min on a contact hot plate to remove volatile solvents, and followed by curing at 250° C. for 1.5 hour in a vacuum oven. Photolithography was used to pattern sensors and interconnect layers of Ti (10 nm)/Cu (550 nm)/Ti (20 nm)/Au (200 nm) deposited by an electron beam evaporator (Temescal BJD 1800).

A second layer of polyimide of the same thickness as the bottom layer was placed on the sensor/interconnect layer on a neutral mechanical plane. This top polyimide layer also served as electrical insulation and strain isolation. Reactive Ion Etching (Plasmalab Oxford P80) was used to etch the polyimide and define the mesh layout of the array, exposing only the bonding pads and the sensors. The PMMA layer was undercut with boiling acetone to enable the removal of the mesh from the Si wafer using a water-soluble PVA tape (3M Company, Maplewood, MN). The exposed back surface of the mesh was then mounted on glass slides for deposition of Ti (6 nm)/$SiO_2$ (60 nm) by sputter coating (using Denton Vacuum LLC, Discovery 635). A PDMS layer of 500 μm (Dow Corning, Sylgard 184) was spin-coated onto a glass slide with its surface treated by PMMA to reduce adhesion of the Si. The devices were then transferred onto the PDMS through the formation of covalent bonds by condensation reactions between UVO treated Si and $SiO_2$ on the back side of the devices. The tape was finally dissolved with DI water.

(b) Screen Printing Process of the Potentiometric Sensors

In example implementations, screen printing was conducted using a semi-automatic MMP-SPM printer (Speedline Technologies, Franklin, MA) and stainless-steel stencils developed using AutoCAD software (Autodesk, San Rafael, CA). The potentiometric sensors were screen-printed on a microfabricated Au electrode using two separate layers. First, an Ag/AgCl conductive ink was used to print the conductive collector followed by printing the conductive carbon working electrode. The printed layers were cured at 85° C. for 20 min after each step.

(c) Modification of the Electrodes

In example implementations, the following procedures were employed for preparing the potassium recognition layer. In particular, 2 mg valinomycin were dissolved in 1 mL of tetrahydrofuran (THF) along with 0.5 mg of potassium tetrakisIJ4-chlorophenyl) borate. After complete dissolution, 32.8 mg of polyvinyl chloride (PVC) were added gradually until complete dissolution, followed by the addition of 71.1 μL dioctyl sebacate (DOS). The resulting solution was left with stirring in vortex for one hour. After homogenization, 5 μL of the resulting cocktail solution were cast on the surface of carbon electrode transducer using 1 μL aliquots. In example implementations, the following procedures were employed for preparing the sodium recognition layer. In particular, the potentiometric sodium ion-selective electrode membrane was prepared using 1 mg (i.e., 1 wt %) sodium ionophore X, 65.45 mg DOS. 33 mg PVC and 0.55 mg sodium tctrakis[3,5-bis(trifluoromethyl)phenyl]borate (Na-TFPB), by dissolving in 660 μL of THF. To prepare the sodium selective membrane, this cocktail solution was drop-casted (i.e., five 1 μL aliquots) on top of the printed carbon transducer and left overnight for complete drying. Lastly, the reference electrode was prepared by drop-casting 0.5 μL of a solution containing 78.1 mg of PVB and 50 mg NaCl in 1 mL methanol on the Ag electrode. After drying, 0.5 μL of polyurethane (PU) was casted on the membrane in order to prevent leaching.

(d) Fabrication of Microfluidic Channels and Device Assembly

In example implementations, a 50 nm layer of Cr was first deposited using an electron beam evaporator (Temescal BJD 1800) to act as an etch mask. Photolithography was then used to pattern the microfluidic channels. The unmasked portions of the Si wafer were etched by Deep Reactive Ion Etching (Plasmalab Oxford P100), yielding 300 μm tall patterns. Depth measurements of the Si master were performed using a Dektak 150 surface profiler (Vecco, Plainview, NY). A 70 nm layer of PMMA (PMMA 950 A2, MicroChem, USA) was next spin-casted onto the Si master, followed by soft baking at 180° C. to reduce Si adhesion to the master. A Si layer of 500 μm (Dow Corning, Sylgard 184) was then spin-casted onto the Si master to yield the final microfluidic pattern.

A flexible PDMS (i.e., 30:1 base/curing-agent ratio) was used for maintaining mechanical compatibility with the skin. Further increase in the structural stability, to avoid collapsing of the reservoir (due to its large diameter, compared to the thin dimensions of the top PDMS layer) was achieved by two procedures. The two procedures included the incorporation of micropillars within the reservoir to increase the stiffness locally and the use of a 50 μm rigid PDMS (i.e., 10:1 base/curing agent ratio) to increase the Young's modulus of the microfluidic features, thereby increasing the stiffness in the channels. Finally, the sweat was driven to an outlet channel (200 μm wide by 300 μm height), which lead to the sweat's continuous replenishment and minimal back pressure. After the electrode modification with their respective recognition layers, the top PDMS layer containing the sodium/potassium sensors was bonded with the microfluidic PDMS layer by UVO treatment for 6 min only over microfluidic PDMS.

(e) Wireless Transceivers

In the example implementations, a printed circuit boards PCB was used to control the potentiometric operations. The controller used in the PCBs was a CC2541 from Texas Instruments (TI). This controller has an integrated BLE function which enables wireless connection to a host device, such as a smartwatch, smartphone, or laptop. The digitized data from the sodium and potassium sensors were transmitted as BLE packets via the controller to a host laptop and displayed using a custom-made graphic interface. The PCB was powered by a lithium (Li) ion rechargeable battery. The battery's output was regulated using a low dropout regulator (LP2981 from TI) to obtain 3.0 V precise and stable power for every circuit component. The batteries have 100 mAh capacitance and dimensions of 31×11.5×3.8 mm. The size of the developed PCB was 30×13.7 mm. On-body tests were performed using the wireless transceiver.

The potentiometric sensor used a voltage follower circuit with an operational amplifier (AD8605 from Analog Devices Inc.) for measuring the potential signal between the reference and the working electrodes. This amplifier has an extremely low input bias current (<1 pA) with rail-to-rail operation, enabling precise and wide-range measurement. The output of the voltage follower circuit was followed by an RC low-pass filter and converted to a digital value using the ADC.

(f) Conditions for Example In-Vitro Studies Using an Example Embodiment of a Microfluidic Electrochemical Device with Potentiometric Detector In example implementations, electrochemical characterization of sodium and potassium potentiometric electrodes was initially performed under FIA in the microfluidic system. A 403U/VM2 pump (Watson-Marlow Bredel Pumps, Wilmington, MA) allowed the pumping of water or artificial sweat composed of urea, lactic acid, ammonium ion ($NH_4^+$), calcium ion ($Ca^{2+}$), magnesium ion ($Mg^{2+}$), uric acid, glucose, sodium ion ($Na^+$) and potassium ion ($K^+$) to the microfluidic device at 200 µL/min. Varying concentrations of sodium between 0.1 to 200 mM and potassium between 0.1-100 mM with—10-fold increments—were injected with a six-port Rheodyne 7000 valve (IDEX Health & Science LLC, Rohnert Park, CA) containing a 20 µL sample loop. Due to the slow flow rate of on-body sweat conditions, slow flow injection experiments were carried out at 20 µL/min using an Instech pump (Instech P625/900-143, Plymouth Meeting, PA). During this FIA, only one inlet was used for continuous pumping, with the microfluidic device filled initially with artificial sweat and instantaneously responding to the passage of the injected sample-metabolite zone.

(g) Conditions for Example On-Body Studies, with Human Subjects, Using an Example Embodiment of a Microfluidic Electrochemical Device with Potentiometric Detector In example implementations, epidermal evaluation on human subjects was conducted in strict compliance following a protocol approved by the IRB at the University of California, San Diego. Three healthy volunteers were recruited for on-body evaluation of the sensors. The microfluidic system was attached to the skin using a 3M Double Coated Medical Tape (#1522) (Maplewood, MN) with 2 mm openings aligned with the 0.5 mm inlets of the device. Next, 0.5 µL of blue food dye was placed on each sweat collection area; the device was then transferred to the lower back of the volunteers, previously cleaned with rubbing alcohol. For mounting the flexible electronics, a (30:1 base/curing agent ratio) flexible 45×6 $cm^2$ PDMS bandage was prepared for placement on the human subject's arm and 3 M transparent film Tegadem (#16004) (Maplewood, MN) was used for mounting the electronic of the back of the human subject. After placement of the device, the volunteer was asked to perform physical exercise on a stationary bike (Sunny Health & Fitness SFB1002C, Los Angeles). Exercise biking conditions were kept at high intensity, constant speed, and a constant temperature of 24° C. in order to obtain comparable results. The potassium and sodium sensors, incorporated inside of the PDMS top layer, were connected to a PCB with potentiometric and Bluetooth® capabilities through FID cables. The sweat electrolytes signals were recorded in real-time during a 2000 s exercise activity, using a laptop and a homemade system control developed in Matlab. Each on-body experiment was carried out with device outlet facing upward as contributions from gravity forces during sensing reservoir filling were negligible.

Example Results of Example Implementations of a Microfluidic Electrochemical Device with Potentiometric Detectors (a) Results from Fabrication, Mechanical Resiliency, and In-Vitro Testing of the Example Microfluidic Device with Potentiometric Detectors Integrating polymeric PDMS-based soft material, with similar Young modulus to the skin, offers skin conformity required for mechanical deformation experience by the wearer. FIG. 8A, left shows a 2 cm circular-shape microfluidic device photograph which includes two PDMS layers of a total of 1 mm thickness. A first PDMS layer, with the microfluidic features, is comprised of four inlets, with 750 µm openings, and respective channels that connect to the 5 mm detection chamber. Sweat flow is driven to an outlet channel, parallel to the skin, which allows continuous replenishment of the biofluid. The second PDMS layer supports the sodium and potassium sensors. The electrodes are based on lithography-made Au current collectors, insulated with polyimide. After transferring to the PDMS, carbon and silver inks are printed to support the sodium and potassium selective sensors and the reference electrode, respectively. The potentiometric sodium/potassium ion-selective electrode membranes are layer-by-layer casted on the carbon ink to provide selectivity for the specific ion (i.e., potassium or sodium) using the appropriate ionophore receptor.

FIG. 8A shows photographs and an illustrative schematic of an example embodiment of the microfluidic device integrated with the fabricated ion-selective electrodes and wireless circuitry, which was employed in example implementations described below. The sensor can then transform the activity of the target ion in the sweat into an electrical potential signal that is measured by the miniaturized circuitry as shown in FIG. 8A, right.

The prevalence of a large number of sweat glands across the body makes skin a natural sweat pumping machine during periods of exercise or heating. The two-layer PDMS-based microfluidic potentiometric device is mounted on the epidermis by attachment with a medical grade adhesive which includes four holes of 2 mm diameter where the four holes match the four inlets of the PDMS layer, enabling sweat collection as shown in FIG. 8B, panel ii. The strong adhesion between the microfluidic device and the epidermis provides enough pressure for the sweat pores located within the adhesive openings to naturally pump fresh sweat through the microfluidic device. After wetting the microfluidic channels, the sweat efficiently reaches the detection chamber. This 5 mm diameter chamber includes the two sodium and potassium electrode sensors and three pillars which ensure the structural stability of the detecting chamber. For healthy individuals, the sensing chamber is thus completely filled within 15 min to allow real-time monitoring of fresh sweat. The sweat is driven to an outlet microchannel (200 μm wide×300 μm height) to allow facile replenishment and to minimize back pressure.

FIG. 8B shows a representative schematic of working principle of the epidermal device: FIG. 8B, panel i is a representative photograph of the microfluidic device, FIG. 8B, panel ii is a representative schematic of a skin-mounted microchip depicting the three-layered configuration, a top PDMS layer which includes the sensors, a second PDMS layer incorporating the microchannels and adhesive layer in contact with the skin, and FIG. 8B, panel iii is a representative schematic of the microchip operation in which the sweat generated by the sweat glands is driven from the inlets to the detection chamber.

Epidermal monitoring of analytes and biomarkers during exercise requires careful assessment of the resilience of the sensor chip against mechanical deformations experienced during on-body applications. These factors were studied in the example implementations.

Figure 9A:
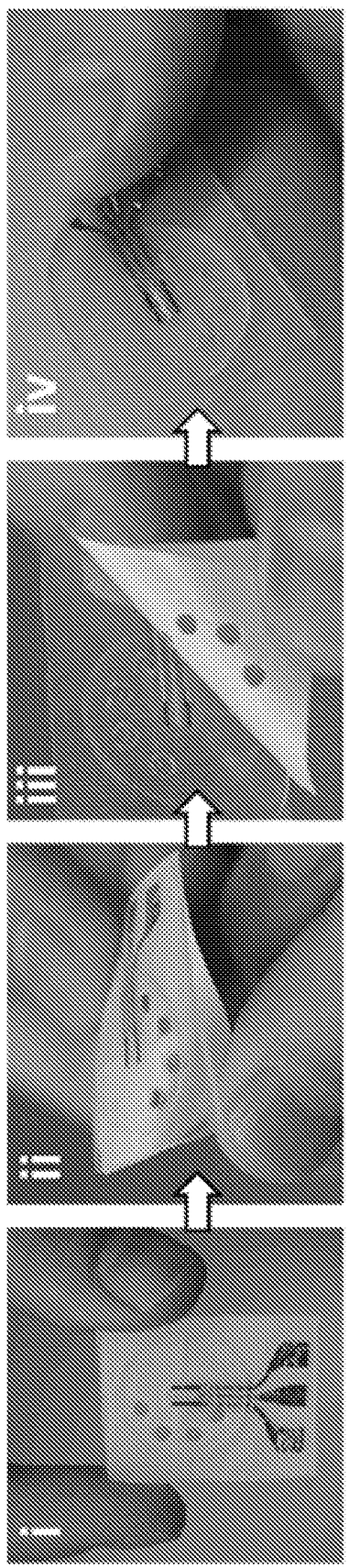
FIG. 9A shows images depicting the example microfluidic potentiometric platform and process of placing the platform on a human subject.

FIG. 9A shows an image sequence depicting the transfer of the example integrated ISE-microfluidic detection device to the skin of a user. Specifically, image (i) shows a fabricated device; images (ii) and (iii) show the removal of a medical-tape protective paper that covered the device; image (iv) shows adhesion of device to the skin.

Figure 9B:
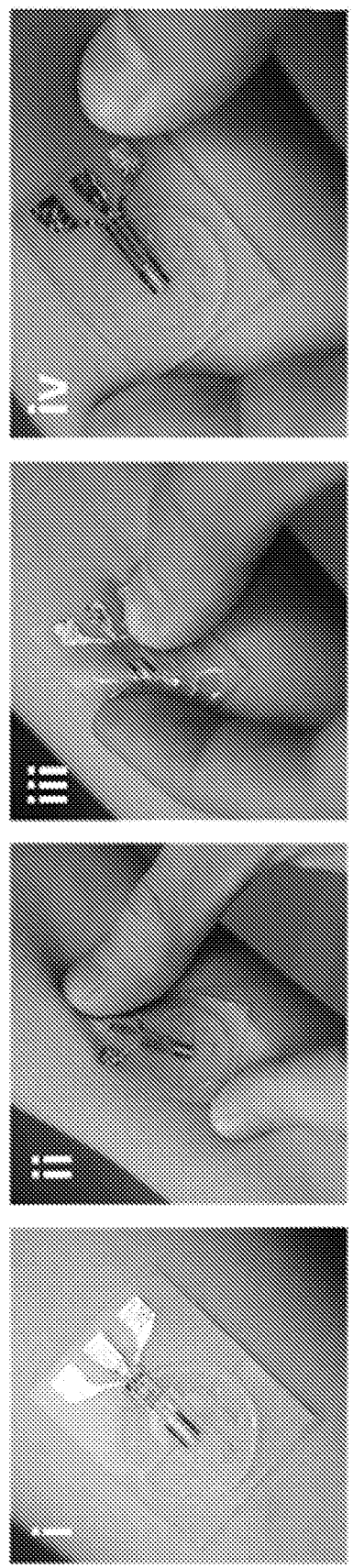
FIG. 9B shows images depicting the physical resilience of the example microfluidic potentiometric platform to mechanical deformations.

FIG. 9B shows an image sequence depicting mechanical strain applied to the example integrated ISE-microfluidic detection device while on a user's skin. For example, visual examination of the images shows that the device's resiliency to mechanical strain, e.g., image (i) simply shows the device mounted to skin, whereas images (ii), (iii) and (iv) show the device under different strain tests: twisting in image (ii), bending in image (iii), and stretching in image (iv).

Importantly, as depicted in FIG. 9B, the mechanical strains have negligible effect upon the structural integrity of the chip mounted on the skin. Furthermore, no observable damage or change in the potentiometric response was noted after these stresses, reflecting the robustness of the device to endure various stress deformations.

Figure 10A:
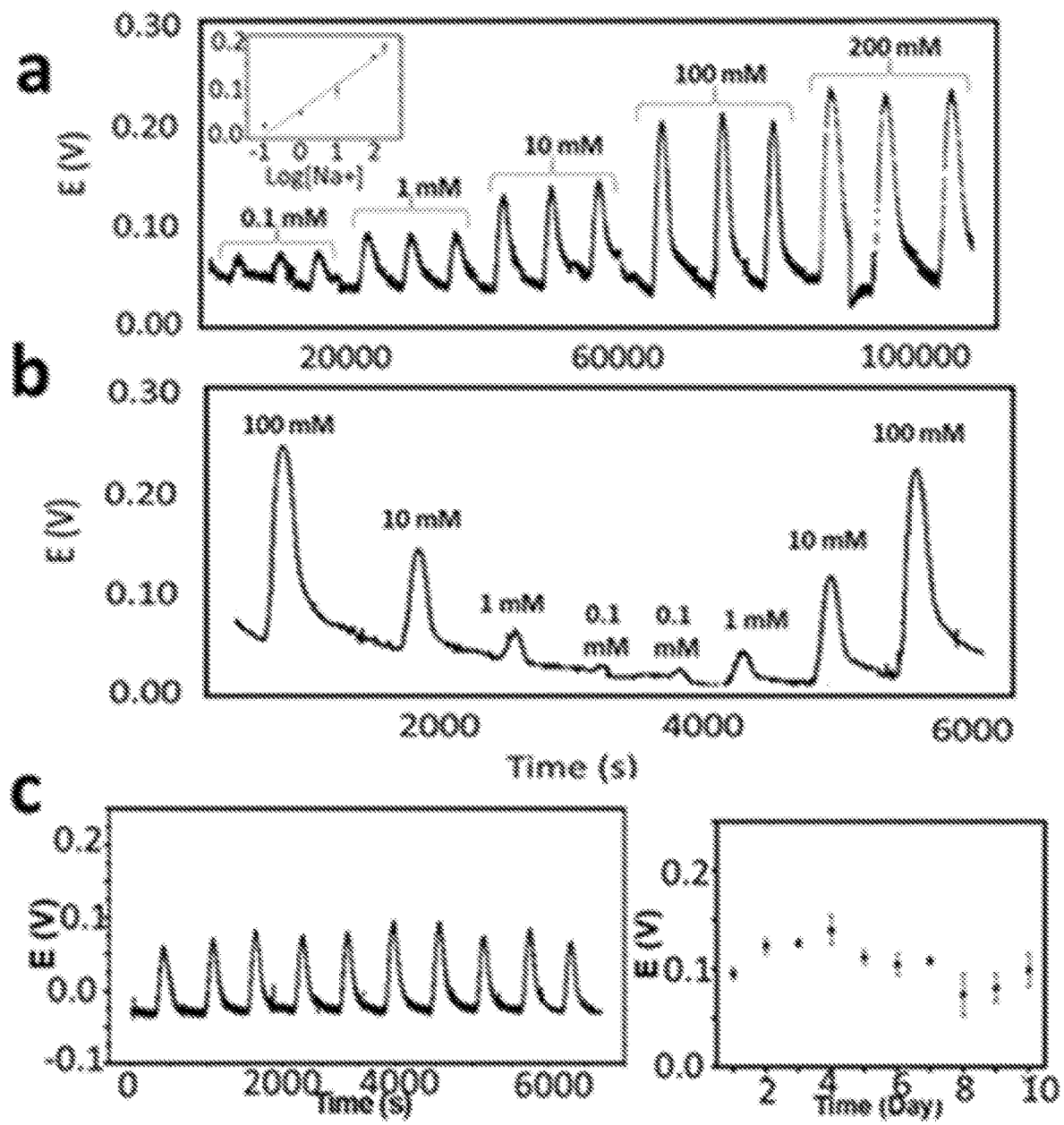
FIGS. 10A and 10B show data plots from an example in-vitro flow injection analysis of sweat electrolytes using an example microfluidic potentiometric platform.
Figure 10B:
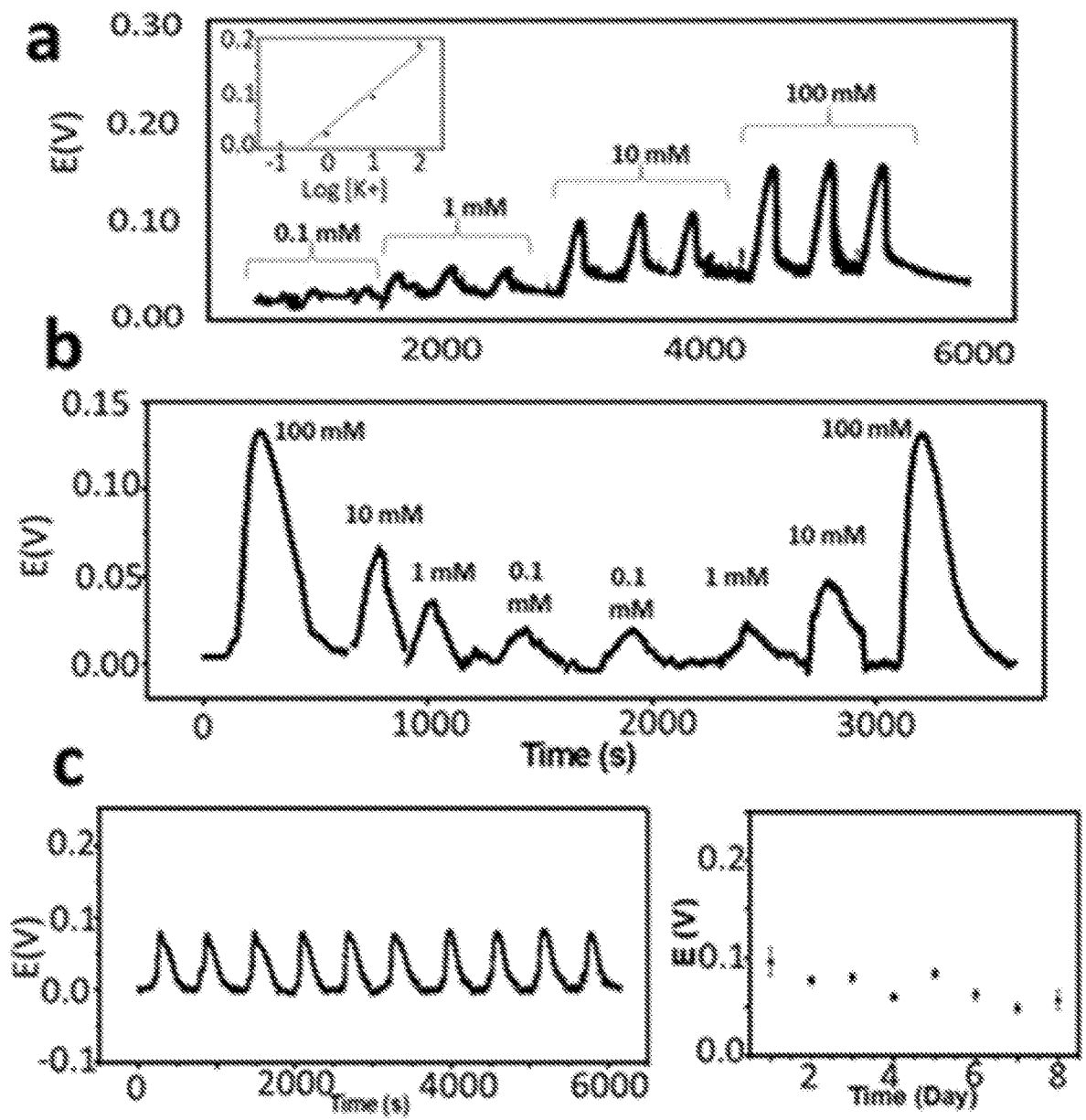

FIGS. 10A and 10B show data plots depicting example data from in-vitro sensing experiments that were carried out initially to characterize the potentiometric microfluidic detection of sodium and potassium as, respectively. The analytical performance of the potentiometric electrodes was evaluated using FIA with a flow rate of 20 μL/min. In the initial evaluation, consecutive 10 μL of $Na^+$ and $K^+$ were injected with the concentration of each ion increasing from 0.1 to 100 mM. The potentiometric microfluidic detection of the initial evaluation is shown in FIG. 10A, panel (a) and FIG. 10B, panel (a). More specifically FIG. 10A panel (a) and FIG. 10B, panel (a) depict a flow-injections in water for triplicate 20 μL injections of 0.1 mM-200 mM NaCl and KCl solutions, along with calibration plots. The insets of FIGS. 10A, panel (a) and 10B, panel (a) depict the resulting calibration plots characterized with a Nernstian slope of 60±12 mV for $K^+$ and sub-Nernstian slope of 46±7 mV for $Na^+$, with a linearity of r=0.96 and r=0.98 for $K^+$ and $Na^+$, respectively. Good analytical performance was also observed in an artificial sweat sample containing the most common sweat electrolytes (e.g., $Ca^{2+}$ and $Mg^{2+}$), indicating there is negligible interference from potential co-existing ions.

Figure 11:
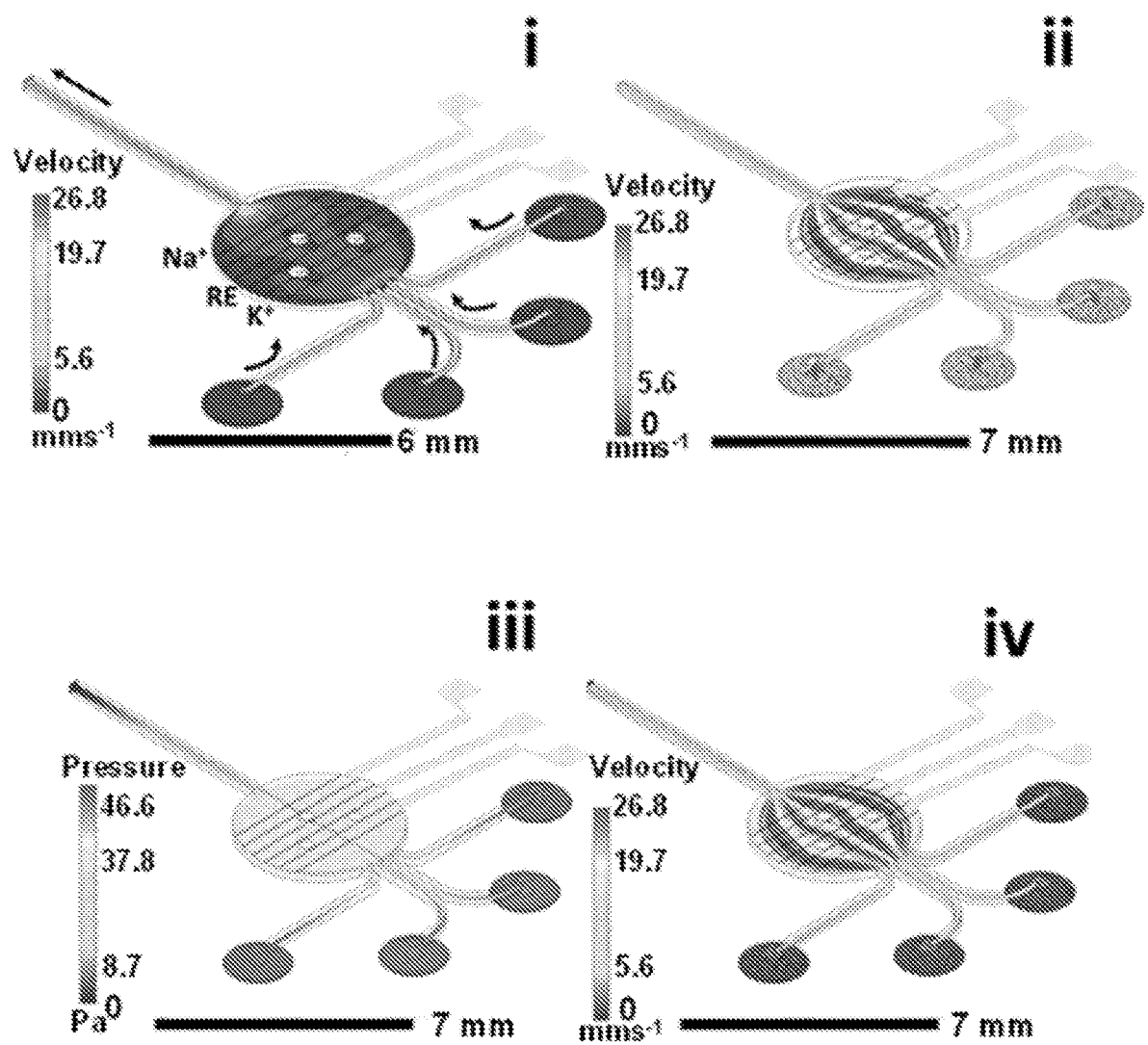
FIG. 11 shows illustrations depicting example theoretical simulations of the example microfluidic potentiometric platform.

Since the absence of carry-over effects is essential for the function of the epidermal microfluidic system, carry-over effects were also studied first in-vitro using FIA as depicted in FIGS. 10A, panel (b) and 10B, panel (b). In particular, FIGS. 10A, panel (b) and 10B, panel (b) provide a depiction of carry-over evaluation of the sensors using flow injection (20 μL/min) for increasing and decreasing NaCl/KCl concentrations from 100 mM 0.1 mM. In this study, consecutive flow injections of $Na^+$ and $K^+$ solutions of decreasing and increasing concentrations, from 100 mM to 0.1 mM and then in reverse from 0.1 mM to 100 mM, were carried out. The data depict that the flow-through microsystem and detection chamber eliminate any carry-over effects, indicating suitability of the microfluidic potentiometric sensor for real-time sweat monitoring. Repeatability and stability measures were also performed. FIGS. 10A, panel (c), left and 10B, panel (c), left depict the repeatability measurements of the sensor response to 10 mM ion concentration in water using 10 repetitive flow injections. FIGS. 10A, panel (c), right and 10B, panel (c), right depict the stability measurements of the sensor over several days for static system using 10 mM ion concentration in water. Notably, FIGS. 10A, panel (c) and 10B, panel (c) illustrate that the microchip sensor can be used several times during the same day as well as over the course of 5 days and importantly, provide similar results as the first day the microchip sensor was used. FIG. 11 indicates that after a week, the potential signals decreased while the deviation of same day repeatability increased, producing changes of 23% and 19% for sodium and potassium, respectively, as compared to the signals of the first day. However, such variations are not of major concern as these low-cost fluidic platforms are intended for a short-term (i.e., daily) use.

FIG. 11 shows diagrams depicting example data of the properties of the flow in the device studied by computational simulation, shown in panels ii-iv. In particular, FIG. 11 provides theoretical simulation in the microfluidic system, representing i) velocity distribution, ii) stream lines, iii) pressure distribution and iv) pressure combined with streamlines. An epidermal fluidic design used earlier for amperometric detection (i.e., the sensor as depicted in FIG. 1) of metabolites was used for potentiometric monitoring of sodium and potassium concentrations in sweat. Before modifying the electrodes with the reagent layers, fluid mechanics of the sweat were studied within the microchannels network and detection reservoir, in consideration of the different electrode layout in this reservoir. In consideration of the minor change in geometry of the potentiometric sensor, the fluidic system is contemplated to collect sweat from adjacent sweat glands and subsequently transport the sweat to the sensor chamber, providing a uniform flow over the surface of the sensor. To confirm this hypothesis, a simulation using the same parameters employed in the epidermal amperometric biosensor (i.e., the sensor as depicted in FIG. 1) study were used with only changes in the sensor's geometry. Accordingly, the flow direction was evaluated by means of the streamlines analysis as depicted in FIG. 11, panel ii. Importantly, FIG. 11, panel ii indicates an absence of recirculating areas and stagnant flow, except for the expected stagnation points in the pillars leading edge.

In addition to flow properties, back pressure is another important parameter. In order to have a continuous flow rate consistent with the natural sweat glands flow rate, there must be minimum back pressure. Back pressure was evaluated by a pressure contour plot at the device midplane and inlet as depicted in FIG. 11, panel ii. As expected for a pressure driven flow, the highest pressure is found at the inlet with an approximately constant pressure inside the reservoir. The pressure loss was 49 Pa, which was smaller as compared to the sweat pressure from the eccrine sweat gland of 72 kPa. Overall, the judicious analysis of these parameters, FIG. 11, panel i shows that the average velocity magnitude in the reservoir midplane is uniform and similar to the previous sensor (i.e., the sensor as depicted in FIG. 1). The streamline analysis as depicted in FIG. 11, panel iv shows that the flow direction and pressure distribution are not significantly affected by the change in sensor geometry. Therefore, the microchannel system can be used towards potentiometric sensing with similar performance as the earlier optimal design (i.e., the sensor as depicted in FIG. 1).

(b) Results from Example Real-Time On-Body Sweat Monitoring with Human Subjects

The fluidic mechanic performance of the devices was confirmed experimentally as depicted by FIGS. 12A-12B and 13A-13B. FIGS. 12A-12B and 13A-13B show the set up and the continuous monitoring of sweat electrolyte dynamics during indoor fitness cycling. In this experiment, three adult subjects performed fitness cycling for up to 50 minutes. The sodium and potassium ions were monitored continuously using the integrated patch while the data was transmitted via Bluetooth® to a laptop for analysis. Depending on the fitness level of the human subject, the sweat filling process during which the background noise is more dominant, can varies.

Figure 12A:
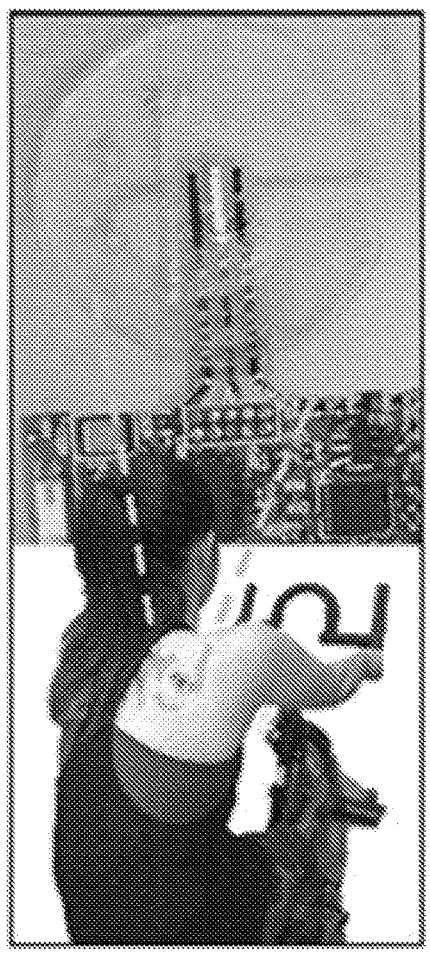
FIG. 12A shows images depicting the placement of the example microfluidic potentiometric platform on a human subject.
Figure 12B:
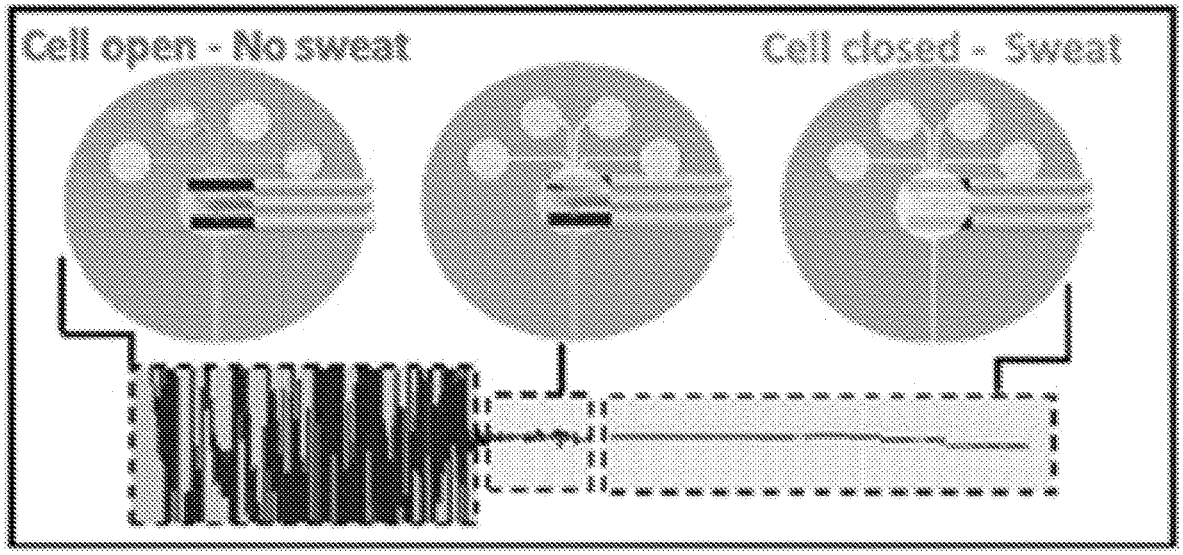
FIG. 12B is an illustrative schematic of the sequence of events in using the example microfluidic potentiometric device.

FIG. 12A shows an image of the example integrated ISE-microfluidic device with wireless circuitry, which was placed on the volunteer's back shoulder. FIG. 12B shows three diagrams of the example integrated ISE-microfluidic device depicting a sequence of events that correspond to the on-body signals obtained from a human subject. For example, as shown in FIG. 12B it takes over 5 min for the reservoir to fill with sweat, during which only the background signal is recorded, e.g., shown in the rectangular below the left-most device illustration labeled "cell open, no sweat." However, as soon as the detection reservoir is filled with sweat (shown in the middle device illustration), a smooth analytical signal is generated for the target ions along with minimal noise levels, e.g., shown in the rectangular below the middle and right-most device illustrations labeled "cell closed, sweat."

Figure 13A:
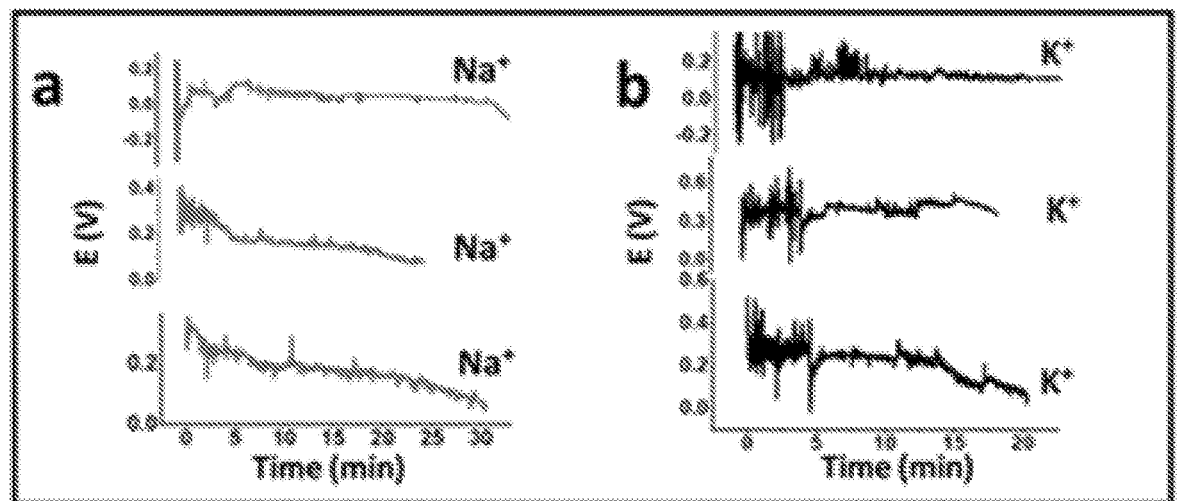
FIGS. 13A and 13B show data plots of continuous flow monitoring of electrolytes using the example microfluidic potentiometric device.
Figure 13B:
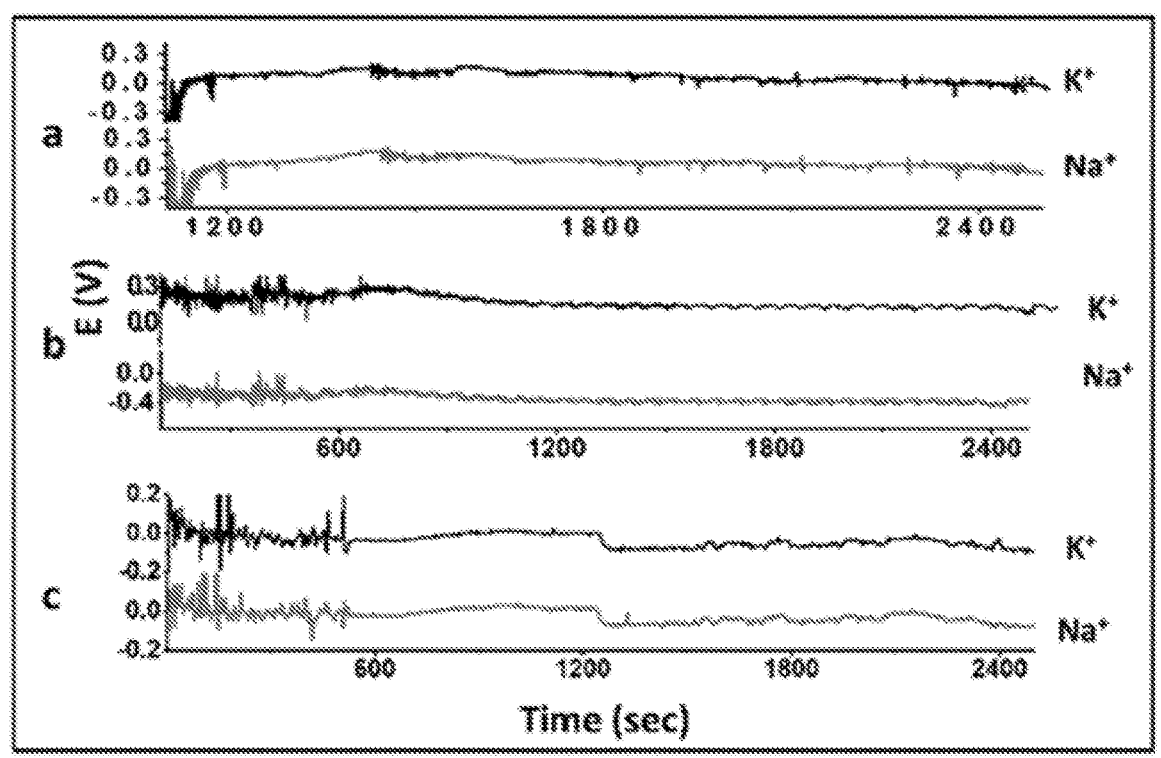

FIG. 13A shows data plots for separate monitoring of $Na^+$ and $K^+$ using the example integrated ISE-microfluidic device for each of the three different human subjects; whereas FIG. 13B depicts the simultaneous monitoring of the cations (i.e., $Na^+$ and $K^+$) that was carried out over all three subjects. The data indicate that different individuals showed a different loss of ions during exercise. The electrolyte fluctuations are correlated to the decrease/increase in the potential, and their concentrations can be estimated considering an external calibration curve explored under flow injection analysis as shown in FIG. 10. Notably, these data clearly demonstrate the dynamic changes in the $Na^+$ and $K^+$ concentrations during this prolonged 2400 s exercise activity.

As discussed above, an example fully-integrated epidermal microfluidic detector for performing continuous real-time on-body monitoring of potassium and sodium in sweat was developed and utilized in example implementations, demonstrating new capabilities for microfluidic natural sweat pumping that address challenges of early epidermal electrolyte sensors, including sweat mixing and removal, skin contamination and carry-over, while ensuring efficient transport of the biofluid over the detector surface. Mounted on the skin, without hindrance to the wearer, the example device was shown to offer comfort and case of use to the wearer while ensuring efficient contact with the epidermis. Combined with a small printed potentiometric circuitry for controlling the entire operation and the wireless real-time collection of data, the example soft fluidic device provides selective monitoring of sodium and potassium during cycling exercise. On-body studies with healthy subjects demonstrated the capabilities of the dual-ion potentiometric detector during physical activity. Future fluidic platforms will offer periodic calibration to account for variations in the sensor activity and will provide timely quantitation in connection to periodic introduction of the electrolyte standards. Such skin-conforming microfluidic chemical sensing system can be readily expanded to the real-time non-invasive monitoring of other sweat electrolytes and biomarkers, paving the way for a new generation of soft electrochemical wearable microfluidic systems.

EXAMPLES

In some embodiments in accordance with the present technology (example A1), a device includes an electrochemical sensor comprising two or more electrodes disposed on a first side of a first substrate, a microfluidic device comprising a second substrate, the second substrate structured to include (i) a channel, (ii) a first set of one or more holes that connect to a first end of the channel and provide one or more inlets, (iii) a reservoir intersecting the channel, wherein the electrochemical sensor on the first substrate is aligned with the reservoir of the second substrate, and (iv) a second set of one or more holes connected to a second end of the channel and provide one or more outlets, wherein the two or more electrodes on the side of the first substrate are aligned with the reservoir the second substrate; and an adhesion layer coupled to the second substrate and attachable to skin, the adhesion layer structured to include one or more openings arranged on the adhesion layer to align with the one or more inlets, wherein when the device is electrically coupled to an electronics unit and adhered to the skin of a user, the device is operable to detect a biomarker in a fluid secreted from the skin of the user into the microfluidic device.

Example A2 includes the device of example A1, wherein the reservoir further comprises one or more pillars to support the first flexible substrate or two or more electrodes.

Example A3 includes the device of example A1, wherein the first substrate and the second substrate are a flexible and electrically insulating material.

Example A4 includes the device of example A1, wherein the electrochemical sensor includes: a first electrode having a surface that includes a catalyst or a reactant corresponding to an analyte in the fluid, and a second electrode disposed on the first substrate in a location separated from the first electrode, the first and second electrodes operable to measure an electrical signal corresponding to a redox reaction including the chemical substance and the analyte at the electrochemical sensor.

Example A5 includes the device of example A1, wherein the first substrate and/or the second substrate comprises polydimethylsiloxane (PDMS).

Example A6 includes the device of example A1, wherein the first substrate, the second substrate and the adhesion layer are configured as three circular, flexible layers having a diameter in a range of 1 cm to 10 cm.

Example A7 includes the device of example A1, wherein the electronics unit is electrically coupled to the potentiometric sensor via electrical interconnects, the electronics unit configured to supply electrical energy to the potentiometric sensor.

Example A8 includes the device of example A1, further comprising a biofuel cell, wherein the device includes the electronics unit electrically coupled to the electrochemical sensor via electrical interconnects and the biofuel cell, the biofuel cell configured to supply electrical energy to the electrochemical sensor.

Example A9 includes the device of example A7, wherein the biofuel cell is a microfluidic biofuel cell including separate anodic and cathodic fluid reservoirs containing enzyme-functionalized porous packing fabricated between two layers.

Example A10 includes the device of example A1, wherein the electrochemical sensor comprises a third electrode.

Example A11 includes the device of example A1, wherein the electrochemical sensor comprises a fourth electrode.

Example A12 includes the device of example A1, wherein the electrochemical sensor is operable to obtain one or more of amperometric measurements, potentiometric measurement, or square-wave voltammetric measurements.

Example A13 includes the device of example A1, wherein the electronics unit includes: a signal conditioning circuit to amplify signals detected by the electrochemical sensor, a data processing unit including a processor and memory to process data based on the measured signals, and a wireless communications unit to wirelessly transmit the processed signals to an external device.

Example A14 includes the device of example A13, wherein the wireless communications unit includes a Bluetooth® Low Energy chipset.

Example A15 includes the device of example A1, wherein the reservoir can fill with the fluid secreted from the skin of the user in less than 5 minutes.

Example A16 includes the device of example A1, wherein the device enables a constant, rapid fluid transport to the reservoir.

Example A17 includes the device of example A1, wherein the device can simultaneously detect two or more biomarkers.

Example A18 includes the device of example A1, wherein the device is resilient to mechanical deformations, wherein the mechanical deformations include bending, stretching, compressing, and/or twisting.

Example A19 includes the device of example A1, wherein the device is stable to repeated use for at least about 5 days.

Example A20 includes the device of example A1, further comprising a transducer element to transform a signal resulting from detection of the biomarker into a different signal addressable by optical or electronic means.

Example A21 includes the device of example A1, wherein the biomarker is one or more of an electrolyte, glucose, lactate, a pro-inflammatory cytokine, an anti-inflammatory cytokine, a catecholamine, a neuropeptide, and/or a protein.

Example A22 includes the device of example A21, wherein the electrolyte is one or more of sodium, potassium, chloride, bicarbonate, calcium, phosphate, magnesium, copper, zinc, iron, manganese, molybdenum, copper, and chromium.

Example A23 includes the device of example A1, wherein the two or more electrodes are ion-selective electrodes selected from the group consisting of sodium, potassium, chloride, bicarbonate, calcium, phosphate, magnesium, copper, zinc, iron, manganese, molybdenum, copper, and chromium ion-selective electrode.

In some embodiments in accordance with the present technology (example B1), a device includes an electrochemical sensor comprising two or more electrodes disposed on a first side of a first substrate, the first substrate including a flexible and electrically insulating material; a microfluidic device comprising a second substrate including a flexible and electrically insulating material and coupled to the first side of the first substrate at a top side of the second substrate, the second substrate structured to include (i) a channel in a first cavity on the top side, (ii) one or more holes on a bottom side of the second substrate that connect to the channel and provide one or more inlets, and (iii) a reservoir in a second cavity connected to the channel, wherein the electrochemical sensor on the first substrate is aligned with the reservoir of the second substrate; and an adhesion layer coupled to the second substrate and attachable to skin, the adhesion layer structured to include one or more openings arranged on the adhesion layer to align with the one or more inlets and the outlet of the second substrate, wherein the second substrate is positioned between the first substrate and the adhesion layer, wherein, when the device is electrically coupled to an electronics unit and adhered to the skin of a user, the device is operable to detect a biomarker in a fluid in secreted by the skin into the microfluidic device.

Example B2 includes the device of example B1, wherein the reservoir further comprises one or more pillars to support the two or more electrodes.

Example B3 includes the device of example B1, wherein the electrochemical sensor includes: a first electrode having a surface that includes a catalyst or a reactant corresponding to an analyte in the fluid, and a second electrode disposed on the first substrate in a location separated from the first electrode, the first and second electrodes operable to measure an electrical signal corresponding to a redox reaction including the chemical substance and the analyte at the electrochemical sensor.

Example B4 includes the device of example B1, wherein the flexible and electrically insulating material of the first substrate and the second substrate includes polydimethylsiloxane (PDMS).

Example B5 includes the device of example B1, wherein the first substrate, the second substrate and the adhesion layer are configured as three circular, flexible layers having a diameter in a range of 1 cm to 10 cm.

Example B6 includes the device of example B1, wherein the analyte includes glucose or lactate.

Example B7 includes the device of example B1, wherein the electronics unit is electrically coupled to the electrochemical sensor via electrical interconnects, the electronics unit configured to supply electrical energy to the electrochemical sensor.

Example B8 includes the device of example B1, further comprising a biofuel cell, wherein the device includes the electronics unit electrically coupled to the electrochemical sensor via electrical interconnects and the biofuel cell, the biofuel cell configured to supply electrical energy to the electrochemical sensor.

Example B9 includes the device of example B1, wherein the biofuel cell is a microfluidic biofuel cell including separate anodic and cathodic fluid reservoirs containing enzyme-functionalized porous packing fabricated between two layers.

Example B10 includes the device of example B1, wherein the electrochemical sensor comprises a third electrode.

Example B11 includes the device of example B1, wherein the electrochemical sensor comprises a fourth electrode.

Example B12 includes the device of example B1, wherein the electrochemical sensor is operable to obtain one or more of amperometric measurements, potentiometric measurement, or square-wave voltammetric measurements.

Example B13 includes the device of example B1, wherein the electronics unit includes: a signal conditioning circuit to amplify signals detected by the electrochemical sensor, a data processing unit including a processor and memory to process data based on the measured signals, and a wireless communications unit to wirelessly transmit the processed signals to an external device.

Example B14 includes the device of example B13, wherein the wireless communications unit includes a Bluetooth® Low Energy chipset.

In some embodiments in accordance with the present technology (example C1), a wearable electrochemical sensor device includes a first flexible substrate including an electrically insulating material; two or more electrodes disposed on the first flexible substrate; a second flexible substrate coupled to the first flexible substrate on a first side of the second flexible substrate, the second substrate including an electrically insulating material and wherein the second substrate is structured to include (i) a channel that recedes from the surface of the first side of the second flexible substrate, (ii) a first set of one or more holes on a second side of the second flexible substrate that connect to a first region of the channel to provide one or more inlets, (iii) a cavity intersecting the channel beyond the first region to provide a reservoir, (iv) a second set of one or more holes that connect to a second region of the channel opposite the first region to provide one or more outlets, wherein the two or more electrodes on the first flexible substrate are aligned with the reservoir of the second flexible substrate; and an adhesion layer coupled to the second substrate and attachable to skin, the adhesion layer structured to include one or more openings arranged on the adhesion layer to align with the one or more inlets, wherein, when the device is electrically coupled to an electronics unit and adhered to the skin of a user, the device is operable to detect a biomarker in a fluid secreted from the skin of the user into the device.

Example C2 includes the device of any of examples C1-C19, wherein the reservoir further comprises one or more pillars to support the first flexible substrate.

Example C3 includes the device of any of examples C1-C19, wherein a first electrode of the two or more electrodes having a surface that includes a catalyst or a reactant corresponding to an analyte in the fluid, and wherein a second electrode of the two or more electrodes is disposed on the first flexible substrate in a location separated from the first electrode, the first electrode and second electrode operable to measure an electrical signal corresponding to a redox reaction including a chemical substance and the analyte at the first electrode and second electrode.

Example C4 includes the device of any of examples C1-C19, wherein the electronics unit is electrically coupled to the wearable electrochemical sensor device via electrical interconnects, the electronics unit configured to supply electrical energy to at least some of the two or more electrodes.

Example C5 includes the device of example C4, wherein the electronics unit includes: a signal conditioning circuit to amplify signals detected by the electrochemical sensor device, a data processing unit including a processor and memory to process data based on the measured signals, and a wireless communications unit to wirelessly transmit the processed signals to an external device.

Example C6 includes the device of example C5, wherein the wireless communications unit includes a Bluetooth® Low Energy chipset.

Example C7 includes the device of any of examples C1-C19, wherein one or both of the first flexible substrate and the second substrate comprises polydimethylsiloxane (PDMS).

Example C8 includes the device of any of examples C1-C19, wherein the first flexible substrate, the second substrate and the adhesion layer are configured as three circular, flexible layers having a diameter in a range of 1 cm to 10 cm.

Example C9 includes the device of any of examples C1-C19, further comprising a biofuel cell, wherein the device includes the electronics unit electrically coupled to the two or more electrodes via electrical interconnects and the biofuel cell, the biofuel cell configured to supply electrical energy to the two or more electrodes for electrochemical detection of the biomarker in the fluid.

Example C10 includes the device of example C9, wherein the biofuel cell is a microfluidic biofuel cell including: an anodic reservoir containing a first catalyst capable of oxidizing a component of the fluid secreted from the skin of the user and generating an electron, wherein the first catalyst is an enzyme; a cathodic reservoir containing a second catalyst capable of reducing an oxidant by accepting the electron generated in the anodic reservoir, wherein the second catalyst is an enzyme; and an external circuit that connects the anodic and cathodic reservoirs, wherein the electron generated in the anodic reservoir travels through the external circuit and into the cathodic reservoir, wherein when the first and second catalysts are in contact with the fluid secreted from the skin of the user a chemical reaction occurs resulting in a signal representative of a level of the biomarker in the fluid secreted by the skin of the user.

Example C11 includes the device of any of examples C1-C19, wherein the device is operable to obtain one or more of amperometric measurements, potentiometric measurement, or square-wave voltammetric measurements.

Example C12 includes the device of any of examples C1-C19, wherein the reservoir can fill with the fluid secreted from the skin of the user in less than 5 minutes.

Example C13 includes the device of any of examples C1-C19, wherein the device enables a constant, rapid fluid transport to the reservoir.

Example C14 includes the device of any of examples C1-C19, wherein the device can simultaneously detect two or more biomarkers.

Example C15 includes the device of any of examples C1-C19, wherein the device is resilient to mechanical deformations, wherein the mechanical deformations include bending, stretching, compressing, and/or twisting.

Example C16 includes the device of any of examples C1-C19, wherein the device is stable to repeated use for at least 5 days.

Example C17 includes the device of any of examples C1-C19, wherein the biomarker is one or more of an electrolyte, glucose, lactate, a pro-inflammatory cytokine, an anti-inflammatory cytokine, a catecholamine, a neuropeptide, and/or a protein.

Example C18 includes the device of example C17, wherein the electrolyte is one or more of sodium, potassium, chloride, bicarbonate, calcium, phosphate, magnesium, copper, zinc, iron, manganese, molybdenum, copper, and chromium.

Example C19 includes the device of any of examples C1-C19, wherein the two or more electrodes are ion-selective electrodes selected from the group consisting of sodium, potassium, chloride, bicarbonate, calcium, phosphate, magnesium, copper, zinc, iron, manganese, molybdenum, copper, and chromium ion-selective electrodes.

In some embodiments in accordance with the present technology (example D1), a method for detecting a biomarker in a fluid on skin of a user includes capturing, by a wearable electrochemical sensor device adhered to the skin of the user, a fluid secreted from the skin of the user in one or more inlets of the wearable electrochemical sensor device; transferring, through a channel of the wearable electrochemical device, the captured fluid to a reservoir of the wearable electrochemical sensor device; measuring one or more biomarkers present in the fluid secreted from the skin of the user, the measuring including electrochemically detecting the one or more biomarkers using two or more electrodes positioned in the reservoir of the wearable electrochemical sensor device; and directing the fluid secreted from the skin of the user out of the reservoir to expel from the device, whereby fresh fluid secreted from the skin of the user is transferred in the reservoir of the wearable electrochemical sensor device for continuous electrochemical detection.

Example D2 includes the method of any of examples D1-D13, wherein adhesion of the wearable electrochemical sensor device to the skin of the user provides a pressure sufficient for the wearable electrochemical sensor device to direct the fluid secreted by the skin of the user to the reservoir without the application an external pressure.

Example D3 includes the method of any of examples D1-D13, wherein the electrochemical sensor device comprises: an electrochemical sensor comprising the two or more electrodes disposed on a first side of a first flexible substrate, a microfluidic device comprising a second flexible substrate, the second flexible substrate structured to include (i) the channel, (ii) a first set of one or more holes that connect to a first end of the channel to provide the one or more inlets, (iii) the reservoir intersecting the channel, wherein the electrochemical sensor on the first flexible substrate is aligned with the reservoir of the second flexible substrate, and (iv) a second set of one or more holes connected to the channel to provide one or more outlets, wherein the two or more electrodes on the side of the first flexible substrate are aligned with the reservoir the second flexible substrate; and an adhesion layer coupled to the second flexible substrate and attachable to skin, the adhesion layer structured to include one or more openings arranged on the adhesion layer to align with the one or more inlets.

Example D4 includes the method of example D3, wherein the reservoir further comprises one or more pillars to support the first flexible substrate or two or more electrodes.

Example D5 includes the method of example D3, wherein when the wearable electrochemical sensor device is electrically coupled to an electronics unit.

Example D6 includes the method of any of examples D1-D13, wherein the reservoir can fill with the fluid secreted from the skin of the user in less than 5 minutes.

Example D7 includes the method of any of examples D1-D13, wherein the capturing and transferring provides a constant, rapid fluid replenishment to the reservoir.

Example D8 includes the method of any of examples D1-D13, wherein the measuring the one or more biomarkers simultaneously detects two or more biomarkers.

Example D9 includes the method of any of examples D1-D13, wherein, during the capturing, transferring, measuring, and directing, the wearable electrochemical sensor device is resilient to mechanical deformations including one or more of bending, stretching, compressing, or twisting.

Example D10 includes the method of any of examples D1-D13, wherein the wearable electrochemical sensor device is stable to implement the method repeatedly for at least 5 days.

Example D11 includes the method of any of examples D1-D13, wherein the biomarkers are one or more of an electrolyte, glucose, lactate, a pro-inflammatory cytokine, an anti-inflammatory cytokine, a catecholamine, a neuropeptide, and/or a protein.

Example D12 includes the method of any of examples D1-D13, wherein two or more electrodes are ion-selective electrodes, wherein the wherein the ion-selective electrodes are selected from the group consisting of sodium, potassium, chloride, bicarbonate, calcium, phosphate, magnesium, copper, zinc, iron, manganese, molybdenum, copper, and chromium ion-selective electrode.

Example D13 includes the method of example D31, wherein the electrolyte is one or more of sodium, potassium, chloride, bicarbonate, calcium, phosphate, magnesium, copper, zinc, iron, manganese, molybdenum, copper, and chromium.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit", "data processing system", and/or "data processing device or apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A wearable electrochemical sensor device, comprising:
   a first flexible substrate including an electrically insulating material;
   two or more electrodes disposed on the first flexible substrate;
   a second flexible substrate coupled to the first flexible substrate on a first side of the second flexible substrate, the second substrate including an electrically insulating material and wherein the second substrate is structured to include (i) a channel that recedes from surface of the first side of the second flexible substrate, (ii) a first set of one or more holes on a second side of the second flexible substrate that connects to a first region of the channel to provide one or more inlets, (iii) a cavity intersecting the channel beyond the first region to provide a reservoir, (iv) a second set of one or more holes that connects to a second region of the channel opposite the first region to provide one or more outlets, wherein the two or more electrodes on the first flexible substrate are aligned with the reservoir of the second flexible substrate; and
   an adhesion layer coupled to the second substrate and attachable to skin, the adhesion layer structured to include one or more openings arranged on the adhesion layer to align with the one or more inlets,
   wherein, when the device is electrically coupled to an electronics unit and adhered to the skin of a user, the two or more electrodes are operable to detect a biomarker in a fluid secreted from the skin of the user into the device,
   wherein the reservoir further comprises one or more pillars to support the first flexible substrate.

2. The device of claim 1, wherein the device further includes the electronics unit, and wherein the device is electrically coupled to the electronics unit via electrical interconnects, and the electronics unit is configured to supply electrical energy to at least some of the two or more electrodes.

3. The device of claim 2, wherein the electronics unit includes:
   a signal conditioning circuit to amplify the electrical signal measured by the first electrode and the second electrode of the device,
   a data processing unit including a processor and memory to process data based on the amplified electrical signals, and
   a wireless communications unit to wirelessly transmit the processed signals data to an external device.

4. The device of claim 3, wherein the wireless communications unit includes a wireless chipset.

5. The device of claim 1, wherein one or both of the first flexible substrate and the second substrate comprises polydimethylsiloxane.

6. The device of claim 1, wherein the first flexible substrate, the second substrate and the adhesion layer are configured as three circular, flexible layers having a diameter in a range of 1 cm to 10 cm.

7. The device of claim 1, further comprising a biofuel cell, wherein the device includes the electronics unit electrically coupled to the two or more electrodes via electrical interconnects and the biofuel cell, wherein the biofuel cell is configured to supply electrical energy to the two or more electrodes for electrochemical detection of the biomarker in the fluid.

8. The device of claim 7, wherein the biofuel cell is a microfluidic biofuel cell including:
   an anodic reservoir containing a first catalyst capable of oxidizing a component of the fluid secreted from the skin of the user and generating an electron, wherein the first catalyst is an enzyme;
   a cathodic reservoir containing a second catalyst capable of reducing an oxidant by accepting the electron generated in the anodic reservoir, wherein the second catalyst is an enzyme; and
   an external circuit that connects the anodic and cathodic reservoirs, wherein the electron generated in the anodic reservoir is able to travel through the external circuit and into the cathodic reservoir, wherein, when the first and second catalysts are in contact with the fluid secreted from the skin of the user, a chemical reaction occurs resulting in a signal representative of a level of the biomarker in the fluid secreted by the skin of the user.

9. The device of claim 1, wherein the device is operable to obtain one or more of amperometric measurements, potentiometric measurement, or square-wave voltammetric measurements.

10. The device of claim 1, wherein the reservoir is operable to be filled with the fluid secreted from the skin of the user in less than 5 minutes.

11. The device of claim 1, wherein the device is operable to enable a constant fluid transport to the reservoir, the fluid secreted from the skin of the user reaching the reservoir in under 5 minutes.

12. The device of claim 1, wherein the two or more electrodes are further configured to simultaneously detect the biomarker or two or more of different biomarkers.

13. The device of claim 1, wherein the device is resilient to mechanical deformations, wherein the mechanical deformations include bending, stretching, compressing, and/or twisting.

14. The device of claim 1, wherein the first flexible substrate, the second flexible substrate, and the adhesion layer are configured to enable the device to sustain repeated use for at least 5 days.

15. The device of claim 1, wherein the biomarker is one or more of an electrolyte, glucose, lactate, a pro-inflammatory cytokine, an anti-inflammatory cytokine, a catecholamine, a neuropeptide, and/or a protein.

16. The device of claim 15, wherein the electrolyte is one or more of sodium, potassium, chloride, bicarbonate, calcium, phosphate, magnesium, copper, zinc, iron, manganese, molybdenum, copper, and chromium.

17. The device of claim 1, wherein the two or more electrodes are ion-selective electrodes selected from the group consisting of sodium, potassium, chloride, bicarbonate, calcium, phosphate, magnesium, copper, zinc, iron, manganese, molybdenum, copper, and chromium ion-selective electrodes.

18. A wearable electrochemical sensor device, comprising:
a first flexible substrate including an electrically insulating material;
two or more electrodes disposed on the first flexible substrate;
a second flexible substrate coupled to the first flexible substrate on a first side of the second flexible substrate, the second substrate including an electrically insulating material and wherein the second substrate is structured to include (i) a channel that recedes from surface of the first side of the second flexible substrate, (ii) a first set of one or more holes on a second side of the second flexible substrate that connects to a first region of the channel to provide one or more inlets, (iii) a cavity intersecting the channel beyond the first region to provide a reservoir, (iv) a second set of one or more holes that connects to a second region of the channel opposite the first region to provide one or more outlets, wherein the two or more electrodes on the first flexible substrate are aligned with the reservoir of the second flexible substrate; and
an adhesion layer coupled to the second substrate and attachable to skin, the adhesion layer structured to include one or more openings arranged on the adhesion layer to align with the one or more inlets,
wherein, when the device is electrically coupled to an electronics unit and adhered to the skin of a user, the two or more electrodes are operable to detect a biomarker in a fluid secreted from the skin of the user into the device,
wherein a first electrode of the two or more electrodes having a surface that includes a catalyst or a reactant corresponding to the biomarker in the fluid, and wherein a second electrode of the two or more electrodes is disposed on the first flexible substrate in a location separated from the first electrode, the first electrode and second electrode operable to measure an electrical signal corresponding to a redox reaction that involves the catalyst or the reactant and the biomarker at the first electrode and second electrode, and
wherein the reservoir further comprises one or more pillars to support the first flexible substrate.

19. The device of claim 18, wherein the device further includes the electronics unit, and wherein the device is electrically coupled to the electronics unit via electrical interconnects, and the electronics unit is configured to supply electrical energy to at least some of the two or more electrodes.

20. The device of claim 18, wherein one or both of the first flexible substrate and the second substrate comprises polydimethylsiloxane.

21. The device of claim 18, wherein the device is resilient to mechanical deformations, wherein the mechanical deformations include bending, stretching, compressing, and/or twisting.

22. A method for detecting a biomarker in a fluid on skin of a user, the method comprising:
capturing, by a wearable electrochemical sensor device adhered to the skin of the user, the fluid secreted from the skin of the user in one or more inlets of the wearable electrochemical sensor device;
transferring, through a channel of the wearable electrochemical device, the captured fluid to a reservoir of the wearable electrochemical sensor device;
measuring one or more biomarkers present in the fluid secreted from the skin of the user, the measuring including electrochemically detecting the one or more biomarkers using two or more electrodes positioned in the reservoir of the wearable electrochemical sensor device; and
directing the fluid secreted from the skin of the user out of the reservoir to expel from the device, whereby fresh fluid secreted from the skin of the user is transferred in the reservoir of the wearable electrochemical sensor device for continuous electrochemical detection,
wherein the wearable electrochemical sensor device comprises:
an electrochemical sensor comprising the two or more electrodes disposed on a first side of a first flexible substrate,
a microfluidic device comprising a second flexible substrate, the second flexible substrate structured to include (i) the channel, (ii) a first set of one or more holes that connects to a first end of the channel to provide the one or more inlets, (iii) the reservoir intersecting the channel, wherein the electrochemical sensor on the first flexible substrate is aligned with the reservoir of the second flexible substrate, and (iv) a second set of one or more holes connected to the channel to provide one or more outlets, wherein the two or more electrodes on the side of the first flexible substrate are aligned with the reservoir the second flexible substrate; and an adhesion layer coupled to the second flexible substrate and attachable to the skin, the adhesion layer structured to include one or more openings arranged on the adhesion layer to align with the one or more inlets, wherein the reservoir further comprises one or more pillars to support the first flexible substrate or the two or more electrodes.

23. The method of claim 22, wherein adhesion of the wearable electrochemical sensor device to the skin of the user provides a pressure sufficient for the wearable electrochemical sensor device to direct the fluid secreted by the skin of the user to the reservoir without the application an external pressure.

24. The method of claim 22, wherein when the wearable electrochemical sensor device is electrically coupled to an electronics unit.

25. The method of claim 22, wherein the reservoir is operable to be filled with the fluid secreted from the skin of the user in less than 5 minutes.

26. The method of claim 22, wherein the capturing and transferring provides a constant fluid replenishment to the reservoir, the fluid secreted from the skin of the user reaching the reservoir in under 5 minutes.

27. The method of claim 22, wherein the measuring the one or more biomarkers simultaneously detects two or more biomarkers.

28. The method of claim 22, wherein, during the capturing, transferring, measuring, and directing, the wearable electrochemical sensor device is resilient to mechanical deformations including one or more of bending, stretching, compressing, or twisting.

29. The method of claim 22, wherein the wearable electrochemical sensor device is sustainable to implement the method repeatedly for at least 5 days.

30. The method of claim 22, wherein the biomarkers are one or more of an electrolyte, glucose, lactate, a pro-inflammatory cytokine, an anti-inflammatory cytokine, a catecholamine, a neuropeptide, and/or a protein.

31. The method of claim 30, wherein the electrolyte is one or more of sodium, potassium, chloride, bicarbonate, calcium, phosphate, magnesium, copper, zinc, iron, manganese, molybdenum, copper, and chromium.

32. The method of claim 22, wherein the two or more electrodes are ion-selective electrodes, wherein the ion-selective electrodes are selected from the group consisting of sodium, potassium, chloride, bicarbonate, calcium, phosphate, magnesium, copper, zinc, iron, manganese, molybdenum, copper, and chromium ion-selective electrode.

* * * * *